US008652439B2

(12) United States Patent
Cohen et al.

(10) Patent No.: US 8,652,439 B2
(45) Date of Patent: Feb. 18, 2014

(54) COMPOSITIONS OF HSP60 PEPTIDES AND VIRAL ANTIGENS FOR VACCINATION AND DIAGNOSIS

(75) Inventors: Irun R. Cohen, Rehovot (IL); Bracha Rager-Zisman, Beer Sheva (IL); Angel Porgador, Lehavim (IL); Johannes Herkel, Hamburg (DE)

(73) Assignees: Yeda Research and Development Co. Ltd., Rehovot (IL); B.G. Negev Technologies and Applications Ltd., Beer Sheva (IL)

( * ) Notice: Subject to any disclaimer, the term of this patent is extended or adjusted under 35 U.S.C. 154(b) by 0 days.

(21) Appl. No.: 13/164,411

(22) Filed: Jun. 20, 2011

(65) Prior Publication Data

US 2011/0256165 A1 Oct. 20, 2011

Related U.S. Application Data

(62) Division of application No. 11/908,474, filed as application No. PCT/IL2006/000222 on Feb. 21, 2006, now abandoned.

(60) Provisional application No. 60/661,017, filed on Mar. 14, 2005.

(51) Int. Cl.
*A61K 51/00* (2006.01)
*A61K 45/00* (2006.01)
*C12Q 1/68* (2006.01)

(52) U.S. Cl.
USPC ........................ 424/1.69; 424/1.11; 424/278.1

(58) Field of Classification Search
None
See application file for complete search history.

(56) References Cited

U.S. PATENT DOCUMENTS

| | | | |
|---|---|---|---|
| 4,073,943 A | 2/1978 | Wretlind | |
| 4,168,308 A | 9/1979 | Wretlind et al. | |
| 5,154,923 A | 10/1992 | Van Eden | |
| 5,736,146 A | 4/1998 | Cohen | |
| 5,869,058 A | 2/1999 | Cohen et al. | |
| 5,961,970 A | 10/1999 | Lowell | |

FOREIGN PATENT DOCUMENTS

| | | |
|---|---|---|
| EP | 262710 | 6/1988 |
| WO | 95/31994 | 11/1995 |
| WO | 90/10449 | 9/1999 |
| WO | 02/062959 | 8/2002 |
| WO | 03/026579 | 4/2003 |
| WO | 2004/016586 | 2/2004 |

OTHER PUBLICATIONS

Roman "Synthetic peptides non-covalently bound to bacterial hsp 70 elicit peptide-specific T-cell responses in vivo E." Immunology 1996, 88:487-492.*

(Continued)

*Primary Examiner* — Jeffrey Stucker
*Assistant Examiner* — Stuart W Snyder
(74) *Attorney, Agent, or Firm* — Rodney J. Fuller; Booth Udall Fuller, PLC

(57) ABSTRACT

The present invention provides improved vaccines comprising an isolated viral antigenic peptide and a synthetic peptide derived from a T cell epitope of HSP60. The invention includes mixtures where the peptide serves as an adjuvant as well as conjugates where the peptide is covalently linked to the viral antigen. The known synthetic peptide carrier, p458, provides significantly improved immunogenicity for synthetic viral epitopes and analogs. Ec27 is a novel peptide derived from HSP60 which increases the immunogenicity substantially of the viral antigen both as a mixture or a covalent conjugate. Some of the isolated viral epitopes are novel and are claimed for diagnostic as well as therapeutic or prophylactic uses.

17 Claims, 18 Drawing Sheets

(56) References Cited

OTHER PUBLICATIONS

Nybakken et a. "Structural basis of West Nile virus neutralization by a therapeutic antibody" (Nature, Sep. 2005, 437(29):764-7680.*
Aaskov "Serologically defined linear epitopes in the envelope protein of dengue 2 (Jamaica strain 1409)" Arch Virol. 105:209-221, 1989.*
Bowie, et al. Deciphering the Message in Protein Sequences: Tolerance to Amino Acid Substitutions, Science, 1990; 247(4948): 1306-1310.*
Guo, et al. Protein tolerance to random amino acid change. Proc. Natl. Acad. Sci. USA, 2004; 101(25): 9205-9210.*
Marini, et al. The Use of Orthologous Sequences to Predict the Impact of Amino Acid Substitutions on Protein Function. PLoS Genetics. 2010; 6(5): 1-11.*
Amir-Kroll H. et al., "Proteins and their derived peptides as carriers in a conjugate vaccine for *Streptococcus pneumoniae*: self-heat shock protein 60 and tetanus toxoid", J Immunol, 170(12):6165-6171 (2003).
Anderton S. M. et al., "Inflammation activates self hsp60-specific T cells", Eur J Immunol, 23(1):33-38 (1993).
Barrios C. et al., "Mycobacterial heat-shock proteins as carrier molecules. II: the use of the 70-kDa mycobacterial heat-shock protein as carrier for conjugated vaccines can circumvent the need for adjuvants and Bacillus Calmette Guérin priming", Eur S of Immuol, 1992; 22(6):1365-1372 (1992).
Beasley David WC. et al., (2002) Identification of neutralizing epitopes within structural domain III of the West Nile virus envelope protein. J Virol. 76(24):13097-13100 (2002).
Ben-Nathan D. et al., "West Nile virus neuroinvasion and encephalitis induced by macrophage depletion in mice", Arch Virol, 141(3-4):459-469 (1996).
Ben-Nathan D. et al., "Prophylactic and therapeutic efficacy of human intravenous immunoglobulin in treating West Nile virus infection in mice", J Infect Dis, 188(1):5-12 (2003).
Brander C. et al., "Peptide immunization in humans: a combined CD8+/CD4+ T cell-targeted vaccine restimulates the memory CD4 T cell response but fails to induce cytotoxic T lymphocytes (CTL)", Clin Exp Immunol, 105(1):18-25 (1996).
Casadevall A., "Antibodies for defense against biological attack", Nat Biotechnol 2002; 20(2):114 (2002).
Cohen I. R., "The cognitive paradigm and the immunological homunculus", Immunol Today, 13(12):490-494 (1992).
Goldblum N. et al., "West Nile fever; the clinical features of the disease and the isolation of West Nile virus from the blood of nine human cases", Am J Hyg, 59(1):89-103 (1954).
Hall R. A. et al., "DNA vaccine coding for the full-length infectious Kunjin virus RNA protects mice against the New York strain of West Nile virus", Proc Natl Acad Sci U S A, 100(18):10460-10464 (2003).
Hermann E. et al., "Synovial fluid-derived Yersinia-reactive T cells responding to human 65-kDa heat-shock protein and heat-stressed antigen-presenting cells", Eur J Immunol, 21(9):2139-2143 (1991).
Jindal S. et al., "Primary structure of a human mitochondrial protein homologous to the bacterial and plant chaperonins and to the 65-kilodalton mycobacterial antigen", Mol Cell Biol, 9(5):2279-2283 (1989).
Keitel W. A. et al., "Phase I trial of two recombinant vaccines containing the 19kd carboxy terminal fragment of Plasmodium falciparum merozoite surface protein 1 (msp-1(19)) and T helper epitopes of tetanus toxoid", Vaccine, 18 (5-6):531-539 (2000).
Kirchner H., "Immunobiology of infection with human cytomegalovirus", Adv Cancer Res, 40:31-105 (1983).
Koga T. et al., "T cells against a bacterial heat shock protein recognize stressed macrophages", Science, 245(4922):1112-1115 (1989).
Kolaskar and Tongaonkar., "A semi-empirical method for prediction of antigenic determinants on protein antigens", FEBS Lett, 276(1-2):172-174 (1990).
Konen Waisman S. et al., "Self and foreign 60-kilodalton heat shock protein T cell epitope peptides serve as immunogenic carriers for a T cell-independent sugar antigen", J Immunol, 154(11):5977-5985 (1995).
Konen Waisman S. et al., "Self heat-shock protein (hsp60) peptide serves in a conjugate vaccine against a lethal pneumococcal infection", J Infect Dis, 179(2):403-413 (1999).
Koszinowski U. H. et al., "Cellular and molecular basis of the protective immune response to cytomegalovirus infection", Curr Top Microbiol Immunol, 154:189-220 (1990).
Lussow A. R. et al., "Towards vaccine optimisation", Immunol. Lett, 25(1-3):255-264 (1990).
Lussow A. R. et al., "Mycobacterial heat-shock proteins as carrier molecules", Eur. J. Immunol., 21(10):2297-2302 (1991).
Martin D. A. et al., "Standardization of immunoglobulin M capture enzyme-linked immunosorbent assays for routine diagnosis of arboviral infections", J Clin Microbiol, 38(5):1823-1826 (2000).
Matloubian M. et al., "CD4+ T cells are required to sustain CD8+ cytotoxic T-cell responses during chronic viral infection", J Virol, 68(12):8056-8063 (1994).
Mercer J. A. et al., "Pathogenesis of acute murine cytomegalovirus infection in resistant and susceptible strains of mice", J Virol, 57(2):497-504 (1986).
Monath A., "Prospects for development of a vaccine against the West Nile virus", N Y Acad Sci, 951:1-12 (2001).
Palmon A. et al., "Treatment of murine cytomegalovirus salivary-gland infection by combined therapy with ganciclovir and thymic humoral factor gamma 2", Antiviral Res 33(1):55-64 (1996).
Palmon A. et al., "Development of a highly sensitive quantitative competitive PCR assay for the detection of murine cytomegalovirus DNA", J Virol Methods, 86(2):107-114 (2000).
Panina-Bordignon P. et al., "Universally immunogenic T cell epitopes: promiscuous binding to human MHC class II and promiscuous recognition by T cells", Eur J Immunol, 19(12):2237-2342 (1989).
Plentev A.G. et al., "Molecularly engineered live-attenuated chimeric West Nile/dengue virus vaccines protect rhesus monkeys from West Nile virus", Virology, 314(1):190-195 (2003).
Quintana FJ. et al., "DNA fragments of the human 60-kDa heat shock protein (HSP60) vaccinate against adjuvant arthritis: identification of a regulatory HSP60 peptide", J Immunol., 171(7):3533-3541 (2003).
Quintana FJ. et al., "Inhibition of adjuvant arthritis by a DNA vaccine encoding human heat shock protein 60", J Immunol., 169(6):3422-3428 (2002).
Rager Zisman and Merigan, "A useful quantitative semimicromethod for viral plaque assay", Proc Soc Exp Biol Med, 142(4):1174-1179 (1973).
Rapp M. et al., "Identification of the murine cytomegalovirus glycoprotein B gene and its expression by recombinant vaccinia virus", J Virol, 66(7):4399-4406 (1992).
Reddehase et al., "A pentapeptide as minimal antigenic determinant for MHC class I-restricted T lymphocytes", Nature, 337(6208):651-653 (1989).
Reizis B. et al., "The peptide binding specificity of the MHC class II I-A molecule of the Lewis rat, RT1.B1.", Int Immunol 8(12):1825-1832 (1996).
Rouvio O. et al., "Self HSP60 peptide serves as an immunogenic carrier for a CTL epitope against persistence of murine cytomegalovirus in the salivary gland", Vaccine, 23(27):3508-3518 (2005).
Stanley, "A member of the Hsp60 gene family from the peach potato aphid, Myzus persicae (Sulzer)", Insect Mol Biol., 9(2):211-215 (2000).
Tesh et al., "Efficacy of killed virus vaccine, live attenuated chimeric virus vaccine, and passive immunization for prevention of West Nile virus encephalitis in hamster model", Emerg Infect Dis, 8(12):1392-1397 (2002).
Ulmann E. and Peyman A., "Antisense oligonucleotides: a new therapeutic principle", Chem Rev, 90(4):543-584 (1990).
Volk David E et al., "Solution structure and antibody binding studies of the envelope protein domain III from the New York strain of West Nile virus", J Biol Chem, 279(37):38755-38761 (2004).
Yewdell J. W. et al., "Monoclonal antibody analysis of p53 expression in normal and transformed cells", J Virol, 59(2):444-452 (1986).
Zajac et al., "Therapeutic vaccination against chronic viral infection: the importance of cooperation between CD4+ and CD8+ T cells", Curr Opin Immunol, 10(4):444-449 (1998).
Database UniPort [online] Nov. 23, 2004, "Heat shock protein Hsp60 (fragment)." XP002475531 retrieved from EBI accession No. UNIPORT:Q5Y971.
Kimura et al., (1986) Antigenic Comparison of Envelope Protein E between Japanese Encephalitis Virus and Some Other Flaviviruses Using Monoclonal Antibodies. J gen Virol 67: 2663-2672.
Wong et al., (2003) Immunoassay Targeting Nonstructural Protein 5 To Differentiate West Nile Virus Infection from Dengue and St. Louis Encephalitis Virus Infections and from Flavivirus Vaccination. Journal of Clinical Microbiology 41(9): 4217-4223.

* cited by examiner

| MCM | + | + | + | + | - |
|---|---|---|---|---|---|
| GCV |  | + | + | + | - |
| p458m -89pep |  |  | + |  | - |
| 89pep |  |  |  | + | - |

| Treatment | Virus titers (pfu/ml) | RT-PCR WNV Ep | RT-PCR β actin |
|---|---|---|---|
| Virus only | $4 \times 10^8$ | 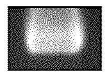  |  |
| p32 immunization | $<10^1$* |  |  |
| Naive | $<10^1$ |  |  |

SEQUENCE LISTING

```
<160> NUMBER OF SEQ ID NOS: 87

<210> SEQ ID NO 1
<211> LENGTH: 17
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 1

Asn Glu Asp Gln Lys Ile Gly Ile Glu Ile Ile Lys Arg Thr Leu Lys
1               5                   10                  15

Ile

<210> SEQ ID NO 2
<211> LENGTH: 17
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 2

Asn Glu Asp Gln Lys Ile Gly Ile Glu Ile Ile Lys Arg Ala Leu Lys
1               5                   10                  15

Ile

<210> SEQ ID NO 3
<211> LENGTH: 17
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 3

Glu Gly Asp Glu Ala Thr Gly Ala Asn Ile Val Lys Val Ala Leu Glu
1               5                   10                  15

Ala

<210> SEQ ID NO 4
<211> LENGTH: 17
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 4

Asn Glu Asp Gln Asn Val Gly Ile Lys Val Ala Leu Arg Ala Met Glu
1               5                   10                  15

Ala

<210> SEQ ID NO 5
<211> LENGTH: 9
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 5
```

Tyr Pro His Phe His Pro Thr Asn Leu
1               5

<210> SEQ ID NO 6
<211> LENGTH: 26
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 6

Asn Glu Asp Gln Lys Ile Gly Ile Glu Ile Ile Lys Arg Ala Leu Lys
1               5                   10                  15

Ile Tyr Pro His Phe His Pro Thr Asn Leu
            20                  25

<210> SEQ ID NO 7
<211> LENGTH: 16
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 7

Glu Gly Asp Glu Ala Thr Gly Ala Asn Ile Lys Val Ala Leu Glu Ala
1               5                   10                  15

<210> SEQ ID NO 8
<211> LENGTH: 25
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 8

Glu Gly Asp Glu Ala Thr Gly Ala Asn Ile Lys Val Ala Leu Glu Ala
1               5                   10                  15

Tyr Pro His Phe His Pro Thr Asn Leu
            20                  25

<210> SEQ ID NO 9
<211> LENGTH: 30
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 9

Phe Asn Asn Phe Thr Val Ser Phe Trp Leu Arg Val Pro Lys Val Ser
1               5                   10                  15

Ala Ser His Leu Glu Tyr Pro His Phe Met Pro Thr Asn Leu
            20                  25                  30

<210> SEQ ID NO 10
<211> LENGTH: 21
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 10

Phe Asn Asn Phe Thr Val Ser Phe Trp Leu Arg Val Pro Lys Val Ser
1               5                   10                  15

Ala Ser His Leu Glu
            20

<210> SEQ ID NO 11
<211> LENGTH: 15
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 11

Leu Val Thr Val Asn Pro Phe Val Ser Val Ala Thr Ala Asn Ser
1               5                   10                  15

<210> SEQ ID NO 12
<211> LENGTH: 15
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 12

Leu Val Thr Val Asn Pro Phe Val Ser Val Ala Thr Ala Asn Ala
1               5                   10                  15

<210> SEQ ID NO 13
<211> LENGTH: 32
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 13

Asn Glu Asp Gln Lys Ile Gly Ile Glu Ile Ile Lys Arg Ala Leu Lys
1               5                   10                  15

Ile Leu Val Thr Val Asn Pro Phe Val Ser Val Ala Thr Ala Asn Ser
            20                  25                  30

<210> SEQ ID NO 14
<211> LENGTH: 32
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 14

Asn Glu Asp Gln Lys Ile Gly Ile Glu Ile Ile Lys Arg Ala Leu Lys
1               5                   10                  15

Ile Leu Val Thr Val Asn Pro Phe Val Ser Val Ala Thr Ala Asn Ala
            20                  25                  30

<210> SEQ ID NO 15
<211> LENGTH: 32
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 15

Asn Glu Asp Gln Lys Ile Gly Ile Glu Ile Ile Lys Arg Thr Leu Lys
1               5                   10                  15

Ile Leu Val Thr Val Asn Pro Phe Val Ser Val Ala Thr Ala Asn Ser
            20                  25                  30

<210> SEQ ID NO 16
<211> LENGTH: 32
<212> TYPE: PRT
<213> ORGANISM: ARTIFICIAL SEQUENCE

-continued

```
<220> FEATURE:
<223> OTHER INFORMATION: SYNTHETIC PEPTIDE

<400> SEQUENCE: 16

Asn Glu Asp Gln Lys Ile Gly Ile Glu Ile Ile Lys Arg Thr Leu Lys
1               5                   10                  15

Ile Leu Val Thr Val Asn Pro Phe Val Ser Val Ala Thr Ala Asn Ala
            20                  25                  30

<210> SEQ ID NO 17
<211> LENGTH: 27
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 17
aagcagcaca tccgcaccct gagcgcc                                       27

<210> SEQ ID NO 18
<211> LENGTH: 27
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 18
ccaggcgctc ccggcggccc gctctcg                                       27

<210> SEQ ID NO 19
<211> LENGTH: 45
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 19
ctggtgaccg tgaatccatt tgtgtctgtg gccacagcca actcg                   45

<210> SEQ ID NO 20
<211> LENGTH: 45
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 20
ttggtcactg tcaacccttt tgtttcagtg gccacggcca acgct                   45

<210> SEQ ID NO 21
<211> LENGTH: 17
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 21

Tyr Ile Val Val Gly Arg Gly Glu Gln Gln Ile Asn His His Trp His
1               5                   10                  15

Lys

<210> SEQ ID NO 22
<211> LENGTH: 51
<212> TYPE: DNA
<213> ORGANISM: ARTIFICIAL SEQUENCE
<220> FEATURE:
```

<223> OTHER INFORMATION: SYNTHETIC OLIGONUCLEOTIDE

<400> SEQUENCE: 22
tatattgtgg tgggccgcgg cgaacagcag attaaccatc attggcataa a    51

<210> SEQ ID NO 23
<211> LENGTH: 34
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 23

Asn Glu Asp Gln Lys Ile Gly Ile Glu Ile Ile Lys Arg Ala Leu Lys
1               5                   10                  15

Ile Tyr Ile Val Val Gly Arg Gly Glu Gln Gln Ile Asn His His Trp
            20                  25                  30

His Lys

<210> SEQ ID NO 24
<211> LENGTH: 34
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 24

Asn Glu Asp Gln Lys Ile Gly Ile Glu Ile Ile Lys Arg Thr Leu Lys
1               5                   10                  15

Ile Tyr Ile Val Val Gly Arg Gly Glu Gln Gln Ile Asn His His Trp
            20                  25                  30

His Lys

<210> SEQ ID NO 25
<211> LENGTH: 18
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 25

Leu Val Thr Val Asn Pro Ile Ala Ser Thr Asn Asp Asp Glu Val Leu
1               5                   10                  15

Ile Glu

<210> SEQ ID NO 26
<211> LENGTH: 18
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 26

Leu Val Thr Val Asn Pro Phe Ile Ser Thr Gly Gly Ala Asn Asn Lys
1               5                   10                  15

Val Met

<210> SEQ ID NO 27
<211> LENGTH: 18
<212> TYPE: PRT
<213> ORGANISM: ARTIFICIAL SEQUENCE
<220> FEATURE:
<223> OTHER INFORMATION: SYNTHETIC PEPTIDE

```
<400> SEQUENCE: 27

Met Val Thr Ala Asn Pro Tyr Val Ala Ser Ser Thr Ala Asn Ala Lys
1               5                   10                  15

Val Leu

<210> SEQ ID NO 28
<211> LENGTH: 18
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 28

Leu Val Thr Val Asn Pro Phe Val Ser Val Ser Thr Ala Asn Ala Lys
1               5                   10                  15

Val Leu

<210> SEQ ID NO 29
<211> LENGTH: 18
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 29

Leu Val Thr Val Asn Pro Phe Val Ala Thr Ser Ser Ala Asn Ser Lys
1               5                   10                  15

Val Leu

<210> SEQ ID NO 30
<211> LENGTH: 18
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 30

Leu Ile Thr Ala Asn Pro Ile Val Thr Asp Lys Glu Lys Pro Val Asn
1               5                   10                  15

Ile Glu

<210> SEQ ID NO 31
<211> LENGTH: 18
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 31

Leu Ile Thr Val Asn Pro Ile Val Thr Glu Lys Asp Ser Pro Val Asn
1               5                   10                  15

Ile Glu

<210> SEQ ID NO 32
<211> LENGTH: 18
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 32

Leu Ile Thr Ala Asn Pro Val Val Thr Lys Lys Glu Glu Pro Val Asn
1               5                   10                  15
```

Ile Glu

<210> SEQ ID NO 33
<211> LENGTH: 18
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 33

Ile Ile Ser Ser Thr Pro Leu Ala Glu Asn Thr Asn Ser Val Thr Asn
1               5                   10                  15

Ile Glu

<210> SEQ ID NO 34
<211> LENGTH: 17
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 34

Gly Arg Leu Val Thr Val Asn Pro Phe Val Ser Val Ala Thr Ala Asn
1               5                   10                  15

Ser

<210> SEQ ID NO 35
<211> LENGTH: 17
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 35

Gly Arg Leu Val Thr Val Asn Pro Phe Val Ser Val Ala Thr Ala Asn
1               5                   10                  15

Ala

<210> SEQ ID NO 36
<211> LENGTH: 20
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 36

Gly Ile Leu Val Thr Val Asn Pro Ile Ala Ser Thr Asn Asp Asp Glu
1               5                   10                  15

Val Leu Ile Glu
            20

<210> SEQ ID NO 37
<211> LENGTH: 20
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 37

Gly Arg Leu Val Thr Val Asn Pro Phe Ile Ser Thr Gly Gly Ala Asn
1               5                   10                  15

Asn Lys Val Met
            20

```
<210> SEQ ID NO 38
<211> LENGTH: 20
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 38

Gly Arg Met Val Thr Ala Asn Pro Tyr Val Ala Ser Ser Thr Ala Asn
1               5                   10                  15

Ala Lys Val Leu
            20

<210> SEQ ID NO 39
<211> LENGTH: 20
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 39

Gly Arg Leu Val Thr Val Asn Pro Phe Val Ser Val Ser Thr Ala Asn
1               5                   10                  15

Ala Lys Val Leu
            20

<210> SEQ ID NO 40
<211> LENGTH: 20
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 40

Gly Arg Leu Val Thr Val Asn Pro Phe Val Ala Thr Ser Ser Ala Asn
1               5                   10                  15

Ser Lys Val Leu
            20

<210> SEQ ID NO 41
<211> LENGTH: 20
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 41

Gly Arg Leu Ile Thr Ala Asn Pro Ile Val Thr Asp Lys Glu Lys Pro
1               5                   10                  15

Val Asn Ile Glu
            20

<210> SEQ ID NO 42
<211> LENGTH: 20
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 42

Gly Arg Leu Ile Thr Val Asn Pro Ile Val Thr Glu Lys Asp Ser Pro
1               5                   10                  15

Val Asn Ile Glu
            20
```

```
<210> SEQ ID NO 43
<211> LENGTH: 20
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 43

Gly Arg Leu Ile Thr Ala Asn Pro Val Val Thr Lys Lys Glu Glu Pro
1               5                   10                  15

Val Asn Ile Glu
            20

<210> SEQ ID NO 44
<211> LENGTH: 20
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 44

Gly Arg Ile Ile Ser Ser Thr Pro Leu Ala Glu Asn Thr Asn Ser Val
1               5                   10                  15

Thr Asn Ile Glu
            20

<210> SEQ ID NO 45
<211> LENGTH: 60
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 45
ggcattctgg tgaccgtgaa cccgattgcg agcaccaacg atgatgaagt gctgattgaa      60

<210> SEQ ID NO 46
<211> LENGTH: 60
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 46
ggccgcctgg tgaccgtgaa cccgtttatt agcaccggcg cgcgaacaa caaagtgatg       60

<210> SEQ ID NO 47
<211> LENGTH: 60
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 47
ggccgcatgg tgaccgcgaa cccgtatgtg gcgagcagca ccgcgaacgc gaaagtgctg      60

<210> SEQ ID NO 48
<211> LENGTH: 60
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 48
ggccgcctgg tgaccgtgaa cccgtttgtg agcgtgagca ccgcgaacgc gaaagtgctg      60
```

```
<210> SEQ ID NO 49
<211> LENGTH: 60
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 49
ggccgcctgg tgaccgtgaa cccgtttgtg gcgaccagca gcgcgaacag caaagtgctg      60

<210> SEQ ID NO 50
<211> LENGTH: 60
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 50
ggccgcctga ttaccgcgaa cccgattgtg accgataaag aaaaaccggt gaacattgaa      60

<210> SEQ ID NO 51
<211> LENGTH: 60
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 51
ggccgcctga ttaccgtgaa cccgattgtg accgaaaaag atagcccggt gaacattgaa      60

<210> SEQ ID NO 52
<211> LENGTH: 60
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 52
ggccgcctga ttaccgcgaa cccggtggtg accaaaaaag aagaaccggt gaacattgaa      60

<210> SEQ ID NO 53
<211> LENGTH: 60
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 53
ggccgcatta ttagcagcac cccgctggcg gaaaacacca acagcgtgac caacattgaa      60

<210> SEQ ID NO 54
<211> LENGTH: 51
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 54
ggcagactgg tgaccgtgaa tccatttgtg tctgtggcca cagccaactc g               51

<210> SEQ ID NO 55
<211> LENGTH: 51
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 55
```
ggcagattgg tcactgtcaa ccctttttgtt tcagtggcca cggccaacgc t        51

```
<210> SEQ ID NO 56
<211> LENGTH: 37
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 56

Asn Glu Asp Gln Lys Ile Gly Ile Glu Ile Ile Lys Arg Ala Leu Lys
1               5                   10                  15

Ile Gly Ile Leu Val Thr Val Asn Pro Ile Ala Ser Thr Asn Asp Asp
            20                  25                  30

Glu Val Leu Ile Glu
        35

<210> SEQ ID NO 57
<211> LENGTH: 37
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 57

Asn Glu Asp Gln Lys Ile Gly Ile Glu Ile Ile Lys Arg Ala Leu Lys
1               5                   10                  15

Ile Gly Arg Leu Val Thr Val Asn Pro Phe Ile Ser Thr Gly Gly Ala
            20                  25                  30

Asn Asn Lys Val Met
        35

<210> SEQ ID NO 58
<211> LENGTH: 37
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 58

Asn Glu Asp Gln Lys Ile Gly Ile Glu Ile Ile Lys Arg Ala Leu Lys
1               5                   10                  15

Ile Gly Arg Met Val Thr Ala Asn Pro Tyr Val Ala Ser Ser Thr Ala
            20                  25                  30

Asn Ala Lys Val Leu
        35

<210> SEQ ID NO 59
<211> LENGTH: 37
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 59

Asn Glu Asp Gln Lys Ile Gly Ile Glu Ile Ile Lys Arg Ala Leu Lys
1               5                   10                  15

Ile Gly Arg Leu Val Thr Val Asn Pro Phe Val Ser Val Ser Thr Ala
            20                  25                  30

Asn Ala Lys Val Leu
        35
```

```
<210> SEQ ID NO 60
<211> LENGTH: 37
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 60

Asn Glu Asp Gln Lys Ile Gly Ile Glu Ile Ile Lys Arg Ala Leu Lys
1               5                   10                  15

Ile Gly Arg Leu Val Thr Val Asn Pro Phe Val Ala Thr Ser Ser Ala
            20                  25                  30

Asn Ser Lys Val Leu
        35

<210> SEQ ID NO 61
<211> LENGTH: 37
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 61

Asn Glu Asp Gln Lys Ile Gly Ile Glu Ile Ile Lys Arg Ala Leu Lys
1               5                   10                  15

Ile Gly Arg Leu Ile Thr Ala Asn Pro Ile Val Thr Asp Lys Glu Lys
            20                  25                  30

Pro Val Asn Ile Glu
        35

<210> SEQ ID NO 62
<211> LENGTH: 37
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 62

Asn Glu Asp Gln Lys Ile Gly Ile Glu Ile Ile Lys Arg Ala Leu Lys
1               5                   10                  15

Ile Gly Arg Leu Ile Thr Val Asn Pro Ile Val Thr Glu Lys Asp Ser
            20                  25                  30

Pro Val Asn Ile Glu
        35

<210> SEQ ID NO 63
<211> LENGTH: 37
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 63

Asn Glu Asp Gln Lys Ile Gly Ile Glu Ile Ile Lys Arg Ala Leu Lys
1               5                   10                  15

Ile Gly Arg Leu Ile Thr Ala Asn Pro Val Val Thr Lys Lys Glu Glu
            20                  25                  30

Pro Val Asn Ile Glu
        35

<210> SEQ ID NO 64
<211> LENGTH: 37
<212> TYPE: PRT
<213> ORGANISM: ARTIFICIAL SEQUENCE
```

```
<220> FEATURE:
<223> OTHER INFORMATION: SYNTHETIC PEPTIDE

<400> SEQUENCE: 64

Asn Glu Asp Gln Lys Ile Gly Ile Glu Ile Ile Lys Arg Ala Leu Lys
1               5                   10                  15

Ile Gly Arg Ile Ile Ser Ser Thr Pro Leu Ala Glu Asn Thr Asn Ser
            20                  25                  30

Val Thr Asn Ile Glu
        35

<210> SEQ ID NO 65
<211> LENGTH: 34
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 65

Asn Glu Asp Gln Lys Ile Gly Ile Glu Ile Ile Lys Arg Ala Leu Lys
1               5                   10                  15

Ile Gly Arg Leu Val Thr Val Asn Pro Phe Val Ser Val Ala Thr Ala
            20                  25                  30

Asn Ser

<210> SEQ ID NO 66
<211> LENGTH: 34
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 66

Asn Glu Asp Gln Lys Ile Gly Ile Glu Ile Ile Lys Arg Ala Leu Lys
1               5                   10                  15

Ile Gly Arg Leu Val Thr Val Asn Pro Phe Val Ser Val Ala Thr Ala
            20                  25                  30

Asn Ala

<210> SEQ ID NO 67
<211> LENGTH: 40
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 67

Lys Lys Ala Arg Val Glu Asp Ala Leu His Ala Thr Arg Ala Ala Val
1               5                   10                  15

Glu Glu Gly Val Gly Ile Leu Val Thr Val Asn Pro Ile Ala Ser Thr
            20                  25                  30

Asn Asp Asp Glu Val Leu Ile Glu
        35                  40

<210> SEQ ID NO 68
<211> LENGTH: 40
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 68

Lys Lys Ala Arg Val Glu Asp Ala Leu His Ala Thr Arg Ala Ala Val
```

```
                1               5                   10                  15
Glu Glu Gly Val Gly Arg Leu Val Thr Val Asn Pro Phe Ile Ser Thr
                20                  25                  30

Gly Gly Ala Asn Asn Lys Val Met
        35                  40

<210> SEQ ID NO 69
<211> LENGTH: 40
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 69

Lys Lys Ala Arg Val Glu Asp Ala Leu His Ala Thr Arg Ala Ala Val
1               5                   10                  15

Glu Glu Gly Val Gly Arg Met Val Thr Ala Asn Pro Tyr Val Ala Ser
                20                  25                  30

Ser Thr Ala Asn Ala Lys Val Leu
        35                  40

<210> SEQ ID NO 70
<211> LENGTH: 40
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 70

Lys Lys Ala Arg Val Glu Asp Ala Leu His Ala Thr Arg Ala Ala Val
1               5                   10                  15

Glu Glu Gly Val Gly Arg Leu Val Thr Val Asn Pro Phe Val Ser Val
                20                  25                  30

Ser Thr Ala Asn Ala Lys Val Leu
        35                  40

<210> SEQ ID NO 71
<211> LENGTH: 40
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 71

Lys Lys Ala Arg Val Glu Asp Ala Leu His Ala Thr Arg Ala Ala Val
1               5                   10                  15

Glu Glu Gly Val Gly Arg Leu Val Thr Val Asn Pro Phe Val Ala Thr
                20                  25                  30

Ser Ser Ala Asn Ser Lys Val Leu
        35                  40

<210> SEQ ID NO 72
<211> LENGTH: 40
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 72

Lys Lys Ala Arg Val Glu Asp Ala Leu His Ala Thr Arg Ala Ala Val
1               5                   10                  15

Glu Glu Gly Val Gly Arg Leu Ile Thr Ala Asn Pro Ile Val Thr Asp
                20                  25                  30
```

```
Lys Glu Lys Pro Val Asn Ile Glu
        35                  40

<210> SEQ ID NO 73
<211> LENGTH: 40
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 73

Lys Lys Ala Arg Val Glu Asp Ala Leu His Ala Thr Arg Ala Ala Val
1               5                   10                  15

Glu Glu Gly Val Gly Arg Leu Ile Thr Val Asn Pro Ile Val Thr Glu
                20                  25                  30

Lys Asp Ser Pro Val Asn Ile Glu
        35                  40

<210> SEQ ID NO 74
<211> LENGTH: 40
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 74

Lys Lys Ala Arg Val Glu Asp Ala Leu His Ala Thr Arg Ala Ala Val
1               5                   10                  15

Glu Glu Gly Val Gly Arg Leu Ile Thr Ala Asn Pro Val Val Thr Lys
                20                  25                  30

Lys Glu Glu Pro Val Asn Ile Glu
        35                  40

<210> SEQ ID NO 75
<211> LENGTH: 40
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 75

Lys Lys Ala Arg Val Glu Asp Ala Leu His Ala Thr Arg Ala Ala Val
1               5                   10                  15

Glu Glu Gly Val Gly Arg Ile Ile Ser Ser Thr Pro Leu Ala Glu Asn
                20                  25                  30

Thr Asn Ser Val Thr Asn Ile Glu
        35                  40

<210> SEQ ID NO 76
<211> LENGTH: 20
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 76

Lys Lys Ala Arg Val Glu Asp Ala Leu His Ala Thr Arg Ala Ala Val
1               5                   10                  15

Glu Glu Gly Val
                20

<210> SEQ ID NO 77
<211> LENGTH: 35
```

<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 77

Lys Lys Ala Arg Val Glu Asp Ala Leu His Ala Thr Arg Ala Ala Val
1               5                   10                  15

Glu Glu Gly Val Leu Val Thr Val Asn Pro Phe Val Ser Val Ala Thr
            20                  25                  30

Ala Asn Ser
        35

<210> SEQ ID NO 78
<211> LENGTH: 35
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 78

Lys Lys Ala Arg Val Glu Asp Ala Leu His Ala Thr Arg Ala Ala Val
1               5                   10                  15

Glu Glu Gly Val Leu Val Thr Val Asn Pro Phe Val Ser Val Ala Thr
            20                  25                  30

Ala Asn Ala
        35

<210> SEQ ID NO 79
<211> LENGTH: 37
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 79

Lys Lys Ala Arg Val Glu Asp Ala Leu His Ala Thr Arg Ala Ala Val
1               5                   10                  15

Glu Glu Gly Val Tyr Ile Val Val Gly Arg Gly Glu Gln Gln Ile Asn
            20                  25                  30

His His Trp His Lys
        35

<210> SEQ ID NO 80
<211> LENGTH: 31
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 80

Glu Gly Asp Glu Ala Thr Gly Ala Asn Ile Lys Val Ala Leu Glu Ala
1               5                   10                  15

Leu Val Thr Val Asn Pro Phe Val Ser Val Ala Thr Ala Asn Ser
            20                  25                  30

<210> SEQ ID NO 81
<211> LENGTH: 20
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 81

-continued

```
acgaagtggc cattttttgtc                                              20
```

<210> SEQ ID NO 82
<211> LENGTH: 20
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 82

```
ttgatgcaga gctccctctt                                               20
```

<210> SEQ ID NO 83
<211> LENGTH: 547
<212> TYPE: PRT
<213> ORGANISM: Escherichia coli

<400> SEQUENCE: 83

```
Ala Ala Lys Asp Val Lys Phe Gly Asn Asp Ala Arg Val Lys Met Leu
1               5                   10                  15

Arg Gly Val Asn Val Leu Ala Asp Ala Val Lys Val Thr Leu Gly Pro
            20                  25                  30

Lys Gly Arg Asn Val Val Leu Asp Lys Ser Phe Gly Ala Pro Thr Ile
        35                  40                  45

Thr Lys Asp Gly Val Ser Val Ala Arg Glu Ile Glu Leu Glu Asp Lys
    50                  55                  60

Phe Glu Asn Met Gly Ala Gln Met Val Lys Glu Val Ala Ser Lys Ala
65                  70                  75                  80

Asn Asp Ala Ala Gly Asp Gly Thr Thr Thr Ala Thr Val Leu Ala Gln
                85                  90                  95

Ala Ile Ile Thr Glu Gly Leu Lys Ala Val Ala Ala Gly Met Asn Pro
            100                 105                 110

Met Asp Leu Lys Arg Gly Ile Asp Lys Ala Val Thr Val Ala Val Glu
        115                 120                 125

Glu Leu Lys Ala Leu Ser Val Pro Cys Ser Asp Ser Lys Ala Ile Ala
    130                 135                 140

Gln Val Gly Thr Ile Ser Ala Asn Ser Asp Glu Thr Val Gly Lys Leu
145                 150                 155                 160

Ile Ala Glu Ala Met Asp Lys Val Gly Lys Glu Gly Val Ile Thr Val
                165                 170                 175

Glu Asp Gly Thr Gly Leu Gln Asp Glu Leu Asp Val Val Glu Gly Met
            180                 185                 190

Gln Phe Asp Arg Gly Tyr Leu Ser Pro Tyr Phe Ile Asn Lys Pro Glu
        195                 200                 205

Thr Gly Ala Val Glu Leu Glu Ser Pro Phe Ile Leu Leu Ala Asp Lys
    210                 215                 220

Lys Ile Ser Asn Ile Arg Glu Met Leu Pro Val Leu Glu Ala Val Ala
225                 230                 235                 240

Lys Ala Gly Lys Pro Leu Leu Ile Ile Ala Glu Asp Val Glu Gly Glu
                245                 250                 255

Ala Leu Ala Thr Leu Val Val Asn Thr Met Arg Gly Ile Val Lys Val
            260                 265                 270

Ala Ala Val Lys Ala Pro Gly Phe Gly Asp Arg Arg Lys Ala Met Leu
        275                 280                 285

Gln Asp Ile Ala Thr Leu Thr Gly Gly Thr Val Ile Ser Glu Glu Ile
    290                 295                 300

Gly Met Glu Leu Glu Lys Ala Thr Leu Glu Asp Leu Gly Gln Ala Lys
```

```
                305                 310                 315                 320
Arg Val Val Ile Asn Lys Asp Thr Thr Thr Ile Ile Asp Gly Val Gly
                    325                 330                 335

Glu Glu Ala Ala Ile Gln Gly Arg Val Ala Gln Ile Arg Gln Gln Ile
                340                 345                 350

Glu Glu Ala Thr Ser Asp Tyr Asp Arg Glu Lys Leu Gln Glu Arg Val
            355                 360                 365

Ala Lys Leu Ala Gly Gly Val Ala Val Ile Lys Val Gly Ala Ala Thr
        370                 375                 380

Glu Val Glu Met Lys Glu Lys Lys Ala Arg Val Glu Asp Ala Leu His
385                 390                 395                 400

Ala Thr Arg Ala Ala Val Glu Glu Gly Val Val Ala Gly Gly Gly Val
                405                 410                 415

Ala Leu Ile Arg Val Ala Ser Lys Leu Ala Asp Leu Arg Gly Gln Asn
                    420                 425                 430

Glu Asp Gln Asn Val Gly Ile Lys Val Ala Leu Arg Ala Met Glu Ala
                435                 440                 445

Pro Leu Arg Gln Ile Val Leu Asn Cys Gly Glu Glu Pro Ser Val Val
    450                 455                 460

Ala Asn Thr Val Lys Gly Gly Asp Gly Asn Tyr Gly Tyr Asn Ala Ala
465                 470                 475                 480

Thr Glu Glu Tyr Gly Asn Met Ile Asp Met Gly Ile Leu Asp Pro Thr
                485                 490                 495

Lys Val Thr Arg Ser Ala Leu Gln Tyr Ala Ala Ser Val Ala Gly Leu
            500                 505                 510

Met Ile Thr Thr Glu Cys Met Val Thr Asp Leu Pro Lys Asn Asp Ala
        515                 520                 525

Ala Asp Leu Gly Ala Ala Gly Gly Met Gly Gly Met Gly Gly Met Gly
    530                 535                 540

Gly Met Met
545

<210> SEQ ID NO 84
<211> LENGTH: 13
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 84

Val Ile Val Glu Leu Ile Pro Ser Thr Ser Ser Ala Val
1               5                   10

<210> SEQ ID NO 85
<211> LENGTH: 21
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 85

Met Glu Val Gly Trp Tyr Arg Ser Pro Phe Ser Arg Val Val His Leu
1               5                   10                  15

Tyr Arg Asn Gly Lys
            20

<210> SEQ ID NO 86
<211> LENGTH: 20
<212> TYPE: PRT
```

-continued

```
<213> ORGANISM: ARTIFICIAL SEQUENCE
<220> FEATURE:
<223> OTHER INFORMATION: SYNTHETIC PEPTIDE

<400> SEQUENCE: 86

Lys Lys Asp Arg Val Thr Asp Ala Leu Asn Ala Thr Arg Ala Ala Val
1               5                   10                  15

Glu Glu Gly Ile
            20

<210> SEQ ID NO 87
<211> LENGTH: 17
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 87

Glu Gly Asp Ile Glu Thr Gly Val Asn Ile Val Leu Lys Ala Leu Thr
1               5                   10                  15

Ala
```

COMPOSITIONS OF HSP60 PEPTIDES AND VIRAL ANTIGENS FOR VACCINATION AND DIAGNOSIS

CROSS REFERENCE TO RELATED APPLICATIONS

This application is a divisional of U.S. patent application Ser. No. 11/908,474, filed May 15, 2008, which is U.S. national stage of PCT/IL2006/000222, filed Feb. 21, 2006, which is based on and claims the benefit of U.S. Provisional Patent Application No. 60/661,017, filed Mar. 14, 2005, the contents of each of which is expressly incorporated herein in its entirety by this reference.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 32,493 byte ASCII (text) file named "Seq_List" created on Jun. 20, 2011.

FIELD OF THE INVENTION

The present invention relates to vaccines providing enhanced immunogenicity comprising HSP60 peptides conjugated to or mixed with a viral antigen. The present invention further identifies certain novel epitopes, compositions thereof and methods of using same for vaccination or diagnosis.

BACKGROUND OF THE INVENTION

Despite remarkable achievements in the development of vaccines for certain viral infections (i.e., polio and measles), and the eradication of specific viruses from the human population (e.g., smallpox), viral diseases remain as important medical and public health problems. Indeed, viruses are responsible for several "emerging" (or re-emerging) diseases (e.g., West Nile encephalitis and Dengue fever), and viral infection is a cause of significant morbidity and mortality worldwide.

The presence of adequate T-cell help is important for the construction of potent vaccines. Vaccines that induce both helper T cells and CTLs may be more effective that those that induce CTLs only. Indeed, the importance of cooperation between $CD4^+$ and $CD8^+$ T cells is emphasized in the therapeutic vaccination against chronic viral infection (Zajac et al., 1998; Matloubian et al., 1994).

Classically, vaccines are manufactured by introducing killed or attenuated organisms into the host along with suitable adjuvants to initiate the normal immune response to the organisms while, desirably, avoiding the pathogenic effects of the organism in the host. The approach suffers from the well known limitations in that it is rarely possible to avoid the pathogenic response because of the complexity of the vaccine which includes not only the antigenic determinant of interest but many related and unrelated deleterious materials, any number of which may, in some or all individuals, induce an undesirable reaction in the host.

For example, vaccines produced in the classical way may include competing antigens which are detrimental to the desired immune response, antigens which include unrelated immune responses, nucleic acids from the organism or culture, endotoxins and constituents of unknown composition and source. These vaccines, generated from complex materials, inherently have a relatively high probability of inducing competing responses even from the antigen of interest.

HSP60 belongs to a family of chaperone molecules highly conserved throughout evolution; a similar HSP60 molecule is present in all cells, prokaryotes and eukaryotes. The human HSP60 molecule was formerly designated HSP65, but is now designated HSP60 in view of more accurate molecular weight information; by either designation, the protein is the same. Apparently, no cell can exist without the ability to express HSP60. Mammalian HSP60 is highly homologous to the bacterial cognates, showing about 50% amino acid identity (Jindal et al., 1989). Thus, HSP60 is shared by the host and its parasites, and is immunogenic, cross-reactive, and universally expressed in inflammation. Furthermore, HSP60 is well recognized by the immune system (Konen Waisman et al., 1999, Konen Waisman et al., 1995) and is a part of the set of self-molecules for which autoimmunity naturally exists; HSP60 is member of the immunologic homunculus (Cohen, 1992). Heat shock, IFNγ, bacterial or viral infection, and inflammation, all result in the presentation of endogenous HSP60 epitopes on MHC class II molecules leading to the activation of HSP60-specific T cells, even in healthy individuals (Anderton et al., 1993; Hermann et al., 1991; Koga et al., 1989).

European Patent EP 262 710 and U.S. Pat. No. 5,154,923 describe peptides having an amino acid sequence corresponding to positions 171-240 and 172-192, respectively, of a *Mycobacterium boris* BCG 64 kD polypeptide, that are useful as immunogens inducing resistance to autoimmune arthritis and similar autoimmune diseases.

PCT Patent Application No. WO 90/10449 describes a peptide designated p277 having an amino acid sequence corresponding to positions 437-460 of the human HSP65 molecule that is useful as immunogen inducing resistance to insulin dependent diabetes mellitus (IDDM). A control peptide, designated p278, corresponding to positions 458-474 of human HSP65, did not induce resistance to IDDM.

Lussow et al. (1990) showed that the priming of mice with live *Mycobacterium tuberculosis* var. *Bovis* (BCG) and immunization with the repetitive malaria synthetic peptide $(NANP)_{40}$ conjugated to purified protein derivative (PPD), led to the induction of high and long-lasting titers of anti-peptide IgG antibodies. Later on, Lussow et al. (1991) showed that mycobacterial heat-shock proteins (HSP) of 65 kDa (GroEL-type) and 70 kDa (DnaK-type) acted as carrier molecules in mice, previously primed with *Mycobacterium tuberculosis* var. *boris* (bacillus Calmette-Guerin, BCG), for the induction of high and long-lasting titers of IgG against the repetitive malaria synthetic peptide $(NANP)_{40}$. Anti-peptide antibodies were induced when the malaria peptide, conjugated to the mycobacterial HSP, was given in the absence of any adjuvants.

Barrios et al. (1992) have shown that mice immunized with peptides or oligosaccharides conjugated to the 70 kDa HSP produced high titers of IgG antibodies in the absence of any previous priming with BCG. The anti-peptide antibody response persisted for at least 1 year. This adjuvant-free carrier effect of the 70 kDa HSP was T cell dependent, since no anti-peptide nor anti-70 kDa IgG antibodies were induced in athymic nu/nu mice. Previous immunization of mice with the 65 kDa or 70 kDa HSP did not have any negative effect on the induction of anti-peptide IgG antibodies after immunization with HSP-peptide conjugates in the absence of adjuvants. Furthermore, preimmunization with the 65 kDa HSP could substitute for BCG in providing effective priming for the induction of anti-$(NANP)_{40}$ antibodies. Finally, both the 65 kDa and 70 kDa HSP acted as carrier molecules for the induction of IgG antibodies to group C meningococcal oligosaccharides, in the absence of adjuvants, suggesting that the use of HSPs as carriers in conjugated constructs for the induction of anti-peptide and anti-oligosaccharide antibodies could be of value in the design of new vaccines for eventual use in humans.

U.S. Pat. No. 5,736,146 discloses conjugates of poorly immunogenic antigens with a synthetic peptide carrier comprising a T cell epitope derived from the sequence of human heat shock protein HSP65, or an analog thereof, said peptide or analog being capable of increasing substantially the immunogenicity of the poorly immunogenic antigen. The '146 patent discloses conjugates of a peptide corresponding to positions 458-474 and 437-453 of human or mouse HSP60 and homologs thereof with a wide variety of antigens including peptides, proteins and polysaccharides such as bacterial polysaccharide (e.g. capsular polysaccharide (CPS) Vi of *Salmonella typhi*), and antigens derived from HIV virus or from malaria antigen.

U.S. Pat. No. 5,869,058 discloses conjugates of poorly immunogenic antigens, e.g., peptides, proteins and polysaccharides, with a synthetic peptide carrier comprising a T cell epitope derived from the sequence of *E. coli* HSP65 (GroEL), or an analog thereof, said peptide or analog being capable of increasing substantially the immunogenicity of the poorly immunogenic antigen. A suitable peptide according to the invention is Pep278e, which corresponds to positions 437-453 of the *E. coli* HSP65 molecule.

Human cytomegalovirus (HCMV) is a ubiquitous double-stranded DNA virus from the betaherpesvirus group; it is endemic in all human populations. In North America, HCMV infects about 50% of the population outside of urban centers and up to 90% of the population within cities. HCMV disease presents two major medical problems: first, it is the most common congenital viral infection, causing birth defects including mal-development of the central nervous system; up to 25% of asymptomatic infected infants will develop neurologic sequelae. Second, HCMV becomes re-activated in immunocompromised patients.

A self-limiting acute phase of viral infection, persistent and latent phases normally characterize the pathogenesis of HCMV infection in the immunocompetent host. The clinical outcome of HCMV infection is determined by the ability of infected individuals to mount protective humoral and T-cell mediated immune responses. In immunocompromised hosts, including persons with HIV infection, cancer patients and allograft recipients, primary HCMV infection or reactivation of a latent virus results in multi-organ HCMV disease, associated with high rates of morbidity and mortality. These grave clinical consequences emphasize the need for effective HCMV vaccines to prevent not only primary infection but also to limit or prevent reactivation.

At present there is no protective vaccine available for CMV. Currently available antiviral drugs which target viral DNA replication are efficacious but exhibit significant host toxicity and a high spontaneous resistance rate.

West Nile virus is a member of the alpha-like Flaviviridae. The Flavivirus genome is a single-stranded, positive-sense RNA approximately 11 kb in length, containing a 5' untranslated region (5'UTR); a coding region encoding the three viral structural proteins; seven nonstructural proteins, designated NS1, NS2A, NS2B, NS3, NS4A, NS4B, NS5; and a 3' untranslated region (3'UTR). The viral structural proteins include the capsid (C), premembrane/membrane (prM) and envelope (E) proteins. The structural and nonstructural proteins are translated as a single polyprotein. The polyprotein is then processed by cellular and viral proteases.

West Nile virus affects birds as well as reptiles and mammals, together with man. The West Nile virus is transmitted to birds and mammals by the bites of certain mosquitoes (e.g. Culex, Aedes, Anopheles). Direct transmission may happen from WNV infected subject to healthy subject by oral transmission (prey and transmission through colostrum) and blood/organ vectored transmission. Widespread in Africa, the geographic range of WNV now also includes Australia, Europe, the Middle East, West Asia and the USA. West Nile virus can cause a harsh, self-limiting fever, body aches, brain swelling, coma, paralysis, and death.

There is no effective treatment for the disease. A number of different WNV vaccines are now in various stages of development and testing (Monath, 2001; Pletnev et al., 2003; Tesh et al., 2002; Hall et al., 2003), but presently a licensed human vaccine is not available for its prevention. The only currently effective way to provide immediate resistance to WNV is by passive administration of protective antibodies (Casadevall, 2002). Mosquito control is currently considered the practical strategy to combat the spread of disease, but effective spraying is difficult to perform in urban areas. Clearly, an effective vaccine is needed to protect at-risk populations.

There remains a need for improved vaccines conferring protection against viral infections, using isolated epitopes. Furthermore, isolated epitopes are needed for improved diagnostic tests.

SUMMARY OF THE INVENTION

The present invention provides compositions and methods suitable for vaccination against and diagnosis of viral infections. According to some aspects the present invention provides a vaccine comprising an isolated viral antigenic peptide and a peptide comprising a T cell epitope of HSP60, wherein the HSP60 peptide enhances the immunogenicity of the viral antigenic peptide by at least two fold compared to the peptide without the HSP60 peptide. In certain currently preferred embodiments the immunogenicity is enhanced by at least 4-5 fold. Novel viral peptide antigens useful in vaccination and diagnosis are also provided.

In certain embodiments the vaccine compositions comprise a T cell epitope of HSP60 suitable to enhance the immunogenicity when used as an adjuvant peptide that is mixed with the viral antigen. In alternative embodiments the vaccine comprises a T cell epitope of HSP60 suitable to enhance the immunogenicity of the viral antigenic peptide when used in conjugates where the HSP60 peptide is covalently linked to the viral antigenic peptide.

The enhanced immunogenicity of said viral antigen is measured by at least one of the following: serum titer of antibodies directed to said viral antigen; T cell proliferation in the presence of said viral antigen; cytokine secretion induced by said viral antigen; specific T cell mediated lysis of virus-infected cells; and reduction of detectable viral load.

According to another aspect, the invention provides conjugates comprising a viral antigen covalently attached to a synthetic peptide carrier comprising a T cell epitope of HSP60. According to some embodiments, the synthetic peptide carrier is the known peptide carrier p458, a Major Histocompatibility Complex (MHC) class II-restricted peptide derived from murine HSP60 (aa 458-474, also designated previously as p278m), or an analog or derivative thereof. In other embodiments, the synthetic peptide carrier is Ec27, a novel peptide derived from *E. coli* HSP60 (GroEL, aa 391-410).

According to the present invention, it is now disclosed that conjugates comprising a synthetic peptide carrier selected from p458 and Ec27 covalently attached to a viral antigen are unexpectedly effective in conferring immunity against viral infections. It is now demonstrated for the first time that these conjugates significantly enhance effective immunity against both DNA and RNA viruses, latent and acute infections, and when combined with CTL-, B cell- and MHC II-restricted viral epitopes.

The principles of the invention are exemplified by two model systems for viral infections. Mouse Cytomegalovirus (MCMV) infection in mice is an established model system for examining human infection with Human Cytomegalovirus (HCMV), a DNA virus which is characterized by a latent infection following a self-limiting acute phase of viral infection. West Nile virus (WNV) infection in mice serves as a model for the acute viral infection of WNV in humans.

According to a some embodiments, the present invention provides a conjugate comprising a viral antigen covalently attached to a synthetic peptide carrier comprising a T cell epitope of HSP60 in which said synthetic peptide carrier is selected from the group of peptides consisting of:
(a) NEDQKIGIEIIKRTLKI (p458h; SEQ ID NO: 1),
(b) NEDQKIGIEIIKRALKI (p458; SEQ ID NO:2),
(c) EGDEATGANIVKVALEA (p458mt; SEQ ID NO:3),
(d) NEDQNVGIKVALRAMEA (p458e; SEQ ID NO:4),
(e) an analog of p458h (SEQ ID NO: 1) that has at least 70% of the electric and hydrophilicity/hydrophobicity characteristic of human HSP60 from position 458 to position 474, said peptide or analog being capable of increasing substantially the immunogenicity of the viral antigen when the conjugate is administered in vivo, and derivatives thereof,
(f) KKARVEDALHATRAAVEEGV (Ec27; SEQ ID NO:76) and analogs, fragments and derivatives thereof.

In one embodiment, the synthetic peptide is an analog of p458h (SEQ ID NO: 1): $^{458}$NEDQKIGIEIIKRTLKI$^{474}$ in which the residue $E^{459}$ is either E or D; the residue $D^{460}$ is either D or E; the residue $K^{462}$ is either K or R or ornithine (Orn); the residue $I^{463}$ is either I or L, V, M, F, norleucine (Nle) or norvaline (Nva); the residue $I^{465}$ residue is either I or L, V, M, F, Nle or Nva; the residue $E^{466}$ is either E or D; the residue 1467 is either I or L, V, M, F, Nle or Nva; the residue $I^{468}$ is either I or L, V, M, F, Nle or Nva; the residue $K^{469}$ is either K or R or Orn; the residue $R^{470}$ is either R, K or Orn; the residue $L^{472}$ in either L or I, V, M, F, Nle or Nva; the residue $K^{473}$ is either K or R or Orn; and the residue $I^{474}$ is either I or L, V, M, F, Nle or Nva.

In another aspect, there is provided a novel adjuvant peptide derived from E. coli HSP60 (GroEL) protein, useful for the compositions and methods of the invention. The novel adjuvant peptide, herein designated Ec27, has an amino acid sequence corresponding to positions 391-410 of GroEL (corresponding to accession number gi:45686198 without the first methionine residue, SEQ ID NO:83), as follows: KKARVEDALHATRAAVEEGV (SEQ ID NO:76). It is to be explicitly understood that the corresponding peptides from mammalian species are included within the scope of the present invention. The corresponding human peptide exhibits 80% homology, having the sequence set forth in SEQ ID NO:86, as follows: KKDRVTDALNATRAAVEEGI (Ec27h). Ec27 analogs, fragments, derivatives, conjugates and salts are also contemplated by the present invention.

The Ec27 peptide is now demonstrated for the first time to increase significantly the immunogenicity of a broad array of antigens, including but not limited to viral antigens, bacterial antigens and mammalian antigens, e.g., viral peptide antigens, bacterial polysaccharides and antibodies. Surprisingly Ec27 was found to increase the immunogenicity of antigens when covalently conjugated to the antigen, as well as when mixed with the antigen. Unexpectedly, Ec27 could even further increase the immunogenicity of antigens of the invention conjugated to the p458 carriers.

In another embodiment, the invention further provides vaccine compositions comprising an antigen and a peptide adjuvant having an amino acid sequence as set forth in SEQ ID NO:76 or an analog, fragment or derivative thereof. In various embodiments, the antigen is selected from the group consisting of: a peptide, a peptide derivative, a protein, a polysaccharide (e.g. a bacterial polysaccharide), and an antibody. In one embodiment, the vaccine composition comprises a conjugate of the peptide adjuvant and said antigen. In alternate embodiments, said vaccine composition comprises an admixture of said peptide adjuvant and said antigen.

In another aspect, the viral antigen used in the conjugates and compositions of the invention comprises at least one epitope selected from: a CTL epitope (a MHC I restricted T cell epitope), a B cell epitope and a MHC II restricted T cell epitope.

The viral antigen used in the conjugates of the invention may be derived from any virus of interest. In certain embodiments, the virus belongs to the herpesviridae family. In other particular embodiments, the virus belongs to the betaherpesvirus subfamily. In one particular embodiment, the viral antigen is derived from immediate early gene 1 (IE-1) protein of a virus belonging to herpesviridae. In another particular embodiment, the viral antigen comprises a CTL epitope. In another particular embodiment, the virus is CMV. In one preferred embodiment, the viral antigen is derived from immediate early gene 1 (IE-1) protein of CMV. In another preferred embodiment, the viral antigen comprises a CTL epitope.

In other embodiments, the virus belongs to the Flaviviridae family. In other particular embodiments, the virus belongs to the flavivirus genus. According to various particular embodiments, the virus is selected from the group consisting of: West Nile virus (WNV), Yellow fever virus, St. Louis encephalitis virus, Murray Valley encephalitis virus, Kunjin virus, Japanese encephalitis virus, Dengue virus type 1, Dengue virus type 2, Dengue virus type 3 and Dengue virus type 4. In one particular embodiment, the viral antigen is derived from West Nile Virus (WNV).

In one preferred embodiment, the viral antigen is derived from the envelope (E) protein of a virus belonging to the flaviviridae family. In another preferred embodiment, the viral antigen is derived from the E3 domain of said protein. In another preferred embodiment, said viral antigen comprises a B cell epitope and a MHC II restricted epitope. In another preferred embodiment, the viral antigen is derived from the WNV envelope (E) protein. In another preferred embodiment, the viral antigen is derived from the E3 domain of said protein. In another preferred embodiment, said viral antigen comprises a B cell epitope and a MHC II restricted epitope.

Other embodiments of the present invention are directed to novel isolated viral peptide antigens that may be used in conjugation with the carriers of the invention for anti viral vaccination, as well as for diagnostic purposes, as specified herein.

In another aspect, there is provided a novel peptide antigen derived from WNV E3 domain of E protein, hereby designated p15, having an amino acid sequence corresponding to positions 355-369 of the E protein. Depending on the particular strain of WNV, this novel antigen has an amino acid sequence selected from the group consisting of: LVTVNPFVSVATANS (SEQ ID NO:11) and LVTVNPFVSVATANA (SEQ ID NO:12). Other embodiments are directed to analogs, homologs, fragments and derivatives thereof. In other embodiments, the invention provides proteins, peptides and conjugates comprising said antigen. In one particular embodiment, the peptide has an amino acid sequence as set forth in any one of SEQ ID NOS:34-35 (see Table 1).

In other embodiments, there is provided a p15 homologous peptide antigen derived from the E3 domain of the envelope protein of a flavivirus selected from the group consisting of: West Nile virus (WNV), Yellow fever virus, St. Louis encephalitis virus, Murray Valley encephalitis virus, Kunjin virus, Japanese encephalitis virus, Dengue virus type 1, Dengue virus type 2, Dengue virus type 3 and Dengue virus type 4. In certain particular embodiments, the p15 homologous antigen has an amino acid sequence as set forth in any one of SEQ ID NOS:25-33 and 36-44 (see Table 1), and analogs, homologs, fragments, and derivatives thereof.

In another aspect, there is provided a second novel WNV peptide antigen derived from the E protein, herein denoted p17, having the following amino acid sequence: YIV-VGRGEQQINHHWHK (SEQ ID NO:21). Other embodiments are directed to analogs, homologs, fragments, and derivatives thereof.

In other embodiments, the invention provides nucleic acid molecules encoding said novel peptide antigens, recombinant constructs comprising these nucleic acid molecules, and vectors and cells comprising them.

In another embodiment, there are provided conjugates comprising a synthetic peptide carrier of the invention and a viral antigen having an amino acid sequence as set forth in any one of SEQ ID NOS:11-12 and 34-35 and analogs, homologs, fragments and derivatives thereof covalently attached to a synthetic peptide carrier of the invention. In another embodiment, the conjugate has an amino acid sequence as set forth in any one of SEQ ID NOS:13-16, 65-66 and 77-78. In other embodiments, the conjugates of the invention comprise a viral antigen having an amino acid sequence as set forth in any one of SEQ ID NOS:25-33 and 36-44 covalently attached to a synthetic peptide carrier of the invention. In another embodiment, the conjugate has an amino acid sequence as set forth in any one of SEQ ID NOS:56-64, and 67-75. In other embodiments, the conjugates of the invention comprise a viral antigen having an amino acid sequence as set forth in SEQ ID NO:21 covalently attached to a synthetic peptide carrier of the invention. In another embodiment, the conjugate has an amino acid sequence as set forth in any one of SEQ ID NOS:23-24 and 79 (see Table 4).

In another aspect, the invention provides vaccine compositions comprising the conjugates of the invention and a pharmaceutically acceptable carrier, adjuvant, excipient or diluent. In another aspect, the invention provides vaccine compositions comprising a viral antigen in admixture with Ec27 and a pharmaceutically acceptable carrier, adjuvant, excipient or diluent. In another aspect, the invention provides vaccine compositions comprising the novel isolated viral peptide antigens of the invention and a pharmaceutically acceptable carrier, adjuvant, excipient or diluent.

In yet another aspect, the invention provides methods for increasing the immunogenicity of a viral antigen which comprises linking the antigen to a synthetic peptide carrier of the invention.

In another aspect, the invention provides methods for immunizing a subject in need thereof against a viral infection, comprising administering to the subject an effective amount of a vaccine composition comprising a conjugate of the invention and a pharmaceutically acceptable carrier, adjuvant, excipient or diluent.

The vaccine composition may be administered to said subject before the exposure of said subject to the virus or after exposure of said subject to said virus.

In another aspect, the invention provides methods comprising:
(a) isolating a viral antigen, comprising at least one epitope selected from: a CTL epitope, a B cell epitope and a MHC II-restricted epitope;
(b) conjugating said viral antigen to a synthetic peptide carrier of the invention to form a peptide-carrier conjugate; and
(c) administering to the subject an effective amount of a vaccine composition comprising the conjugate and a pharmaceutically acceptable carrier, adjuvant, excipient or diluent.

According to various embodiments, the compositions and methods of the invention are suitable for vaccinating a subject selected from a group consisting of: humans, non-human mammals and non-mammalian animals. In a preferred embodiment, the subject is human.

Other aspects of the present invention are directed to diagnostic kits and methods utilizing the novel isolated viral peptide antigens for determining the exposure of a subject to a flavivirus.

In one aspect, there is provided a diagnostic kit comprising at least one viral peptide antigen of the invention and means for detecting whether the peptide antigen is bound specifically to a suitable biological sample.

In another aspect, the invention provides methods for diagnosing exposure of a subject to a flavivirus and for diagnosing a flavivirus infection in a subject, comprising the steps of:
(a) contacting a suitable biological sample with a viral antigen having an amino acid sequence as set forth in any one of SEQ ID NOS:11-12, 25-44 and 21 and analogs, homologs, derivatives and salts thereof under conditions such that an immune reaction can occur;
(b) determining the extent of specific antigen binding to the biological sample,
wherein a level significantly higher than the level obtained for a sample obtained from a non-infected subject is indicative of exposure of the subject to the flavivirus.

In certain embodiments, the kits and diagnostic methods of the invention are useful for the differential diagnosis of a flavivirus infection.

These and other embodiments of the present invention will become apparent in conjunction with the figures, description and claims that follow.

BRIEF DESCRIPTION OF THE DRAWINGS

FIG. 15. Viral loads following p32 immunization and WNV challenge.

FIG. 16. proliferation and IFN-γ secretion of splenocytes from mice immunized by Ec27-p15 conjugates following in vitro stimulation with p15.

DETAILED DESCRIPTION OF THE INVENTION

Figure 1A:
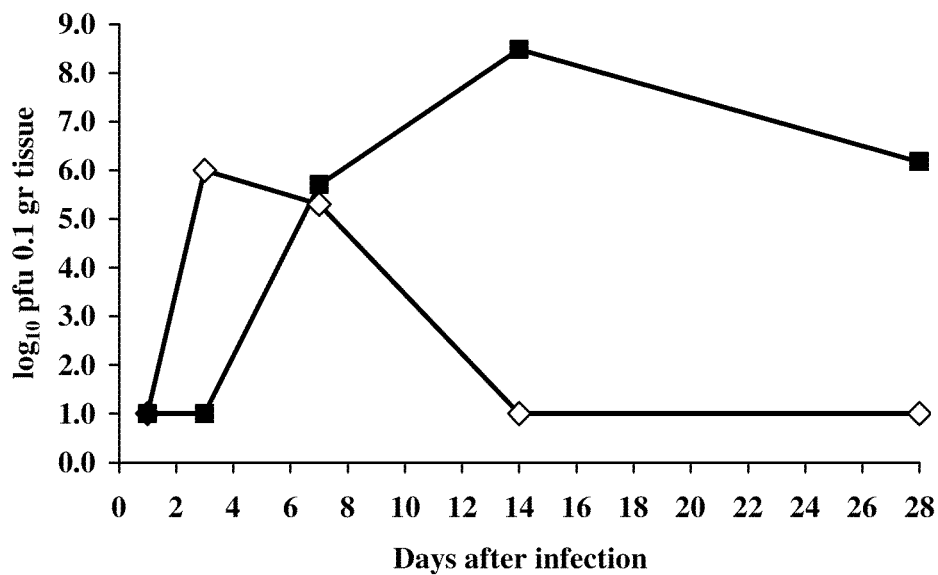
FIG. 1. Kinetics of MCMV infection in spleen and salivary gland (SG) of BALB/c mice. Mice were challenged i.p. with $5 \times 10^4$ pfu of MCMV. A. Infectious virus titers in spleen and salivary gland were measured at different time points after infection (calculated as log 10 pfu/0.1 g tissue). The data represent the average of 5 experiments. B. PCR amplification of the 356 bp product of MCMV gB DNA in spleen and salivary gland at different time points after infection. Results are from 1 representative experiment of 3 performed.

The present invention provides novel conjugates comprising a viral antigen covalently linked to a synthetic peptide carrier comprising a T cell epitope of HSP60. The synthetic peptide carrier, p458, is a MHC class II-restricted peptide derived from murine HSP60 (aa 458-474, also designated previously as p278m), or an analog or derivative thereof, which peptide or analog being capable of increasing substantially the immunogenicity of the viral antigen. In other embodiments, the carrier is Ec27, a novel peptide derived from *E. coli* GroEL (aa 391-410). The invention provides vaccine compositions comprising the conjugates of the invention, and methods for their use in vaccinating a subject in need thereof against a viral infection. The invention further provides novel viral peptide antigens, conjugates and vaccine compositions thereof and uses thereof in vaccination and diagnosis.

The present invention discloses unexpectedly that a vaccine composition comprising a conjugate of a viral antigen and a peptide carrier derived from HSP60 p458 or Ec27 is highly efficacious in conferring protective immunity against a viral infection in vivo. It is now demonstrated for the first time that p458 and Ec27 enhance effective immunity even for conjugates comprising antigens that are not poorly immunogenic. The peptide carriers of the invention were found to enhance the immunogenicity of the viral antigen by at least two fold compared to the peptide without the HSP60 peptide.

The present invention is based, in part, on studies of p458-viral antigen conjugate vaccination for the treatment of a chronic (latent) Cytomegalovirus (CMV) infection associated with persistence of virus in the salivary glands. A conjugate comprising 89pep, an antigen derived from murine CMV (MCMV) immediate early gene 1 protein (IE-1), fused to p458, was more effective than the 89pep in inducing 89pep-specific IFNγ secretion and specific CTL activity. The p458-89pep chimeric peptide induced sustained IFNγ secretion in the salivary gland specific to 89pep and only this immunization was associated with clearance of virus from the salivary gland.

The present invention is also based, in part, on studies of p458-viral antigen and Ec27-viral antigen conjugate vaccination against an acute viral infection of West Nile Virus (WNV). A conjugate comprising p15, a novel antigen derived from WNV envelope (E) protein, fused to p458 was capable, upon immunization, to significantly reduce the mortality associated with the infection, while immunization with p15 alone could only moderately affect the mortality rate. The conjugate was more effective than the viral antigen alone in inducing WNV-specific neutralizing antibodies as well as WNV-specific T cell proliferation and IFNγ secretion. Ec27-p15 conjugate was also more effective than p15 alone in inducing p15-specific T cell proliferation and IFNγ secretion.

Thus, the conjugates of the invention are herein demonstrated to be effective against both DNA and RNA viruses, latent and acute infections, and when combined with CTL-, B cell- and MHC II-restricted viral epitopes.

Ec27, a novel adjuvant peptide derived from *E. coli* HSP60 (GroEL) protein, was found to increase significantly the immunogenicity of a broad array of antigens, including but not limited to viral antigens, bacterial antigens and mammalian antigens, e.g., viral peptide antigens, bacterial polysaccharides and antibodies. Surprisingly Ec27 was found to increase the immunogenicity of antigens when covalently conjugated to the antigen, as well as when mixed with the antigen. Unexpectedly, Ec27 could even further increase the immunogenicity of antigens conjugated to the p458 carriers. Ec27 has an amino acid sequence corresponding to positions 391-410 of GroEL (corresponding to accession number gi:45686198 without the first methionine residue, SEQ ID NO:83), as follows: KKARVEDALHATRAAVEEGV (SEQ ID NO:76).

According to a first aspect, the present invention provides a conjugate comprising a viral antigen covalently attached to a synthetic peptide carrier comprising a T cell epitope of HSP60 in which said synthetic peptide carrier is selected from the group of peptides consisting of:

(a) NEDQKIGIEIIKRTLKI (p458h, derived from human HSP60; SEQ ID NO: 1),
(b) NEDQKIGIEIIKRALKI (p458, derived from mouse HSP60; SEQ ID NO:2),
(c) EGDEATGANIVKVALEA (p458mt, derived from *M. tuberculosis* HSP60; SEQ ID NO:3),
(d) NEDQNVGIKVALRAMEA (p458e, derived from *E. coli* HSP60; SEQ ID NO:4. It should be noted, that the amino acid sequence of p458e corresponds to positions 432-448 of SEQ ID NO:83)
(e) an analog of p458h (SEQ ID NO: 1) that has at least 70% of the electric and hydrophilicity/hydrophobicity characteristic of human HSP60 from position 458 to position 474, said peptide or analog being capable of increasing substantially the immunogenicity of the viral antigen when the conjugate is administered in vivo,
(f) KKARVEDALHATRAAVEEGV (Ec27, derived from *E. coli* HSP60; SEQ ID NO:76).

The active peptide carriers according to the invention are characterized as being highly charged, i.e. of strong electric properties (7 out of 17 constituent amino acid residues of p458 are either negatively or positively charged) and highly hydrophobic (6 amino acid residues). The peptide p458h is further characterized as possessing a polar negatively-charged N-terminal domain, a polar positively-charged C-terminal domain and a highly hydrophobic core. These overall features should be maintained in order to preserve efficacy. Thus, following the above general outline certain amino acids substitution will lead to active peptides. More specifically, positions 6, 8, 10, 11, 15 and 17 in the p458 peptide chain (corresponding to positions 463, 465, 467, 468, 472 and 474 of the human HSP60 molecule) can be occupied by either I or L or by other hydrophobic amino acids, natural, such as V, M, or F, or unnatural amino acids, such as norleucine (Nle) or norvaline (Nva). Positions 5, 12, 13 and 16 in the p458h chain (corresponding to positions 462, 469, 470 and 473 of the human HSP60 molecule) can be occupied by either K or R or by unnatural positively charged amino acids, such as ornithine (Orn). Interchange of E and D may also lead to active derivatives.

With respect to the peptide carriers of the invention, the term "analogs" relates to peptides obtained by replacement, deletion or addition of amino acid residues to the sequence, optionally including the use of a chemically derivatized residue in place of a non-derivatized residue, as long as they have the capability of enhancing substantially the immunogenicity of viral antigen molecules. Analogs, in the case of p458, are peptides such that at least 70%, preferably 90-100%, of the electric properties and of the hydrophobicity of the peptide molecule are conserved. These peptides can be obtained, without limitation, according to the instructions in the paragraph hereinbefore. Ec27 analogs are preferably of at least about 70%, more preferably of at least about 80-90% similarity in their amino acid sequence of Ec27. For example, the corresponding human peptide, having the sequence set forth in SEQ ID NO:86 (KKDRVTDALNATRAAVEEGI, Ec27h), exhibits 80% amino acid identity to Ec27.

The terms "covalently attached" and "conjugated" as used herein refer to a conjugate comprising an antigen and a synthetic peptide carrier linked either as a continuous fusion peptide or by means of chemical conjugation (either directly or through a spacer), using methods well known in the art.

By "substantially increasing" the immunogenicity of a viral antigen molecule it is meant to comprise both the induction of an increase in the level of antibodies (Abs) against said antigen as well as the presentation of said antibodies as mainly of the IgG isotype. Alternatively, the term may represent an increase in antigen-specific T cell response, as measured either as increased CTL activity (antigen-dependent lysis) or as increased antigen-specific T cell proliferation or cytokine secretion (e.g. Th1 cytokines such as IFNγ). Non-limitative examples for measuring the level of specific Abs and antigen-specific T cell response according to the invention are presented in the Examples hereinbelow.

In another aspect, the viral antigen comprises at least one epitope selected from: a CTL epitope (a MHC I restricted T cell epitope), a B cell epitope and a MHC II restricted T cell epitope. Methods for identifying suitable candidate epitopes are within the abilities of those of skill in the art (for example, without limitation, by using epitope prediction software).

The viral antigen used in the conjugates of the invention may be derived from any virus of interest. In certain embodiments, the virus belongs to the herpesviridae family. This family includes, but is not limited to, human viruses such as human herpesvirus 1 (HHV-1, also known as herpes simplex virus 1, HSV1), HHV-2 (HSV2), HHV-3 (Varicella-zoster virus, VSV), HHV-4 (Epstein-Barr virus, EBV), HHV-5 (cytomegalovirus, CMV), HHV-6, HHV-7 and HHV-8.

In other particular embodiments, the virus belongs to the betaherpesvirus subfamily (e.g. CMV and EBV). In another particular embodiment, the virus is CMV. In one preferred embodiment, the viral antigen is derived from immediate early gene 1 (IE-1) protein of a herpesvirus. In another preferred embodiment, the viral antigen is derived from immediate early gene 1 (IE-1) protein of a CMV. In another preferred embodiment, the viral antigen derived from IE-1 protein comprises a CTL epitope.

In other embodiments, the virus belongs to the Flaviviridae family. This family currently contains three genera, the flaviviruses (e.g. Tick-borne encephalitis viruses, Japanese encephalitis viruses, Dengue, Yellow fever and viruses such as Modoc and Uganda virus), the pestiviruses (e.g. bovine viral diarrhea, Border disease), and the hepatitis C viruses (e.g. hepatitis C virus, HCV).

In various embodiments, the virus is selected from the group consisting of: West Nile virus (WNV), Yellow fever virus, St. Louis encephalitis virus, Murray Valley encephalitis virus, Kunjin virus, Japanese encephalitis virus, Dengue virus type 1, Dengue virus type 2, Dengue virus type 3 and Dengue virus type 4. In one particular embodiment, the viral antigen is derived from West Nile Virus (WNV). In one preferred embodiment, the viral antigen is derived from the WNV envelope (E) protein. In another preferred embodiment, the viral antigen is derived from the E3 domain of said protein. In another preferred embodiment, said viral antigen comprises a B cell epitope and a MHC II restricted epitope.

In other embodiments, there is provided a novel antigen derived from WNV E3 domain of E protein, hereby designated p15, corresponding to aa 355-369 of the E protein. In various embodiments, the antigen has an amino acid sequence as set forth in any one of SEQ ID NOS: 11 and 12 (LVTVNPFVSVATANS and LVTVNPFVSVATANA, respectively). In other embodiments, the invention provides proteins, peptides and conjugates comprising said antigen. For example, without limitation, said antigen may be conjugated with a peptide or lipid carrier or adjuvant.

In another embodiment, the conjugates of the invention comprise a viral antigen having an amino acid sequence as set forth in any one of SEQ ID NOS:11 and 12 covalently attached to a synthetic peptide carrier of the invention. In another embodiment, the conjugate has an amino acid sequence as set forth in any one of SEQ ID NOS:13 (NEDQKIGIEIIKRALKILVTVNPFVSVATANS), 14 (NEDQKIGIEIIKRALKILVTVNPFVSVATANA), (NEDQKIGIEIIKRTLKILVTVNPFVSVATANS), 16 (NEDQKIGIEIIKRTLKILVTVNPFVSVATANA), 77 (KKARVEDALHATRAAVEEGVLVTVNPFVSVATANS), and 78 (KKARVEDALHATRAAVEEGVLVTVNPFVSVATANA).

Other embodiments are directed to homologs, analogs, fragments and derivatives of p15, as detailed hereinbelow.

According to certain embodiments, the invention provides p15 homologs derived from a flavivirus, and active fragments and extensions thereof, as detailed in Table 1:

TABLE 1 p15 homologous epitopes from various flaviviruses, active fragments and extensions thereof, and nucleotide sequences encoding them.

| Virus | Amino acid sequence (SEQ ID NO.) | nucleic acid sequence (SEQ ID NO.) |
|---|---|---|
| West Nile virus | LVTVNPFVSVATANS (11) | 19 |
|  | LVTVNPFVSVATANA (12) | 20 |
|  | GRLVTVNPFVSVATANS (34) | 54 |
|  | GRLVTVNPFVSVATANA (35) | 55 |
| Yellow fever virus | LVTVNPIASTNDDEVLIE (25) |  |
|  | GILVTVNPIASTNDDEVLIE (36) | 45 |
| St. Louis encephalitis virus | LVTVNPFISTGGANNKVM (26) |  |
|  | GRLVTVNPFISTGGANNKVM (37) | 46 |
| Murray Valley encephalitis virus | MVTANPYVASSTANAKVL (27) |  |
|  | GRMVTANPYVASSTANAKVL (38) | 47 |
| Kunjin virus | LVTVNPFVSVSTANAKVL (28) |  |
|  | GRLVTVNPFVSVSTANAKVL (39) | 48 |

TABLE 1-continued p15 homologous epitopes from various flaviviruses, active fragments
and extensions thereof, and nucleotide sequences encoding them.

| Virus | Amino acid sequence (SEQ ID NO.) | nucleic acid sequence (SEQ ID NO.) |
|---|---|---|
| Japanese encephalitis virus | LVTVNPFVATSSANSKVL (29) | |
|  | GRLVTVNPFVATSSANSKVL (40) | 49 |
| Dengue virus type 1 | LITANPIVTDKEKPVNIE (30) | |
|  | GRLITANPIVTDKEKPVNIE (41) | 50 |
| Dengue virus type 2 | LITVNPIVTEKDSPVNIE (31) | |
|  | GRLITVNPIVTEKDSPVNIE (42) | 51 |
| Dengue virus type 3 | LITANPVVTKKEEPVNIE (32) | |
|  | GRLITANPVVTKKEEPVNIE (43) | 52 |
| Dengue virus type 4 | IISSTPLAENTNSVTNIE (33) | |
|  | GRIISSTPLAENTNSVTNIE (44) | 53 |

However, it should be understood that the amino acid sequence of these homologous epitopes may be altered in different variants and strains of these viruses. The present invention is thus further directed to homologous peptides from different variants and strains of these viruses.

With respect to the novel viral peptide antigens of the invention, the term "analogs" relates to peptides obtained by replacement, deletion or addition of amino acid residues to the sequence, optionally including the use of a chemically derivatized residue in place of a non-derivatized residue, as long as their ability to confer immunity against a viral infection when conjugated to the carriers of the invention is retained. The term also includes homologs corresponding to amino acid sequences which are significantly related because of an evolutionary relationship, either between species (ortholog) or within a species (paralog). Peptide sequences having conserved amino acid sequence domains are examples of homologs. With respect to the novel viral peptide antigens of the invention, peptide homologs may have at least about 40% identity in their amino acid sequence, preferably at least 50%, more preferably at least about 70% and most preferably at least about 90% identity. These values reflect the short length of the peptides.

In another aspect, there is provided a second novel WNV epitope derived from the E protein, herein denoted p17, having the following amino acid sequence: YIVVGRGEQQIN-HHWHK (SEQ ID NO:21). Other embodiments are directed to analogs, homologs, fragments, and derivatives thereof.

In various embodiments, these peptides and homologs may be used in conjugation with the carriers of the invention. In certain particular embodiments, the conjugate has an amino acid sequence as set forth in any one of SEQ ID NOS: 23-24 and 56-75.

Peptide and Derivative Synthesis

The polypeptides and peptides of the invention may be synthesized using any recombinant or synthetic method known in the art, including, but not limited to, solid phase (e.g. Boc or f-Moc chemistry) and solution phase synthesis methods. For solid phase peptide synthesis, a summary of the many techniques may be found in: Stewart and Young, 1963; and Meienhofer, 1973. For a review of classical solution synthesis, see Schroder and Lupke, 1965.

The amino acid residues described herein are preferred to be in the "L" isomeric form. However, residues in the "D" isomeric form can be substituted for any L-amino acid residue, as long as the peptide substantially retains the desired functional property. Use of "D" amino acids may be used as is known in the art to increase the stability or half-life of the resultant peptide.

Whenever p458 and Ec27 conjugates are mentioned in the invention, also salts and functional derivatives thereof are contemplated, as long as they are able to substantially enhance the immunogenicity of the antigen molecules. Thus, the present invention encompasses polypeptides or peptides containing non-natural amino acid derivatives or non-protein side chains.

The term derivative includes any chemical derivative of the polypeptides or peptides of the invention having one or more residues chemically derivatized by reaction of side chains or functional groups. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides, which contain one or more naturally occurring amino acid derivatives of the twenty standard amino acid residues. For example: 4-hydroxyproline may be substituted for proline; 5-hydroxylysine may be substituted for lysine; 3-methylhistidine may be substituted for histidine; homoserine may be substituted or serine; and ornithine may be substituted for lysine.

In addition, a peptide or conjugate can differ from the natural sequence of the polypeptides or peptides of the invention by chemical modifications including, but are not limited to, terminal-$NH_2$ acylation, acetylation, or thioglycolic acid amidation, and by terminal-carboxlyamidation, e.g., with ammonia, methylamine, and the like. Peptides can be either linear, cyclic or branched and the like, which conformations can be achieved using methods well known in the art.

It is noted that both shorter active fragments derived from the viral antigens denoted as SEQ ID NOS:11-12, 21 and 25-33 and longer peptides comprising these sequences are within the scope of the present invention. Such fragments or peptides may be comprise, for example, peptides having 1-3 amino acids deleted at either termini, or addition of 1-3 amino acid residues or more from the flanking sequences of the viral protein to either termini, as long as their ability to confer immunity against a viral infection when conjugated to the carriers of the invention is retained. It is to be understood that longer peptides, e.g. up to 50 amino acids in length may also be used for vaccination according to the invention. However, shorter peptides are preferable, in one embodiment, for being easier to manufacture. Such extensions of the novel peptide antigens of the present invention are not intended to include any known protein of fragment, such as the full length E3 domain of a flavivirus. The viral antigens, according to the present invention are preferably 5-50 amino acids in length, more preferably 8-20 amino acids in length. Exemplary fragments and extensions of the p15 and homologs thereof according to the invention are presented in Table 1.

Addition of amino acid residues may be performed at either terminus of the polypeptides or peptides of the invention for the purpose of providing a "linker" by which the peptides of this invention can be conveniently bound to a carrier. Such linkers are usually of at least one amino acid residue and can be of 40 or more residues, more often of 1 to 10 residues. Typical amino acid residues used for linking are tyrosine, cysteine, lysine, glutamic and aspartic acid, or the like.

The conjugates of the invention may also be created by means of chemically conjugating a viral antigen with a p458 or Ec27 synthetic carrier peptide, using methods well known in the art.

Nucleic Acids

In another aspect, the invention provides nucleic acid molecules encoding the peptide antigens of the invention.

The nucleic acid molecules may include DNA, RNA, or derivatives of either DNA or RNA. An isolated nucleic acid sequence encoding a viral antigen or a HSP60 peptide can be obtained from its natural source, either as an entire (i.e., complete) gene or a portion thereof. A nucleic acid molecule can also be produced using recombinant DNA technology (e.g., polymerase chain reaction (PCR) amplification, cloning) or chemical synthesis. Nucleic acid sequences include natural nucleic acid sequences and homologs thereof, including, but not limited to, natural allelic variants and modified nucleic acid sequences in which nucleotides have been inserted, deleted, substituted, and/or inverted in such a manner that such modifications do not substantially interfere with the nucleic acid molecule's ability to encode a functional peptide of the present invention.

A nucleic acid molecule homolog can be produced using a number of methods known to those skilled in the art (see, for example, Sambrook et al., 1989). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologs can be selected from a mixture of modified nucleic acids by screening for the function of the protein encoded by the nucleic acid with respect to the induction of an anti-viral response, for example by the methods described herein.

A polynucleotide or oligonucleotide sequence can be deduced from the genetic code of a protein, however, the degeneracy of the code must be taken into account. For example, an oligonucleotide having a nucleic acid sequence: ctggtgaccgtgaatccatttgtgtctgtggccacagccaactcg (SEQ ID NO:19) encodes a p15 antigen derived from West Nile Virus E protein: LVTVNPFVSVATANS (SEQ ID NO:11). However, nucleic acid sequences of the invention also include sequences, which are degenerate as a result of the genetic code, which sequences may be readily determined by those of ordinary skill in the art. In other particular embodiments, the viral antigens of the invention are encoded by oligonucleotides having a nucleic acid sequence as set forth in any one of SEQ ID NOS:20, 22 and 45-55 (see Table 1).

The oligonucleotides or polynucleotides of the invention may contain a modified internucleoside phosphate backbone to improve the bioavailability and hybridization properties of the oligonucleotide or polynucleotide. Linkages are selected from the group consisting of phosphodiester, phosphotriester, methylphosphonate, phosphoro selenoate, phosphorodiselenoate, phosphoroanilothioate, phosphoroanilidate, phosphoramidate, phosphorothioate, phosphorodithioate or combinations thereof.

Additional nuclease linkages include alkylphosphotriester such as methyl- and ethylphosphotriester, carbonate such as carboxymethyl ester, carbamate, morpholino carbamate, 3'-thioformacetal, silyl such as dialkyl (C1-C6)- or diphenylsilyl, sulfamate ester, and the like. Such linkages and methods for introducing them into oligonucleotides are described in many references, e.g. reviewed generally by Peyman and Ulmann, (1990).

The present invention includes a nucleic acid sequence of the present invention operably linked to one or more transcription control sequences to form a recombinant molecule. The phrase "operably linked" refers to linking a nucleic acid sequence to a transcription control sequence in a manner such that the molecule is able to be expressed when transfected (i.e., transformed, transduced or transfected) into a host cell. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in animal, bacteria, helminth, insect cells, and animal cells.

A nucleic acid molecule of the invention may be inserted into appropriate expression vector, i.e., a vector which contains the necessary elements for the transcription and translation of the inserted coding sequence.

Vectors can be introduced into cells or tissues by any one of a variety of known methods within the art, including in vitro recombinant DNA techniques, synthetic techniques, and in vivo genetic recombination. Such methods are generally described in Sambrook et al., (1989, 1992), in Ausubel et al., Current Protocols in Molecular Biology, John Wiley and Sons, Baltimore, Md. 1989.

A recombinant cell of the present invention comprises a cell transfected with a nucleic acid molecule that encodes a viral antigen of the invention. A variety of expression vector/host systems may be utilized to contain and express sequences encoding the viral antigens of the invention. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed. The expression of the construct according to the present invention within the host cell may be transient or it may be stably integrated in the genome thereof.

Vaccine Compositions and Methods Thereof

According to some aspects the present invention provides a vaccine comprising an isolated viral antigenic peptide and a peptide comprising a T cell epitope of HSP60, wherein the HSP60 peptide enhances the immunogenicity of the viral antigenic peptide by at least two fold compared to the peptide without the HSP60 peptide. In certain currently preferred embodiments the immunogenicity is enhanced by at least 4-5 fold.

In certain embodiments the vaccine compositions comprise a T cell epitope of HSP60 suitable to enhance the immunogenicity when used as an adjuvant peptide that is mixed with the viral antigen. According to certain particular embodiments, the adjuvant peptide is selected from Ec27 and analogs and derivatives thereof. In alternative embodiments the vaccine comprises a T cell epitope of HSP60 suitable to enhance the immunogenicity of the viral antigenic peptide when used in conjugates where the HSP60 peptide is covalently linked to the viral antigenic peptide. In some particular embodiments, the peptide carrier is selected from p458, Ec27 and analogs and derivatives thereof. The enhanced immunogenicity of said viral antigen is measured by at least one of the following: serum titer of antibodies directed to said viral antigen; T cell proliferation in the presence of said viral antigen; cytokine secretion induced by said viral antigen; specific T cell mediated lysis of virus-infected cells; and reduction of detectable viral load.

In another aspect, the invention provides vaccine compositions comprising the conjugates of the invention and a pharmaceutically acceptable carrier, adjuvant, excipient or diluent.

In another aspect, the invention provides vaccine compositions comprising a polypeptide or peptide, said polypeptide or peptide comprising an amino acid sequence as set forth in any one of SEQ ID NOS:11-12, 21 and 25-44, and a pharmaceutically acceptable carrier, adjuvant, excipient or diluent.

In one embodiment of the invention, the composition is useful for treating or preventing a viral infection in a subject in need thereof, as described herein.

The vaccine composition of the invention is administered to a subject in need thereof in an effective amount. According to the present invention, an "effective amount" is an amount that when administered to a subject results in a substantial increase in the immune response of the subject to said viral antigen, as described herein.

According certain embodiments, the subject is selected from the group consisting of humans, non-human mammals and non-mammalian animals (e.g. birds). In a preferred embodiment, the subject is human.

Pharmaceutical and veterinary compositions for use in accordance with these embodiments may be formulated in conventional manner using one or more physiologically acceptable carriers or excipients (vehicles). The carrier(s) are "acceptable" in the sense of being compatible with the other ingredients of the composition and not deleterious to the recipient thereof. The vaccine composition can be optionally administered in a pharmaceutically or physiologically acceptable vehicle, such as physiological saline or ethanol polyols such as glycerol or propylene glycol.

The polypeptides and peptides of the invention may be formulated into the vaccine as neutral or salt forms. Pharmaceutically acceptable salts include the acid addition salts (formed with free amino groups of the peptide) and which are formed with inorganic acids such as, for example, hydrochloric or phosphoric acids, or such organic acids such as acetic, oxalic, tartaric and maleic. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine and procaine.

The vaccine composition may optionally comprise additional adjuvants such as vegetable oils or emulsions thereof, surface active substances, e.g., hexadecylamin, octadecyl amino acid esters, octadecylamine, lysolecithin, dimethyl-dioctadecylammonium bromide, N,N-dicoctadecyl-N'-N' bis (2-hydroxyethyl-propane diamine), methoxyhexadecylglycerol, and pluronic polyols; polyamines, e.g., pyran, dextransulfate, poly IC, carbopol; peptides, e.g., muramyl dipeptide, dimethylglycine, tuftsin; immune stimulating complexes; oil emulsions (including, but not limited to, oil-in-water emulsions having oil droplets in the submicron range, such as those disclosed by U.S. Pat. Nos. 5,961,970, 4,073,943 and 4,168,308); liposaccharides such as MPL® and mineral gels. The antigens of this invention can also be incorporated into liposomes, cochleates, biodegradable polymers such as poly-lactide, poly-glycolide and poly-lactide-co-glycolides, or ISCOMS (immunostimulating complexes), and supplementary active ingredients may also be employed. The protein and peptide antigens of the present invention can be coupled to albumin or to other carrier molecule in order to modulate or enhance the immune response, all as are well known to those of ordinary skill in the vaccine art.

The vaccines can be administered to a human or animal by a variety of routes, including but not limited to parenteral, intradermal, transdermal (such as by the use of slow release polymers), intramuscular, intraperitoneal, intravenous, subcutaneous, oral and intranasal routes of administration, according to protocols well known in the art. The particular dosage of the conjugate antigen will depend upon the age, weight and medical condition of the subject to be treated, as well as on the identity of the antigen and the method of administration. Suitable doses will be readily determined by the skilled artisan. A preferred dose for human intramuscular, subcutaneous and oral vaccination is between about 6 µg to about 70 mg per kg body weight, preferably between about 15 µg to about 28 mg per kg body weight, and more preferably between about 40 µg to about 7 mg per kg body weight. Adjustment and manipulation of established dosage ranges used with traditional carrier antigens for adaptation to the present vaccine is well within the ability of those skilled in the art.

In various embodiments, the vaccine composition s of the invention may be used in combination with other treatments and medicaments, e.g. anti-viral drugs. For example, a conjugate comprising a CTL epitope derived from 1E-1 protein of HCMV and a peptide carrier of the invention may be administered to HCMV infected subjects in combination with gancyclovir therapy. Doses and administration regimes of gancyclovir are known in the art.

In another aspect, the present invention is directed to the use of a conjugate of the invention for the preparation of a vaccine composition useful for conferring anti-vial immunity.

In yet another aspect, the invention provides methods for increasing the immunogenicity of a viral antigen which comprises linking the antigen to a synthetic peptide carrier of the invention.

In another aspect, the invention provides methods for immunizing a subject in need thereof against a viral infection, comprising administering to the subject an effective amount of a vaccine composition comprising a conjugate of the invention and a pharmaceutically acceptable carrier, adjuvant, excipient or diluent.

In various embodiments, the vaccine composition may be administered to said subject before the exposure of said subject to the virus or after exposure of said subject to said virus.

In another aspect, the invention provides methods comprising:
(a) isolating a viral antigen, comprising at least one epitope selected from: a CTL epitope, a B cell epitope and a MHC II-restricted epitope;
(b) conjugating said viral antigen to a synthetic peptide carrier of the invention; and
(c) administering to the subject an effective amount of a vaccine composition comprising a conjugate of the invention and a pharmaceutically acceptable carrier, adjuvant, excipient or diluent.

Diagnostic Kits and Methods Thereof

Other embodiments of the present invention are directed to diagnostic compositions and kits and uses thereof for the diagnosis of flavivirus infection.

The present invention provides a method for diagnosing the presence of, or exposure to a flavivirus in a patient, comprising testing said patient for the presence of anti-flavivirus antibodies or of a T cells which immunoreact with flavivirus epitopes using a peptide according to Table 1 or analogs, derivatives and salts thereof as antigen.

In one embodiment, the method comprises the steps of:
(a) contacting a suitable biological specimen with a viral antigen having an amino acid sequence as set forth in any one of SEQ ID NOS:11-12, 21 and 25-44 and analogs, homologs, derivatives and salts thereof under conditions such that an immune reaction can occur;
(b) quantifying the immune reaction between the peptide antigen and the biological specimen,
wherein an immune reaction significantly higher than an immune reaction obtained for a sample obtained from a non-infected subject is indicative of exposure to, or, in other embodiments, infection of the subject with a flavivirus.

A biological specimen or sample that may be assayed for flavivirus infection may include, for example, mammalian body fluids (e.g. serum, tissue extracts, tissue fluids, mucosal secretions), in vitro cell culture supernatants, cell lysates and cells or tissue from the subject that have been cultured in cell culture (e.g. leukocyte samples such as peripheral blood mononuclear cells). Methods of obtaining a suitable biological sample from a subject are known to those skilled in the art.

In certain embodiments, the peptides and peptide compositions prepared in accordance with the present invention can be used to detect anti-flavivirus antibodies and diagnose flavivirus infection by using them as the test reagent in an enzyme-linked immunoadsorbent assay (ELISA), an enzyme immunodot assay, a passive hemagglutination assay (e.g., PHA test), an antibody-peptide-antibody sandwich assay, a peptide-antibody-peptide sandwich assay, or other well-known immunoassays. In accordance with the present invention, any suitable immunoassay can be used with the subject peptides. Such techniques are well known to the ordinarily skilled artisan and have been described in many standard immunology manuals and texts. In one particular embodiment, the immunoassay is an ELISA using a solid phase coated with the peptide compositions of the present invention. For example, such a kit for determining the presence of anti-flavivirus antibodies may contain a solid-phase immobilized peptide of the invention and a tagged antibody capable of recognizing the non-variable region of the anti-flavivirus antibody to be detected, such as tagged anti-human Fab. The kit may also contain directions for using the kit and containers to hold the materials of the kit. Any conventional tag or label may be used, such as a radioisotope, an enzyme, a chromophore or a fluorophore. A typical radioisotope is iodine-125 or sulfur-35. Typical enzymes for this purpose include horseradish peroxidase, horseradish galactosidase and alkaline phosphatase.

In other embodiments, the presence of T cells immunoreactive with flavivirus epitopes may be determined, for example, by determining T cell proliferation or cytokine secretion induced by the novel viral peptide epitopes of the invention, using methods well known in the art. Several non-limitative examples of determining T cell reactivity with peptide antigens are presented in the Examples herein. For example, a kit for diagnosing flavivirus exposure or infection by testing for the presence of a T cell which immunoreacts with flaviviral epitopes, may comprise: an antigen selected from the peptides of the invention; a suitable medium for culture of lymphocytes (T cells); and either a labeled nucleotide for the T cell proliferation test, or a cytokine, e.g., interferon-gamma, assay kit, for the cytokine test.

In various embodiments, the method may comprise the steps of:
(a) contacting a suitable biological sample with a viral antigen having an amino acid sequence as set forth in any one of SEQ ID NOS:11-12, 21 and 25-44 and analogs, homologs, derivatives and salts thereof under conditions such that an immune reaction can occur;
(b) determining whether the peptide antigen binds specifically to the biological sample.

The term "binds specifically to the biological sample" as used herein refers to occurrence of an immune reaction between a component of the biological specimen or sample (e.g. antibodies and T cells) and the viral peptide antigen having higher affinity or extent than to another antigen. For example, specific binding may be measured by determining the extent of antigen-antibody complex formation, T cell proliferation or cytokine secretion. Thus, for example, step (b) may include determining the extent of antigen-antibody complex formation, wherein an antigen-antibody complex formation level significantly higher than the level obtained for a sample obtained from a subject not previously exposed to or infected by a flavivirus is indicative of exposure of the subject to the flavivirus.

The kits and methods of the present invention may be used, in some embodiments, for the differential diagnosis of a flavivirus infection, enabling the identification of the particular flavivirus strain infecting the subject or to which the subject was exposed. For example, a biological specimen may be assayed for the presence of anti-Dengue antibodies using the peptides having an amino acid sequence as set forth in SEQ ID NOS:30-33 to determine the strain of Dengue virus infecting the subject (e.g. to distinguish between Dengue 1, 2, 3 or 4 infection).

The following examples are presented in order to more fully illustrate some embodiments of the invention. They should, in no way be construed, however, as limiting the broad scope of the invention.

EXAMPLES

A. CMV Vaccination
Materials and Methods
Mice

BALB/c female mice were purchased from Harlan Olac (Bicester, UK). Mice were maintained under specific pathogen free conditions and were allowed to adjust to the facility for 1 week before any experiments were performed. For the pathogenesis experiments, mice were used at 6 to 8 weeks of age and for the immunization experiments, mice were used at 3 weeks of age. The mouse experiments were approved by and performed according to the guidelines of the Ben Gurion University Faculty of Health Sciences Animal Safety Committee.

MCMV

The Smith strain of MCMV was obtained from the American Type Culture Collection (ATCC) (Rockville, Md.). Highly virulent salivary gland-passaged MCMV stocks were prepared as a 10% (wt/vol) homogenate of salivary gland from day 14-infected BALB/c in DMEM-10% FCS. Homogenates were clarified by low speed centrifugation, DMSO was added to final concentration of 10%, and virus stocks were stored in aliquots at −70° C. until use (Palmon et al., 1996).

MCMV titers in these salivary gland suspension (SGS) stocks were determined by a quantitative plaque assay (Rager Zisman et al., 1973). Briefly, confluent monolayers of secondary mouse embryo fibroblasts (MEF) were prepared in 24 well plates. Serial 10-fold dilutions of SGS containing MCMV were prepared in DMEM supplemented with 2% FCS. The growth medium from each well in MEF plates was aspirated, and duplicate wells were inoculated with 0.2 ml of diluted SGS. After an adsorption period of 1 hour at 37° C., monolayers were overlayed with 0.8 ml of growth medium containing 0.75% carboxymethyl cellulose (CMC), incubated for 5 days at 37° C. in a humidified 5% $CO_2$ incubator, fixed in PBS-10% formaldehyde and stained with Crystal Violet to visualize virus plaques. Titers were expressed as $log_{10}$ pfu/0.1 gr tissue. Thorough this study virus stocks containing $1.75×10^8$ pfu/0.1 g of tissue were used.

Infection with MCMV and Virus Titers in Target Organs

To study the course of MCMV infection in naïve or immunized BALB/c mice, mice were inoculated intraperitoneally (i.p.) with $5×10^4$ pfu of stock virus in 0.2 ml PBS. Mice were sacrificed at different time points, spleens and salivary glands (pooled 3 mice per group at each time point) were removed and 10% (wt/vol) homogenates were prepared as previously described (Palmon et al., 1996). Samples were stored at −70° C. until infectious virus titrations were performed on primary cultures of MEF.

Preparation of DNA and Amplification by PCR

DNA was extracted from naïve and infected spleens and salivary gland using QiAmp Tissue Kit (QIAGEN Inc. Chatsworth, Calif., USA), according to appropriate QiAmp protocols. DNA oligonucleotide primers were synthesized according to the published sequence of MCMV gB gene (Rapp et al., 1992). The sequence of gB sense strand primer was based on the cDNA sequence no. 2416-2443 (5'-AAG-CAG-CAC-ATC-CGC-ACC-CTG-AGC-GCC-3' SEQ ID NO:17) and the antisense no. 2745-2772 (5'-CCA-GGC-GCT-CCC-GGC-GGC-CCG-CTC-TCG-3' SEQ ID NO:18). This gB gene primer pair amplifying a 356 bp segment was found the most sensitive in previous studies (Palmon et al., 1996). For gene amplification, 1 μg of DNA sample was added to the reaction mixture containing 200 μM each dNTP, 100 pmol each primer, 1.0 mM $MgSO_4$, 10 mM KCl, 10 mM $(NH_4)_2SO_4$, 20 mM Tris-HCl (pH 8.8), 0.1% Triton X-100 and 2 U of vent polymerase (Biolabs) in a total reaction volume of 50 μl each. Samples were amplified for 30 cycles in an automated thermal cycler (Perkin Elmer Cetus, USA). Each cycle entailed denaturation at 94° C. for 60 sec, annealing at 68° C. for 90 sec and primer extension at 72° C. for 120 sec. PCR products were electrophoretically separated on 1.5% agarose gel, stained with ethidium bromide, and photographed. The lower limit of detection for this method under the experimental conditions was 5 femtograms of viral DNA corresponding to about 20 copies of the MCMV genome (Palmon et al., 1996).

Peptides

Peptides were prepared in the Weizmann Institute of Science (Rehovot, Israel), and in Albert Einstein College of Medicine (New-York USA). The purity of the peptides was ascertained by analytical reversed-phase HPLC and amino acid (aa) analysis. The sequences of the six peptides synthesized are: 89pep (MCMV pp 89 ie1-CTL epitope, Reddehase et al., 1989)-YPHFHPTNL (SEQ ID NO:5); p458 (the active peptide derived from mouse HSP60, Konen Waisman et al., 1999)-NEDQKIGIEIIKRALKI (SEQ ID NO:2); p458-89pep (combined)-NEDQKIGIEIIKRALKIYPHFHPTNL (SEQ ID NO:6); negative control for p458 (the p431 peptide of the mycobacterial HSP60, 442val-deleted)-EGDEAT-GANI-KVALEA (SEQ ID NO:7); control-89pep (combined)-EGDEATGANI-KVALEAYPHFHPTNL (SEQ ID NO:8); and TTp30-89pep (combined)-FNNFTVSFWLRVP-KVSASHLEYPHFMPTNL (SEQ ID NO:9). The p30 of TT (aa 947-967) (Panina-Bordignon et al., 1989) (SEQ ID NO:10) is now being used as a carrier peptide in various vaccines (Brander et al., 1996; Keitel et al., 1999). The mycobacterial p431 peptide (442val-deleted) was used as a negative control peptide since it is homologous in sequence to mammalian p458, but did not elicit a $CD4^+$-dependent immune response against itself or p458.

Immunization and Challenge of Mice with MCMV

The immunizing dose of each peptide was equimolar to 15 μg of p458 (Konen Waisman et al., 1999). All peptides were emulsified in incomplete Freund's adjuvant (IFA), and the volumes for intra-footpad (i.f.p.) and subcutaneous (s.c.) injections were 50 μl and 100 μl respectively. Two different protocols were used. To study the immune response of mice to the chimeric peptide (p458-89pep), groups of 6-week old to 8-week old mice were immunized once into the hind footpad with peptides emulsified in IFA. Ten days later several mice were sacrificed, and organs were harvested for IFNγ and IL-4 assays. To study the protective efficacy of the combined peptide, groups of 3-week old mice were immunized and boosted according to the following protocol: mice were immunized i.f.p. on day (−24), and boosted s.c. two weeks later on day (−10). Ten days later (day 0), mice were challenged IP with $5×10^4$ pfu of MCMV. Mice were sacrificed on days 14, 21, and 28 after challenge, and organs were harvested for virus titrations, PCR, cytotoxic T cell and cytokine assays.

Preparation of Spleen and Salivary Gland Mononuclear Cell Cultures

Spleen pulp was extruded from the capsule in a non-tissue culture Petri dish in RPMI-1640 medium supplemented with 100 U/ml penicillin, 100 μg/ml streptomycin, 2 mM glutamine, 10 mM HEPES and 5% FCS (base-RPMI). Spleen cell suspensions were passaged through a cell strainer, washed once, treated 2 min with ACK lysing buffer (0.15M $NH_4Cl$, 0.01 $KHCO_3$; 2 ml/spleen) for elimination of erythrocytes, and washed twice in base-medium. Splenocytes were resuspended in RPMI-1640 medium supplemented with 100 U/ml penicillin, 100 μg/ml streptomycin, 2 mM glutamine, 10 mM HEPES, $5 \times 10^{-5}$ M β-mercaptoethanol and 10% FCS (complete RPMI) in a final concentration of $5 \times 10^6$ cells/ml.

Salivary gland cell suspensions were prepared by initially cutting the salivary glands into small fragments (<2 mm) in a non-tissue culture Petri dish. Fragments were treated with base-medium containing 1 mg of collagenase-dispase (Roche Diagnostics, Germany)/ml and 50 μg of DNase I (Boehringer Mannheim, Germany)/ml. After 1 h incubation in 37° C., cells were resuspended in 45% Percoll (Sigma Chemical Co., Israel), overlayed on 66% Percoll and centrifuged at 800 g for 25 min. Mononuclear cells collected at the interphase, were counted and resuspended in complete-RPMI to a final concentration of $5 \times 10^6$ cells/ml.

IFNγ and IL-4 ELISA Assays

Mononuclear cell cultures from spleens and salivary gland were prepared as described above. Cell suspensions were divided into 24 well plates ($5 \times 10^6$ cells/well) and were stimulated in vitro with either 10 μg/ml of 89pep or p458 or with 5 μg/ml Concanavalin-A (Con-A). Cells were incubated for 72 h (with or w/o stimulation) at 37° C. in a humidified 5% CO2 incubator. After incubation supernatants were collected, and IFNγ and IL-4 levels were measured using indirect ELISA according to Pharmingen cytokine ELISA protocol (Pharmingen, San Diego, Calif.).

FACS Analysis of Cell Phenotypes and Intracellular IFNγ

For phenotypic analysis, spleen and salivary gland mononuclear cells of MCMV-infected and naïve mice were cultured as described above and were stained for CD8 and CD4, IFNγ and IL-5 using directly-labeled antibodies (PharMingen, San Diego, Calif.). Intracellular cell staining (ICCS) for IFNγ, IL-4 and IL-5 was performed using PharMingen's Cytofix/Cytoperm Plus kit with GolgiPlug (containing Brefeldin A) according to the manufacturer's instructions. Briefly, GolgiPlug was added to the 8 h-incubated immune cell cultures (established as described above, with or w/o peptide stimulation). After the additional 6 h of incubation in the incubator cells (minimum $10^6$ per sample) were harvested, washed in PBS supplemented with 2% FBS and 0.09% Sodium azide, and incubated in 50 μl of FC blocker, labeled with anti-CD4 and anti-CD8 surface markers. Then cells were fixed, permeabilized and treated with anti-IFNγ, anti-IL-4 or anti-IL-5 antibodies for intracellular cytokine detection. Stained cells were immediately analyzed on a FACSCalibur flow cytometer (Becton-Dickinson, Mansfield, Mass.) and 50,000 to 100,000 events/sample were acquired and analyzed with CellQuest software.

Cytotoxic T Cell Assay

The cytotoxic activity against the MCMV 89pep was assessed in a 4-h cytotoxic assay using the CytoTox 96 non-radioactive, colorimetric-based kit (Promega, Madison, Wis.), according to manufacturer instructions. This assay is based on the quantitative measurement of lactate dehydrogenase, a stable cytosolic enzyme that is released upon cell lysis. Spleen cell suspensions from immunized mice, prepared as described above, were re-stimulated in vitro for 6 days with 89pep (10 μg/ml) and rhIL-2 (25 IU/ml) from day 2. Target cells for the lysis assay were P815 cells (mastocytoma, $H-2^d$). P815 were either non-pulsed or pulsed with 89pep (1 μg/ml) for 2 h and then washed before incubation with effector cells. In all experiments shown, the spontaneous release was less than 25% of maximal release. Each point in a lysis assay represents the average of triplicate values. The range of the triplicates was within 5% of their mean.

Example 1

Natural History of MCMV Dissemination in Spleen and Salivary Gland

Figure 1B:
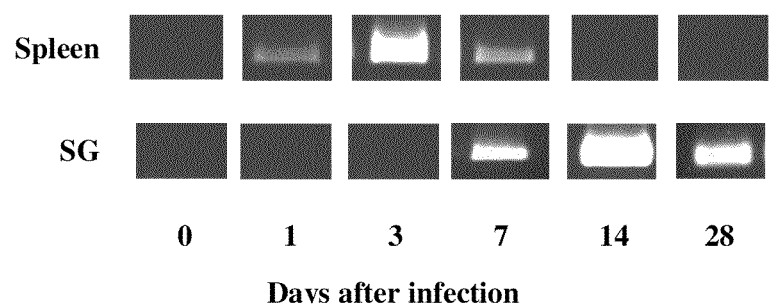

MCMV infection is characterized by different kinetics and viral loads in different organs (Mercer and Spector, 1986). BALB/c mice, 6-8 weeks old, were injected i.p. with $5 \times 10^4$ pfu of MCMV. Mice were sacrificed on days 1, 3, 7, 14 and 28 after infection, and spleens and salivary glands were assayed for infectious virus and MCMV DNA. FIG. 1, shows a typical pattern of MCMV replication in spleen (empty diamonds) and salivary gland (full squares). Virus replication peaked in the spleen on day 3 after infection, and slowly declined thereafter (FIG. 1A). By day 14, no infectious virus could be recovered from this organ. To detect MCMV DNA in infected organs, we used a sensitive PCR using a gB gene primer pair that amplifies a 356 bp segment (Palmon et al., 1996). Viral DNA was detected in the spleen as early as day 1 after infection, peaked on day 3 and by day 14 no DNA could be detected (FIG. 1B).

In the salivary gland, virus appeared on day 7. Virus replication in this organ steadily increased, peaking by day 14 ($3 \times 10^8$ pfu/0.1 gr tissue, FIG. 1A). A moderate decline in virus titers ensued, and at day 28, $1.5 \times 10^6$ pfu/0.1 gr tissue were still recoverable from the salivary gland. No infectious virus could be detected in the SG (and in any other organ) by day 42 post challenge (data not shown and Keitel et al., 1999) The detection of viral DNA was associated with the presence of infectious virus. DNA increased from day 7 to 14. Large amounts of viral DNA could still be detected on day 28 after infection (FIG. 1B). On this background of viral dissemination, replication, splenic clearance and salivary gland persistence, we evaluated the efficacy of immunization with the p458-89pep chimeric peptide. We also studied MCMV load in lungs after challenge of naïve 6-8 week old mice; MCMV load (pfu) maximized on day 7 and disappeared by day 14 (data not shown). Thus, in our model we concentrated on the salivary gland because it is considered as the major site for viral persistence of MCMV in mice (FIG. 1 and Ho, 1991; Koszinowski et al., 1990, Kirchner, 1983; Mercer and Spector, 1986).

Example 2

Immunization with p458-89pep Suppresses MCMV Persistence in the Salivary Gland

89pep is the $H-2L^d$-restricted YPHFMPTNL epitope of MCMV-pp 89 (Reddehase et al., 1989). We synthesized chimeric p458-89pep and compared its protective efficacy against MCMV to that induced by 89pep alone or by negative control-89pep. p458 is a MHC class II-restricted peptide derived from murine HSP60 (aa 458-474) and capable of inducing CD4+ T responses in BALB/c mice (Amir-Kroll et al., 2003). The mycobacterial HSP60 431-447 aa peptide (with a val deletion at position 442) did not elicit an immune response to itself or to p458, and thus served as a negative control peptide for immunization; control-89pep.

Figure 2A:
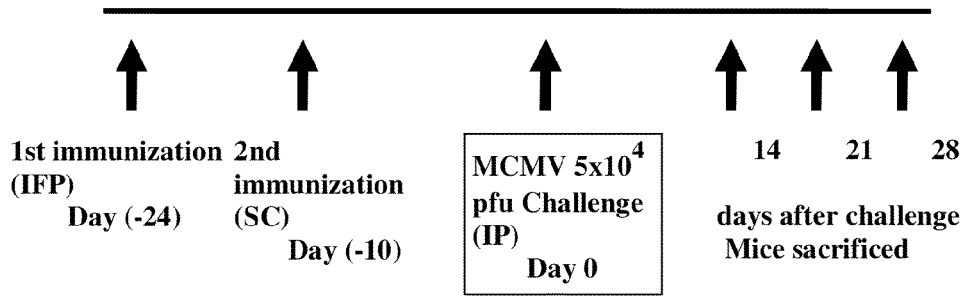
FIG. 2. The effectiveness of the p458-89pep vaccine. A. The experimental design. B. Infectious MCMV titers in salivary gland 14, 21 and 28 days after challenge. Data represent the average titer (±SE) of the salivary glands of 3 individual mice of each group. In salivary glands of mice immunized with p458-89pep, virus titers on day 28 (asterisks) were below detection (i.e. <2 $\log_{10}$ pfu/0.1 gr tissue). C. PCR amplification of the 356 bp product of MCMV gB. Template DNA was extracted from salivary glands of immunized mice on day 28 after MCMV challenge. Immunization with: a. IFA only without challenge; b. IFA only; c. 89pep; d. p458-89pep; e. control-89pep; f. PCR mix without template DNA (negative PCR control). Results are from 1 representative experiment of 2 performed.

To investigate whether immunization with the different peptides would decrease MCMV replication in salivary glands, 3-week old BALB/c mice were immunized twice with IFA alone, 89pep, p458-89pep or control-89pep (FIG. 2). Three-week old, female BALB/c mice were immunized (i.f.p.) with various peptides, and were boosted (s.c.). Two weeks later, the mice were challenged (i.p.) with $5 \times 10^4$ pfu MCMV, day 0. Three mice from each group were sacrificed on days 14, 21, and 28 after challenge.

Figure 2B:
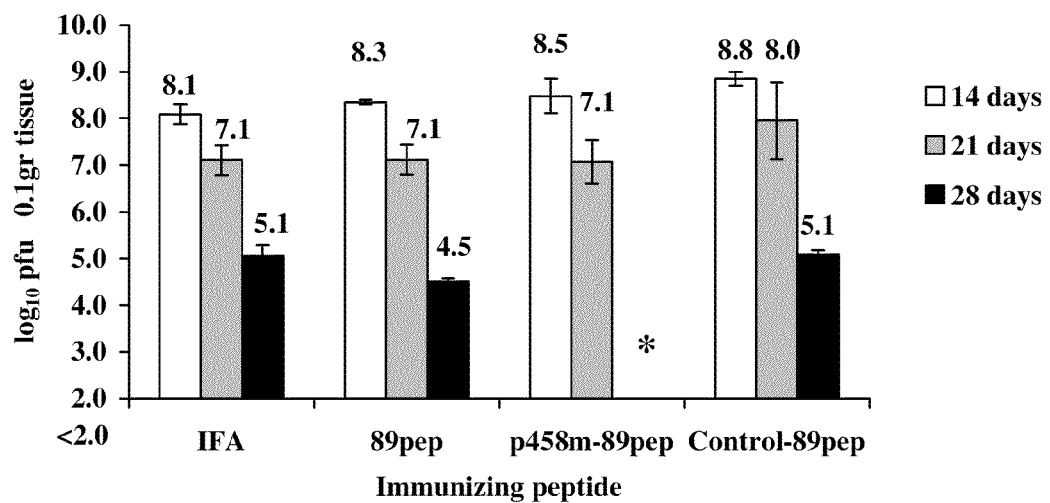

Peptides for vaccination were emulsified in IFA. Ten days after the last immunization, mice were challenged i.p. with $5 \times 10^4$ pfu of MCMV (day 0). Mice were sacrificed on days 14, 21, and 28 after challenge, and infectious virus titers and MCMV-DNA were measured by plaque and PCR assays in the salivary glands. As shown in FIG. 2B, no effect of immunization with any of the peptides could be demonstrated on days 14 and 21 after virus challenge; on day 14, virus titers ranged from 8.1 to 8.8 $\log_{10}$ pfu/0.1 g, and on day 21 ranged from 7.1 to 8.0 $\log_{10}$ pfu/0.1 g.

Figure 2C:
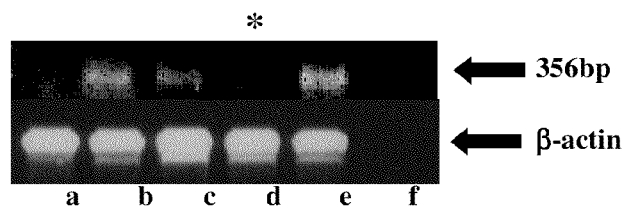

On day 28, however, MCMV was not detectable in the salivary glands of the p458-89pep-immunized mice (<2 $\log_{10}$ pfu/0.1 g). Immunization with 89pep alone showed a marginal advantage compared to IFA-immunized mice (FIG. 2B); the viral load was 4.5 and 5.1 $\log_{10}$ pfu/0.1 g, respectively. Immunization with control-89pep did not affect the viral load. Other experiments were performed with the same experimental design in which TTp30-89pep was used; immunization with TTp30-89pep did not affect viral load on days 14 and 21, reduced viral load on day 28 by two fold, on average, but failed to eliminate infectious virus on day 28. To further evaluate the virus suppression induced by the p458-89pep immunization, we used a sensitive viral gB PCR to detect viral DNA. We previously showed that 1 pfu is the equivalent of approximately 1500 viral genomes (Palmon et al., 2000). Yet, on day 28, even this assay failed to reveal any gB PCR product in salivary glands of mice immunized with p458-89pep (FIG. 2C, lane d). Therefore, only immunization with the p458-89pep led to the elimination of detectable MCMV from the salivary gland, on day 28.

Example 3

IFNγ Secretion by 89Pep-Specific T Cells Following Infection and Vaccination

Figure 3A:
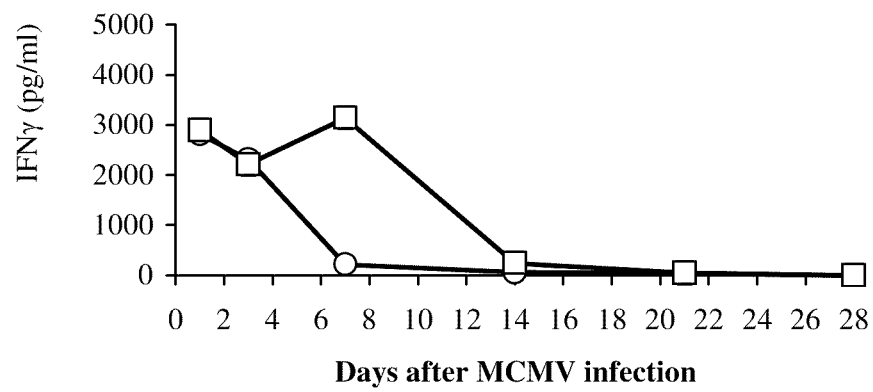
FIG. 3. IFNγ secretion from spleen and salivary gland (SG) cell cultures of MCMV infected mice. Spleen cell (FIG. 3A) and fractionated salivary gland mononuclear cell cultures (FIG. 3B) were prepared on different days after virus infection as described in methods. IFNγ secretion in supernatant was measured by ELISA after 3 days culture with (squares) or without (circles) 89pep stimulation (10 μg/ml) in vitro. Data represent the average (±SE) of 3 experiments.
Figure 3B:
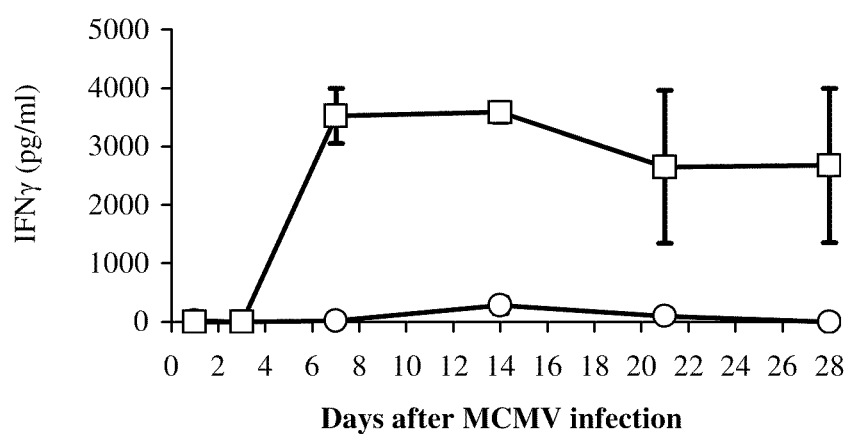

It is well established that clearance of MCMV during acute infection depends primarily on Th1 IFNγ secretion and protective CTL responses (Mercer and Spector, 1986; Reddehase et al., 1989). We tested whether IFNγ secretion was stimulated by 89pep from spleen (FIG. 3A) and salivary gland (FIG. 3B) cell cultures of MCMV-challenged mice. Cell cultures were prepared on days 1, 3, 7, 14, 21, and 28 after infection, plated for 3 d with or without 89pep, and IFNγ secretion was measured. In the absence of 89pep stimulation, secretion of IFNγ was detected only in spleen cultures from days 1 and 3 after infection. This result probably reflects NK activity in the early stages of infection. When 89pep was added to the cultures, IFNγ secretion in spleen and salivary glands was correlated with the kinetics of viral replication in these organs (FIGS. 1A and 3). It is noteworthy that no significant IL-4 secretion was detected in the culture supernatants; however, the cells were capable of secreting IL-4 along with other cytokines in response to stimulation with Con-A (data not shown).

Figure 4:
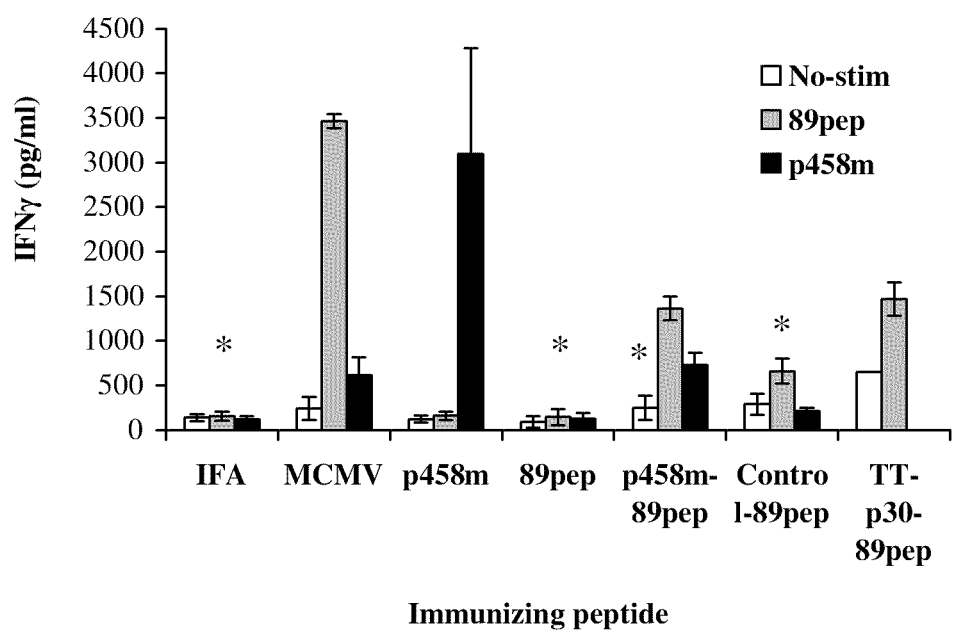
FIG. 4. IFNγ levels from spleen cell cultures after vaccination with p458-89pep. Spleen cell cultures were prepared 10 days after vaccination with the various peptides or after challenge of naïve mice with MCMV. A control group received IFA without any peptide. IFNγ secretion in supernatants was measured by ELISA after 3 days stimulation in vitro with p458, 89pep (10 μg/ml), or without stimulation (No-stim). Data represent the average of 6 experiments (±SE). * p≤0.05 compared to p458-89pep, two-tailed T-test.

We investigated whether immunization with p458-89pep induced 89pep-specific IFNγ secretion. Mice received a single immunization with the following peptides: p458-89pep, 89pep, p458, control-89pep or TTp30-89pep. TTp30 is a MHC class II-restricted peptide capable of inducing vigorous CD4+ T responses and IFNγ production in BALB/c mice and used as a universal adjuvant (Panina-Bordignon et al., 1989, Amir-Kroll et al., 2003). In addition, a non-vaccinated group was infected with MCMV. Ten days after immunization with the different peptides or infection, mice were sacrificed, and spleen cell and salivary gland cultures were prepared and stimulated in vitro for 3 d with 89pep or p458. FIG. 4 shows that spleen cells derived from mice immunized with p458-89pep and re-stimulated in vitro with 89pep secreted significantly higher (p<0.05) levels of IFNγ compared to mice immunized with 89pep, p458, control-89pep or IFA-only. 89pep-restimulated splenocytes from p458-89pep-immunized mice secreted significantly higher (p<0.05) levels of IFNγ compared to the same but non-re-stimulated splenocytes (FIG. 4). Thus, immunization with p458-89pep induced specific and significantly enhanced IFNγ secretion. In these experiments we also tested the TTp30-89pep. Immunization with TTp30-89pep followed by 89pep re-stimulation induced IFNγ levels similar to those of mice immunized with p458-89pep (FIG. 4). The highest levels of 89pep-specific IFNγ secretion were obtained in spleen cell cultures from mice infected with virus (FIG. 4). This high IFNγ secretion by spleen cells from MCMV-infected mice, after in vitro stimulation with 89pep, indicates the dominance of this epitope in the response to MCMV. No 89pep-specific IFNγ was detected in salivary gland cell cultures after immunization with the different peptides (data not shown). Thus, infection of the salivary gland with MCMV appeared to be needed for recruitment to the organ of 89pep-specific IFNγ producing cells (FIGS. 1A and 3).

The response of spleen cell cultures to stimulation with p458 induced high levels of IFNγ in mice immunized with p458 or p458-89pep, but not in other groups; this indicates that the responses were immunologically specific (FIG. 4). No significant IL-4 secretion after either immunization was detected; nonetheless the cells were capable of secreting IL-4 after stimulation with Con-A. IL-4 levels measured after Con-A stimulation in vitro were 242 pg/ml, 146 pg/ml, 184 pg/ml and 317 pg/ml for IFA-only, 89pep, p458, and p458-89pep respectively. Taken together, these results imply that the protection induced by p458-89pep was associated with elevation in MCMV-specific IFNγ production.

Example 4

Figure 5A:
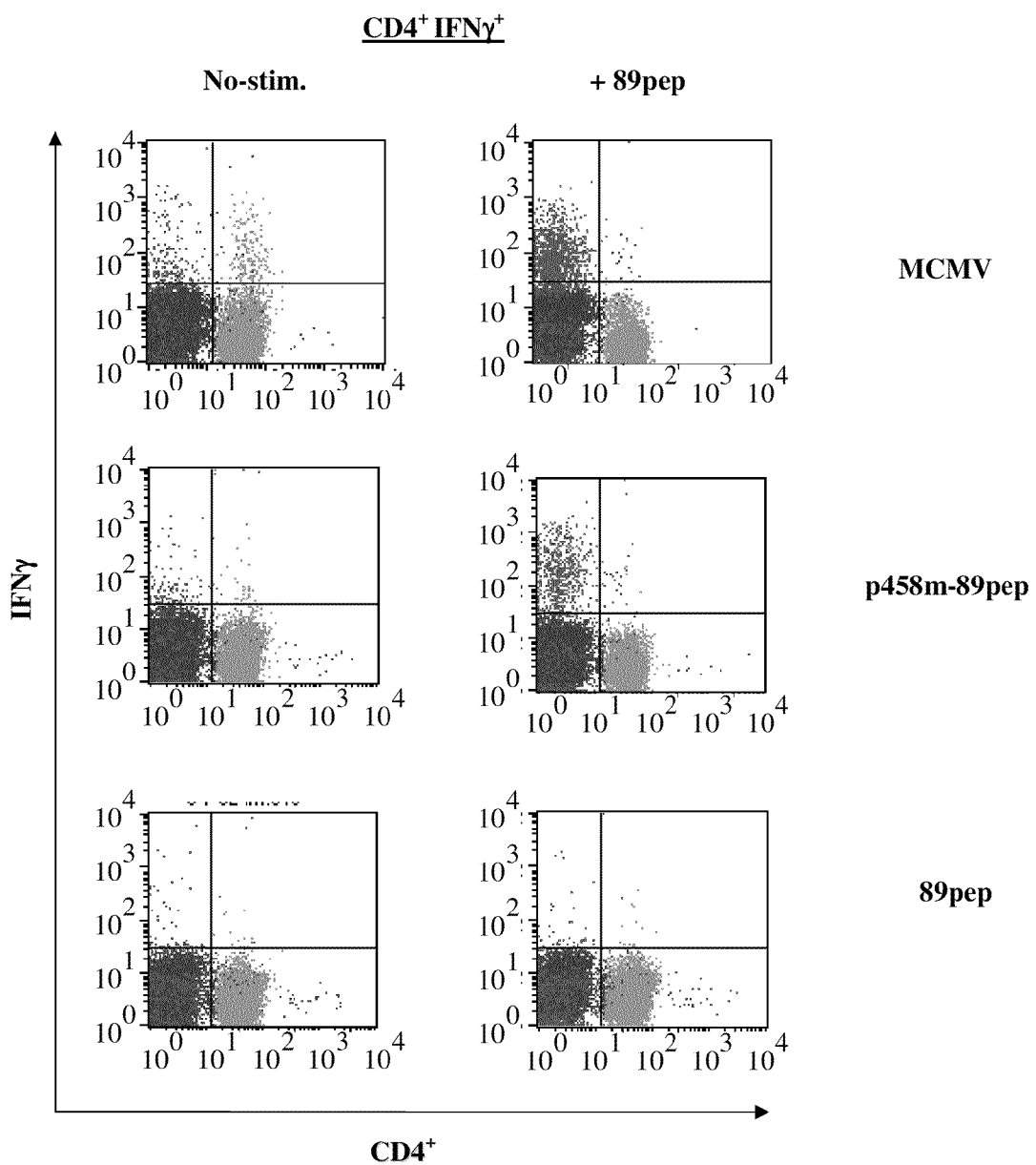
FIG. 5. IFNγ-positive spleen cells after vaccination with p458-89pep. Spleen-cell cultures were prepared 7 days after vaccination with various peptides, or after challenge of naïve mice with MCMV. After 5 days of stimulation in vitro with 89pep or without stimulation (No-stim), the cells were stained for CD4 (FIG. 5A) or CD8 (FIG. 5B) markers and for IFNγ. Numbers (27.43, 9.89 and 0.41) are percentage of IFNγ$^+$ cells in total CD8$^+$ cells. Results are from 1 representative experiment of 2 performed.
Figure 5B:
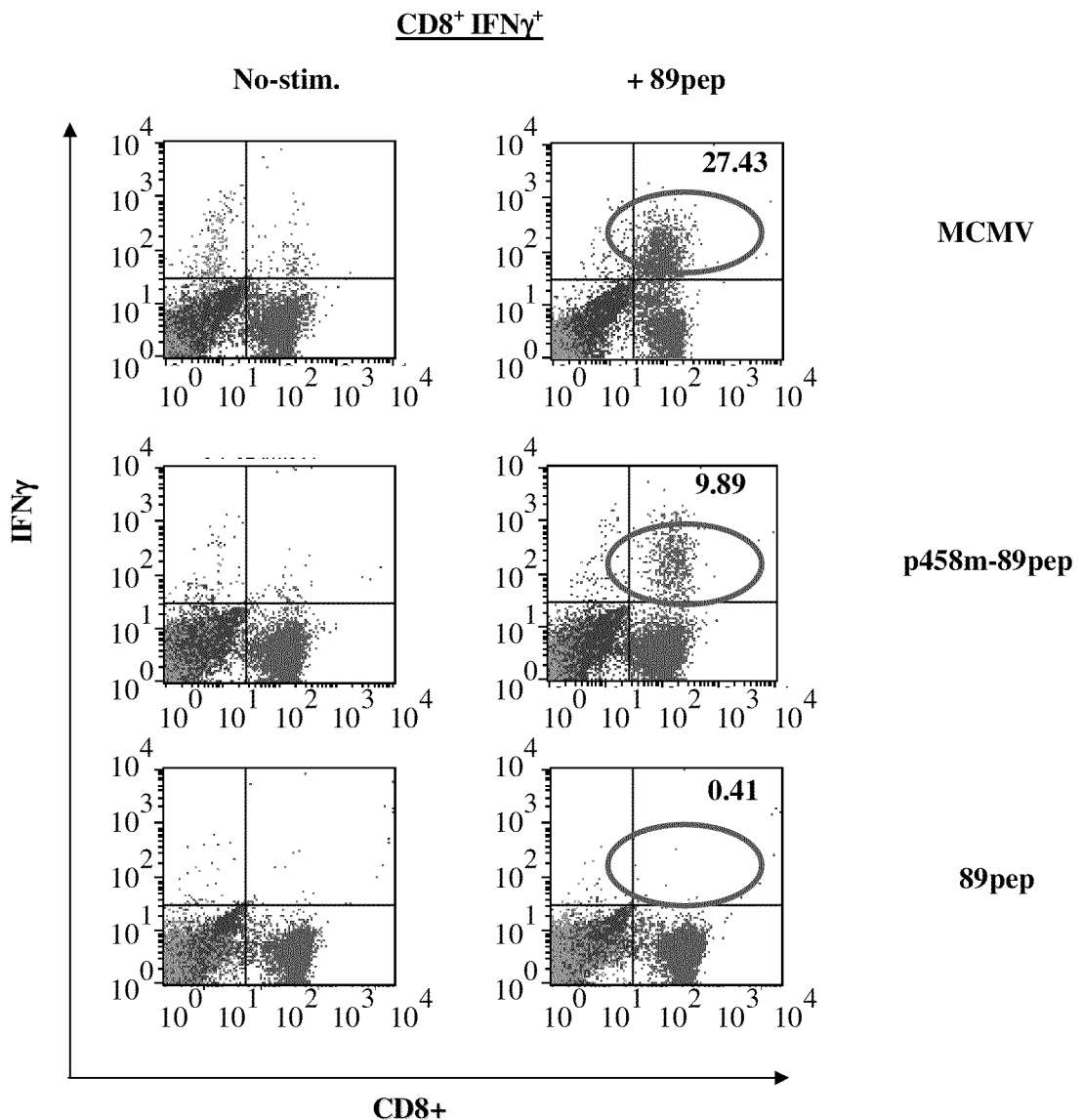

Immunization with p458-89pep Induces 89pep-Specific IFNγ$^+$CD8$^+$ T Cells and CTL Activity We characterized the nature of cells secreting the IFNγ by flow cytometry. Mice were immunized once with the different peptides and an additional group was infected with MCMV. Seven days later, spleens were removed and cell suspensions were cultured for 5 days with or without 89pep. Immunization with p458-89pep followed by 5 days of re-stimulation with 89pep induced IFNγ$^+$CD8$^+$ T cells and no IFNγ$^+$CD4$^+$ T cells (FIG. 5); very few IFNγ$^+$CD8$^+$ T cells were detected after immunization and re-stimulation with 89pep alone (FIG. 5B). Infection with MCMV and re-stimulation with 89pep induced the highest percentage of IFNγ$^+$CD8$^+$ T cells (FIG. 5B). Staining was specific to IFNγ since no CD8$^+$IL-4$^+$ or CD8$^+$IL-5$^+$ cells were observed.

Figure 6:
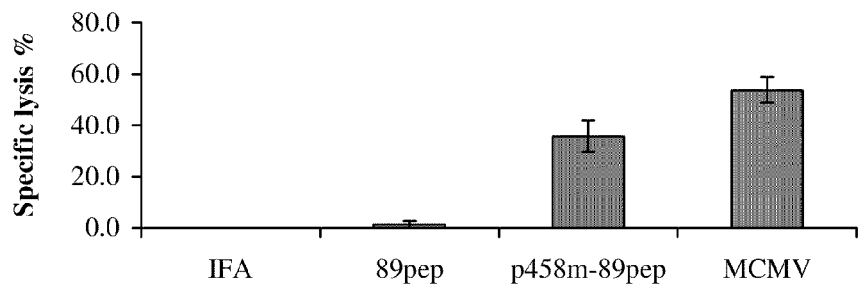
FIG. 6. CTL activity in spleen cell cultures after vaccination with p458-89pep. Spleen-cell cultures were prepared 7 days after immunization with various peptides or after challenge of naïve mice with MCMV. A control group received IFA without any peptide. CTL activity was measured after 6 days of stimulation in vitro with 89pep (10 μg/ml). Target cells were P815 pulsed with the 89pep (1 μg/ml). E:T ratio is 25:1. The data represent the average (±SE) of 3 different experiments.

We also investigated whether the CD8$^+$IFNγ$^+$ cells induced by the p458-89pep were able to lyse specifically 89pep-loaded target cells. Mice were immunized once and 7 d later, spleens were harvested and re-stimulated with 89pep. Six days later, lytic activity was assayed on P815 (H-2$^d$) loaded with the 89pep. No lytic activity was observed from the cultures of 89pep-immunized mice, but CTLs induced by p458-89pep lysed the target cells (FIG. 6). Similar to our results with IFNγ production by CD8$^+$ T cells, the 89pep-specific lytic activity induced by MCMV infection was higher than that induced by p458-89pep immunization.

Example 5

Salivary Gland-Specific Response after Immunization and Virus Challenge

We found, above, that IFNγ secretion in the salivary gland was virus-specific and depended on MCMV infection (FIGS.

Figure 7:
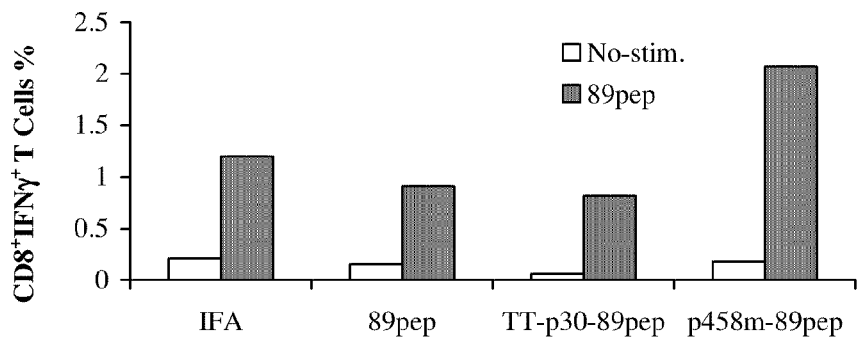
FIG. 7. IFNγ-positive salivary gland mononuclear cells 28 days after MCMV challenge of vaccinated mice. Mice were vaccinated and then challenged with MCMV. Cells were stained for CD8 and for IFNγ. No-stimulation (No-stim) or stimulation with 89pep (89pep) relates to the presence of 89pep during the 8 h incubation with golgi-stop step in the ICCS protocol for IFNγ. Results are from 1 representative experiment of 2 performed.

1 and 3). In the present experiment, we monitored IFNγ production in immunized mice 28 days after virus challenge. Staining of mononuclear cells for IFNγ-production was performed immediately after excision of the salivary gland, and stimulation with 89pep for 8 hr. The salivary glands of mice immunized with IFA, 89pep or TTp30-89pep and challenged with virus contained infectious virus on day 28 post challenge (FIG. 2). Likewise, CD8$^+$IFNγ$^+$ cells were observed in these day 28-infected salivary glands. In contrast, mice immunized with p458-89pep showed no infectious MCMV in the salivary gland 28 days after infection (FIG. 2). Nevertheless, the number of CD8$^+$IFNγ$^+$ cells was larger than that of the other groups (FIG. 7). This indicates that vaccination with p458-89pep induced a large reservoir of 89pep-specific CD8$^+$ T cells along with termination of salivary gland infection.

Figure 14A:
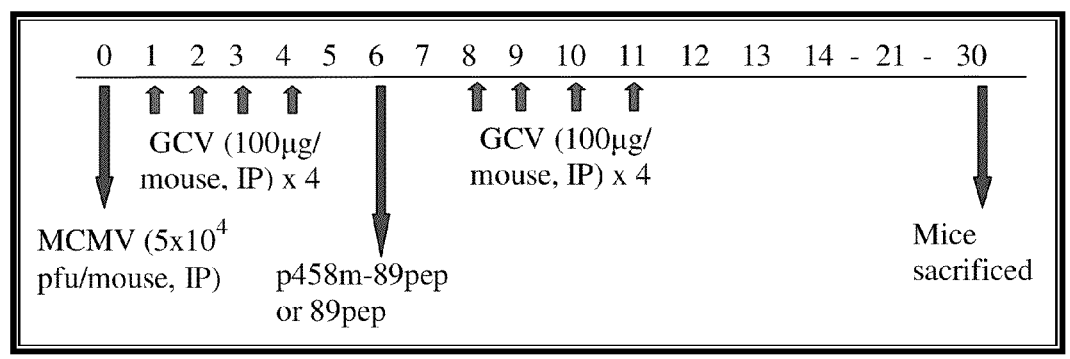
FIG. 14. p458-89pep reduces viral load of MCMV-infected mice. A. The experimental design. B. PCR amplification of the 363 bp product of MCMV IE-1.

Example 6 p458-89pep Reduces Viral Load of MCMV-Infected Mice 3-week old BALB/c mice were challenged i.p. with $5 \times 10^4$ pfu of MCMV (day 0). On day 6, mice were immunized once with IFA alone, 89pep or p458-89pep emulsified in IFA, as described above. Mice were treated with 100 μg of the anti viral medication Gancyclovir (GCV, Roche, Basel, Switzerland) i.p. on days 1, 2, 3, 4, 8, 9, 10 and 11 after challenge. Mice were sacrificed on day 30 after challenge and MCMV-DNA was measured by a PCR assay in the salivary glands, as specified above (FIG. 14A).

Figure 14B:
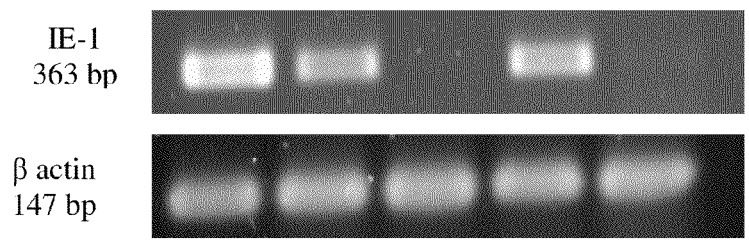

As can be seen in FIG. 14B, immunization with p458-89pep was able to suppress CMV load at the salivary gland even when applied after CMV challenge and in combination with GCV. GCV treatment alone did not suffice for therapy; also GCV treatment combined with one immunization with the non-conjugated 89pep did not affect CMV load. Only GCV treatment combined with one p458-89pep immunization reduced viral load to undetectable levels.

B. WNV Vaccination

Materials and Methods

Mice

BALB/c female mice were purchased from Harlan Olac (Jerusalem, Ill.) at the age of 14 days (10-12 g body weight). Mice were maintained under specific pathogen free conditions and were allowed to adjust to the facility for 1 week before experiments were performed. Mice were used at the age of 3-6 weeks unless otherwise stated. Age- and sex-matched animals were used as controls. Mice were maintained in isolation cages and were fed and watered ad libitum. The mouse experiments were approved and performed according to the guidelines of the Ben Gurion University, Faculty of Health Sciences, Animal Safety Committee.

Cell Cultures

The Vero cell line was derived from African Green Monkey (ATCC® number: CCL-81). The cells were grown in DMEM supplemented with 10% FCS, 1% nonessential amino acids and antibiotics. The cells were maintained in a humidified atmosphere at 37° C. in 5% $CO_2$ and were used for growing virus stocks, virus titration and neutralization assays.

Virus, Virus Titrations and WNV Antigen

The strain of West Nile Virus (WNV) was isolated from a human case of WNV infection (Goldblum et al., 1954). Signature amino acid motifs indicate that this strain belongs to lineage I. Virus plaque assays were performed on Vero cell monolayers in 24 well plates as previously described (Ben-Nathan et al., 1996). Virus stock titers were expressed as plaque-forming units (pfu) per ml. A single virus stock containing $5 \times 10^7$ pfu/ml was prepared in Vero cells, stored in aliquots at −70° C., and was used throughout this study. WNV antigen (WNV Ag) was prepared as previously described (Ben-Nathan et al., 2003).

Peptides

Peptides were synthesized at Sigma-Aldrich (Rehovot, Israel). Peptide purity was ascertained by analytical reversed-phase HPLC and amino acid (aa) analysis and was assessed on >95% purity. The sequences of the six peptides synthesized are: Ep15 (derived from the E3 domain of WNV)-LVTVNPFVSATANS, SEQ ID NO:11; p458 (the active peptide derived from mouse HSP60)-NEDQKIGIEIIKRALKI, SEQ ID NO:2; p32 (p458-Ep15 combined)-NEDQKIGIEIIKRALKILVTVNPFVSATANS, SEQ ID NO:13; pmock, a negative control for p458 (the p431 peptide of the mycobacterial HSP60, 442val-deleted)-EGDEATGANIKVALEA, SEQ ID NO:7; p458-89pep (combined p458 and 89pep, 89pep is a nonapeptide, YPHFHPTNL SEQ ID NO:5, which consists of a MCMV pp 89 ie1-CTL epitope)-NEDQKIGIEIIKRALKIYPHFHPTNL, SEQ ID NO:6. The mycobacterial p431 peptide (442val-deleted) was used as a negative control peptide since it is homologous in sequence to mammalian p458, but did not elicit a CD4$^+$-dependent immune response or antibodies against itself or p458.

Antibodies and Sera

Human intravenous immunoglobulin-IL (IVIG-IL): the IgG preparation from Israeli donors (IVIG-IL; OMRIGAM 5% intravenous IgG) containing 50 mg/ml IgG (total protein 5% w/v) was a gift from Omrix Biopharmaceuticals Ltd, Israel. This product has an anti-WNV antibody titer of 1:1600 by ELISA and of >1:80 by plaque-reduction neutralization testing (PRNT) (Ben-Nathan et al., 2003). Mouse WNV antiserum was prepared by intraperitoneal (IP) injection of 5-week old BALB/c mice with $1 \times 10^4$ pfu of WNV per mouse. Two weeks later, surviving mice were boosted with $1 \times 10^4$ pfu and bled 7 days later. Blood was centrifuged (4000 rpm for 7 min), and serum was collected and stored at −20° C. The antibody titer, measured by ELISA, was 1:2400. Serum from mock-injected naïve mice was used as a negative control.

Recognition of WNV-Ag and Peptides by IVIG and Mouse Sera

ELISA tests were performed according to the method described by Martin et al (Martin et al, 2000) with slight modifications. Briefly, microtiter plates were coated and incubated overnight at 4° C. with 100 μl of the different peptides (1 μg/well) or WNV antigen diluted 1:700 in coating buffer ($NaHCO_3$, pH=9.6). After incubation, the coating buffer was decanted and the plates were washed twice in PBS containing 0.05% Tween 20 and 0.2% sodium azide (washing buffer). After blocking for 1 h with a 200 μl/wen of PBS containing 0.05% Tween 20 and 2.5% nonfat dry milk, the plates were washed 4 times in washing buffer and 100 μl of IVIG-IL or mouse sera at 1:40 dilution were added to each well (2-4 wells per sample). Negative and positive controls of human or mouse sera were tested in each plate. After incubation for 1 h at 37° C. in a humidified atmosphere, the plates were washed 5 times, and 1000 of 1:1000 diluted HRP-Streptavidin-conjugated anti-human IgG (Sigma-Aldrich) or 1:1000 diluted HRP-Streptavidin-conjugated anti-mouse IgG (SouthernBiotech, Birmingham, Ala.) respectively, was added to each well. After incubation at 37° C. for 1 h, the plates were washed 5 times and 1000 of TMB substrate (DAKO Carpinteria, Calif.) was added to each well and incubated at room temperature for 30 min. The color intensity was measured by ELISA-reader (Dynatec MR 5000) at the absorbance of 405 nm.

Lymphocyte Proliferation Assay

Splenocytes from immunized or naive mice were prepared as described above, resuspended in complete RPMI in a final concentration of $2 \times 10^5$ cells per well in 96-well plates and stimulated in vitro with either 10 µg/ml of different peptides, 10 µl/ml of WNV-Ag, or 5 µg/ml of Concanavalin-A (Con-A). Cell cultures were incubated at 37° C. in 5% $CO_2$ for 5 days. At the end of incubation, 1 µCi of $^3$H-Thymidine (Amersham Biosciences, Buckinghamshire, England) was added to each well for 12 h. Radioactive counting was performed on a β-counter (WALLAC 1409).

Immunization of Mice with Peptides and WNV Challenge

The immunizing dose of each peptide was equimolar to 15 µg of p458 (Konen Waisman et al., 1999). All peptides were emulsified in incomplete Freund's adjuvant (IFA), and injected at 50 µl/mouse intrafootpad (IFP). Mice were immunized with the different peptides 2-3 times according to the experimental protocol. One week after the last immunization, mice were bled and sacrificed. Spleens were harvested, splenocyte cultures prepared and tested for T cell proliferation and cytokine secretion. Blood samples were centrifuged (4000 rpm for 7 min), and then sera were collected and tested for anti-WNV antibodies by ELISA and neutralization assays.

To study the immunogenicity and protective efficacy of the peptides, groups of 3-week old mice were immunized and boosted according to the following protocol: mice were immunized IFP and boosted once or twice, 1 week apart. One week after the last boost, the mice were challenged IP with $1 \times 10^6$ pfu of WNV. Mortality was recorded for the next 21 days. For virology studies, surviving and moribund mice were sacrificed on day 7 after the challenge, and organs were harvested for virus titrations and RT-PCR.

Virus Load in Brain Tissue of Infected Mice

Brain tissues were removed from infected or immunized and challenged mice, and 10% (wt/vol) homogenates were prepared in DMEM-10% DMSO. The homogenates were then aliquoted and stored at −70° C. until further analysis. Virus levels were determined by plaque titration on Vero cell monolayers as previously described (Ben-Nathan et al., 1996), and expressed as pfu/0.1 gr brain tissue.

RNA Extraction and RT-PCR

RNA was extracted from brain tissues from mice using RNEasy Midi Kit (QIAGEN, Hilden, Germany), and RT-PCR was performed on RNA extracts using Endo-Free Reverse Transcriptase (Ambion, Huntingdon, UK) and Bio-mix-Red (Bioline, London, UK). WNV E protein primers (5'-ACGAAGTGGCCATTTTTGTC-3', SEQ ID NO:81/5'-TTGATGCAGAGCTCCCTCTT-3', SEQ ID NO:82) were chosen using Primer3 program (Whitehead Institute for Biomedical Research). PCR products were electrophoretically separated on 1.5% agarose gel, stained with ethidium bromide and imaged using a CCD camera (Imagechem 5500).

Preparation of Spleen Cell Cultures and Cytokine Analysis

Spleens of immunized mice were harvested, and spleen pulp was extruded from the capsule in RPMI-1640 medium supplemented with 100 U/ml penicillin, 100 µg/ml streptomycin, 2 mM glutamine, 10 mM HEPES and 5% FCS (base-RPMI). Spleen cell suspensions were passed through a cell strainer, washed, treated for 2 min with ACK lysing buffer (0.15M $NH_4Cl$, 0.01 $KHCO_3$) for elimination of erythrocytes, and washed twice in base-medium. Splenocytes were resuspended in RPMI-1640 medium supplemented with 100 U/ml penicillin, 100 µg/ml streptomycin, 2 mM glutamine, 10 mM HEPES, $5 \times 10^{-5}$M β-mercaptoethanol and 10% FCS (complete RPMI) in a final concentration of $5 \times 10^6$ cells/ml in a 24-well plates. Cell suspensions were stimulated in vitro with either 10 µg/ml of different peptides, 10 µl/ml of WNV-Ag, or 5 µg/ml of Con-A. The cells were then incubated at 37° C. in 5% $CO_2$ for 72 h. Supernatants were collected, diluted by 2, and IFNγ and IL-4 concentrations were measured by indirect ELISA method using commercial kits (PharMingen, San Diego, Calif.) according to manufacturer instructions.

Virus Plaque Reduction Neutralization Testing (PRNT)

The titer of neutralizing antibodies was determined using a modified plaque reduction test (PRNT). Briefly, serial 2 fold dilutions (1:4 to 1:512) of mouse sera were prepared in 96-well flat-bottom microtiter plates and $10^4$ pfu of WNV in equal volumes was added to duplicate wells of each dilution. After 30 min of incubation at room temperature, $5 \times 10^4$ of Vero cells were added to each well of the sera-virus mixtures. The plates were incubated for 72 h in a humidified atmosphere at 37° C. and 5% $CO_2$ and plaques were counted. Plaque-reduction neutralizing antibody titers were expressed as the reciprocal of the highest dilution that gave 50% plaque reduction ($PRNT_{50}$).

Isotypes of Anti-WNV Antibodies

Plates were coated with the WNV-Ag diluted 1:700 in coating buffer. After overnight incubation at 4° C., blocking and washing, various dilutions of mouse sera were added in triplicates. Negative and positive controls of mouse sera were tested in each plate. Total IgG assessment was performed using HRP-Streptavidin-conjugated anti-mouse IgG (SouthernBiotech). For antibody isotype identification, incubation with biotin-conjugated anti-mouse IgG1, IgG2a, IgG2b, IgG3, IgA and IgM antibodies (PharMingen, San Diego, Calif.) was followed by incubation with 1:1000 diluted HRP-Streptavidin (Jackson Laboratories, West Grove, Pa.). After substrate addition the color intensity was measured by ELISA-reader at 405 nm.

Example 7

Identification of a WNV Epitope

Based on the antigenic propensity method (Kolaskar et al., 1990), calculated using a free B-cell epitope program (BcePred Server, http://www.imtech.res.in/raghava/bcepred/index.html), and based on a free MHC epitope program Pro-Pred server, http://www.imtech.res.in/raghava/propred), we have identified a p15 peptide from different WNV-E proteins (from the immunogenic E3 domain, aa LVTVNPFVSVA-TANS or aa LVTVNPFVSVATANA; SEQ ID NOS:11 and 12, respectively) as a candidate B-cell continuous epitope and MHC-II-restricted epitope of the WNV (recognized by different human and murine MHC-II molecules).

Figure 8:
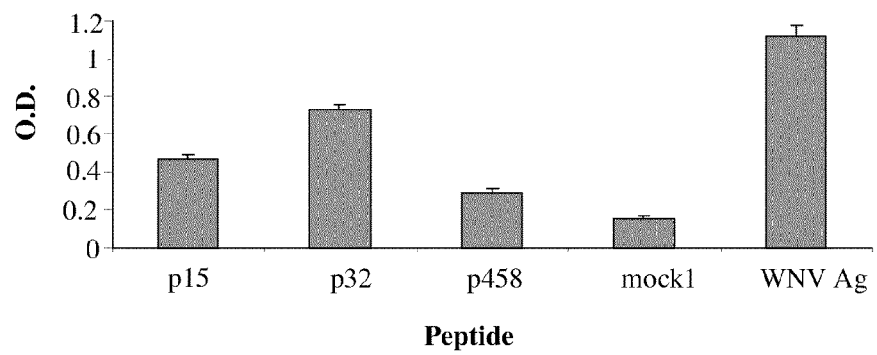
FIG. 8. Recognition of peptides by IVIG-IL. Wells were coated with the different peptides (1 μg/well) or with the WNV-Ag (1:700 dilution). After blocking and washing, IVIG-IL were added at 1:40 dilution and binding was detected as described in methods (ELISA). Background of ELISA (no peptide at well, 0.078 OD to 0.120 OD in different experiments) was subtracted from each experimental point. Results are the average of 4 independent ELISA experiments. Bars, ±SD.
Figure 9:
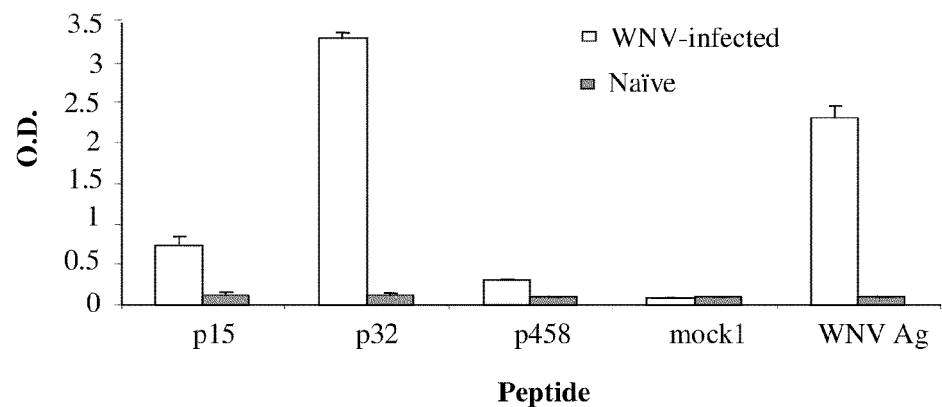
FIG. 9. Recognition of peptides by serum from WNV-infected mice. Wells were coated with the different peptides (1 μg/well) or with the WNV-Ag (1:700 dilution). After blocking and washing, naïve (gray columns) or WNV-infected (white columns) murine sera were added at 1:40 dilution and binding was detected as described in methods (ELISA). Results are from 1 representative experiment of 3 performed. Each experimental point was performed in triplicate. Bars, ±SD.
Figure 10:
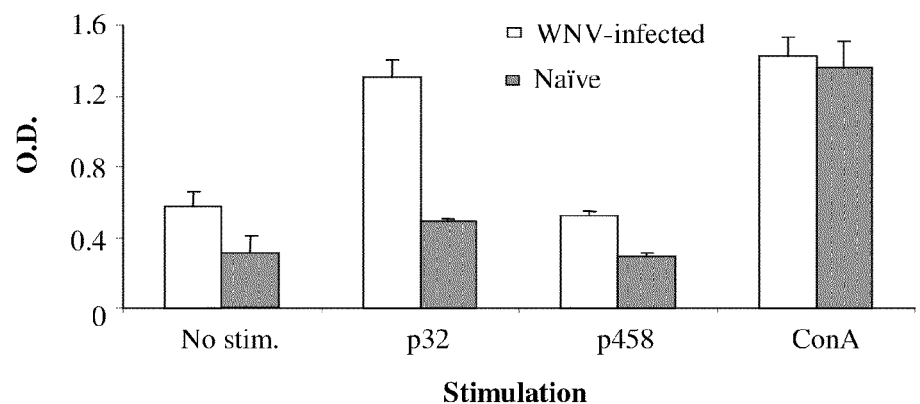
FIG. 10. Proliferation of splenocytes from WNV-infected mice following in vitro stimulation with the different peptides. Mice were infected with 66pfu of WNV. Six days after, spleens were harvested and splenocytes were cultured with the different peptides (10 μg/ml) or with ConA (5 μg/ml) for 3 days. Proliferation of cells derived from naïve (gray columns) or WNV-infected (white columns) mice was measured using WST-1 method. Results are the average of 3 independent proliferation experiments. Bars, ±SD.

Next, it was examined whether the candidate epitope is recognized by a serum immunoglobulin pool taken from Israeli donors (IVIG-IL), which contains anti-WNV Abs. Wells were coated with the different peptides (1 µg/well) or with the WNV-Ag (1:700 dilution). After blocking and washing, IVIG-IL was added at 1:40 dilution and binding was detected. The results demonstrate for the first time that the p15 peptide is recognized by IVIG-IL (FIG. 8). Subsequently, mice were challenged IP with a sublethal dose of WNV ($10^4$ pfu) WNV and 14 days later surviving mice were re-infected with the same dose of WNV. Sera were collected 7 days after the second challenge, and ELISA assays were performed. As can be seen in FIG. 9, serum from WNV-infected mice specifically recognized p15, and, to a greater extent, the p15 conjugate p32. In addition, T cells from these mice proliferated in response to in vitro stimulation with the p15 conjugate p32 (FIG. 10). Thus, the phenotype of p15 as WNV-B-cell epitope and WNV-MHC II-restricted peptide was hereby demonstrated.

Example 8

Immunization with p458-p15 Elicits WNV Protection

We showed that HSP60-p458 (NEDQKIGIEIIKRALKI SEQ ID NO:2) used as a carrier peptide for a MHC-I epitope of CMV enhanced immune response to CMV and immunization with the chimeric peptide, p458-CMV epitope, cleared MCMV from salivary glands of mice challenged with the virus. In accordance we tested the WNV-protective efficacy of p458-p15 (NEDQKIGIEIIKRALKILVTVNPFVSVATANS) chimeric peptide (termed as p32, SEQ ID NO:13). Table 2 summarizes 5 different experiments; immunization with p15 alone showed slight protective efficacy while immunization with a mixture of p15 and p458 did not protect mice. Nonetheless, when mice were immunized with p32, the chimeric p458-p15 peptide, a high degree of protection against a fatal challenge with virulent WNV was achieved.

TABLE 2

In vivo protective efficacy of p32 immunization against WNV challenge

| | Treatment - Deaths/Total (% deaths) | | | | |
|---|---|---|---|---|---|
| | No treatment | p15 (x3) | p32 (x3) | p458 (x3) | p15 + p458 (x3) |
| Mortality (dead of total) | 22/32 (69%) | 8/15 (53%) | 2/21 (10%) | 4/7 (57%) | 5/7 (71%) |

Mice were immunized 3 times with the different peptides or a peptide mix at 7 day intervals. Seven days after the 3rd immunization mice were challenged with $10^6$ pfu of WNV and survival was monitored for 21 days post challenge. Results are the summary of 5 different experiments, performed in the same conditions.

To investigate whether immunization with p32 resulted in clearance of WNV, virus levels in the brain, which is the prime target organ of this neurotropic virus, were examined.

Mice were immunized 3 times with p32 at 7 day intervals. Seven days after the last immunization, immunized and non-immunized mice were challenged IP with $10^6$ pfu of WNV. Seven days after challenge, mice were sacrifice and different organs were extracted (brain, lungs, heart, liver and spleen). Organs were taken also from control naïve mice (non-immunized and non-infected matched mice). Viral loads were determined by RT-PCR for viral genome and plaque assay for infectious virus titers (pfu/0.1 gr tissue). RT-PCR results are representative from one experimental mouse while infectious titers are the average for all experimental groups. * Detection level of the plaque assay is <$10^1$.

Virus levels were determined in the brain by RT-PCR and plaque assay on day 7 after challenge (FIG. 15). Virus titers were up to $4 \times 10^8$ pfu/ml in the non-immunized and challenged mice, while in the naïve and in the immunized and challenged group no virus was detected (FIG. 15). These findings confirm that vaccination of mice with the p32 peptide protects them against an otherwise fatal WNV infection.

Example 9

Immunization with p458-p15 Induces WNV-Neutralizing Abs

Figure 11A:
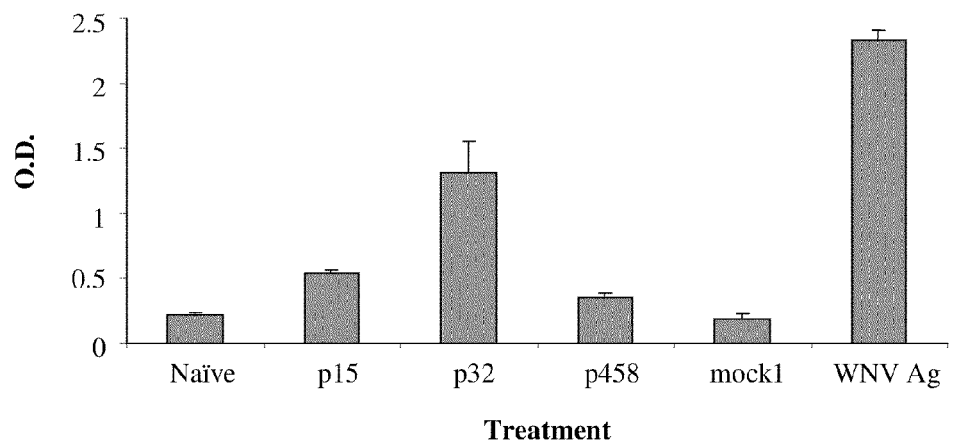
FIG. 11. Anti-WNV Abs in the sera of mice immunized with different peptides or with WNV Ag. (A) Mice were immunized 3 times with the different peptides or WNV-Ag at 7 day intervals. Seven days after the 3$^{rd}$ immunization mice were bled and sera were tested as follows. Wells were coated with WNV-Ag (1:700 dilution). After blocking and washing, the different sera were added at 1:40 dilution and binding was detected as described in methods (ELISA). Results are the average of 4 independent ELISA experiments. Bars, ±SD. (B) Isotypes of Anti-WNV antibodies.

We next investigated the immune responses elicited following immunization with p32. Immunization with p32 induced high titer of WNV-specific Abs as compared to immunization with p15 alone (FIG. 11A). The Ab generated following immunization with p32 exhibited WNV-neutralizing capacity, essential for the protective effect of the p32 vaccine (Table 3).

TABLE 3

Titers of anti-WNV neutralizing Abs in the sera of p32-immunized or WNV-infected mice on day 7 after treatment

| Source of serum | Titers of anti-WNV neutralizing Abs |
|---|---|
| Naïve mice | <1:10 |
| p32-immunized mice | 1:80 |
| WNV-infected mice | 1:320 |

Mice were either immunized 3 times with p32 or challenged with WNV. Seven days after the 3rd immunization or WNV challenge, respectively, mice were bled and titers of WNV-neutralizing Abs in sera were tested (PRNT$_{50}$). Results are the average of 4 independent ELISA experiments.

Figure 11B:
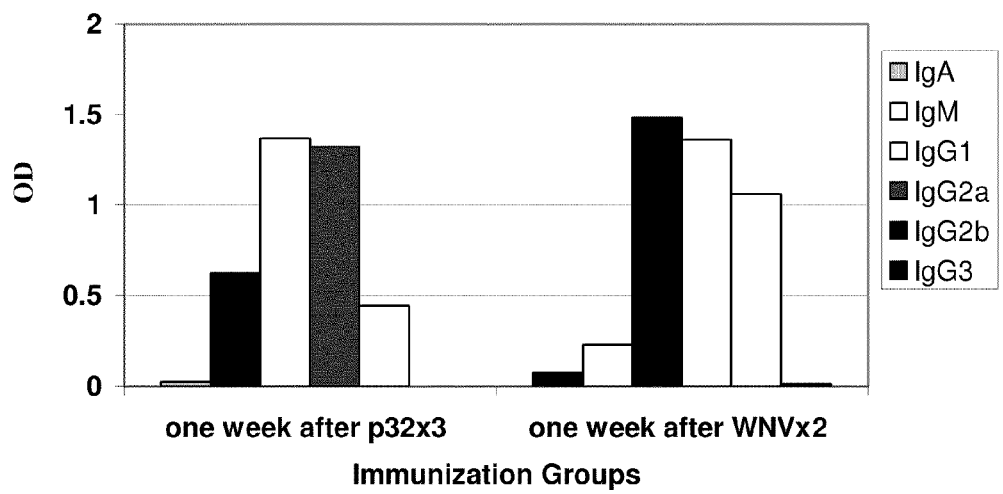

Next, it was examined whether p32 immunization and sublethal infection with WNV induce similar isotypes of anti-WNV antibodies. WNV-Ag was used as the antigen in the ELISA plates. FIG. 1B shows that levels of anti-WNV IgG1 and IgG2a isotypes were similarly high in sera from p32-immunized and WNV-infected mice. WNV-specific IgG2b levels were higher in sera from WNV-infected mice while WNV-specific IgM were higher in p32-immunized mice. Neither IgA nor IgG3 specific for WNV were detected in both types of sera (FIG. 11B).

Example 10

Figure 12:
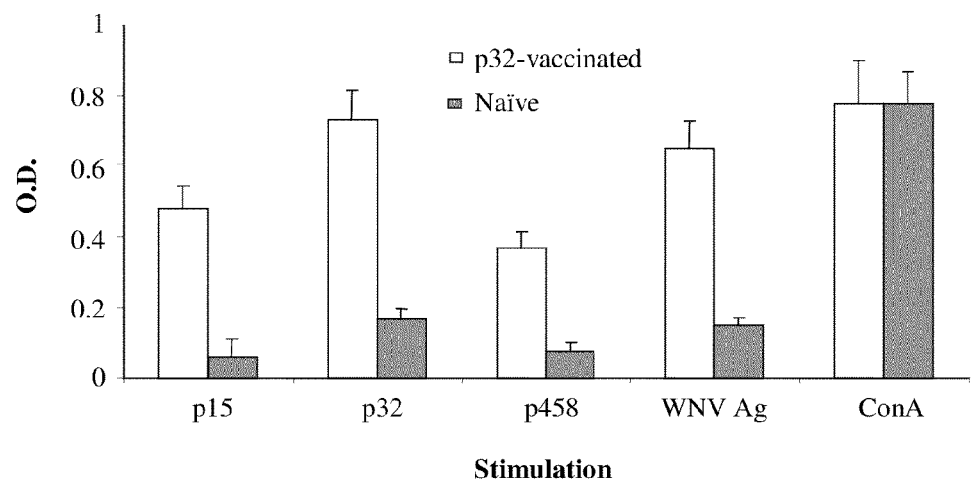
FIG. 12. Proliferation of splenocytes from p32-immunized mice following in vitro stimulation with the different peptides. Mice were immunized 3 times with p32 at 7 day intervals. Seven days after the 3$^{rd}$ immunization, spleens were harvested and splenocytes were cultured with the different peptides or WNV-Ag (10 μg/ml) or with ConA (5 μg/ml) for 3 days. Cell proliferation was measured using WST-1 method. Results are the average of 3 independent proliferation experiments. Bars, ±SD.
Figure 13:
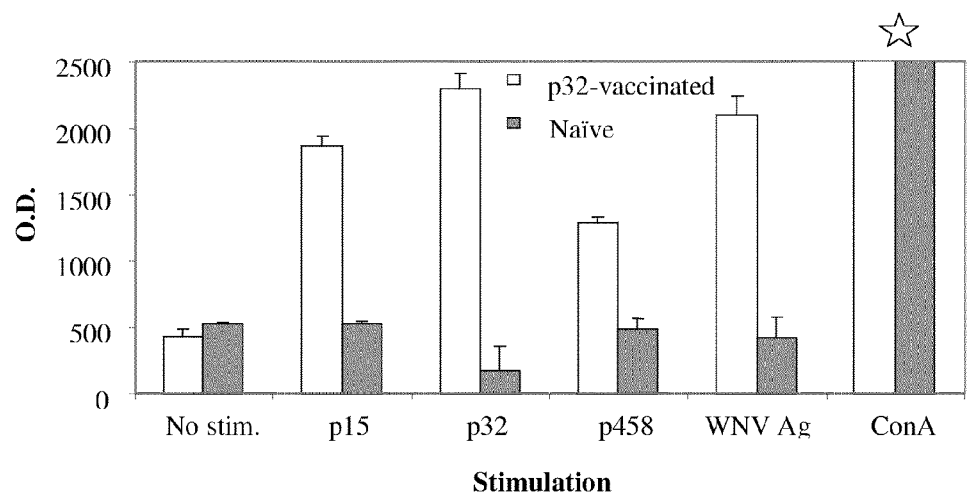
FIG. 13. IFNγ secretion in the spleens of p32-vaccinated mice on day 7 after immunization. Mice were immunized 3 times with p32 at 7 day intervals. Seven days after the 3$^{rd}$ immunization, spleens were harvested and splenocytes were cultured with the different peptides or WNV-Ag (10 μg/ml) or with ConA (5 μg/ml) for 3 days. IFNγ levels in the supernatants were measured as described in methods. Results are the average of 4 independent proliferation experiments. Bars, ±SD.

Immunization with p458-p15 Induces WNV-Specific T Cell Response and IFN-γ Secretion WNV-specific T-cell responses were examined as follows: Six-week old BALB/c mice were infected with a sublethal dose of WNV ($0.66 \times 10^2$ pfu), and spleens were harvested 6 days later. Spleen cell suspensions were prepared, cultured in 96 wells plates and incubated for 3 days with the 10 μg/ml of EP15, p32, p458 or Con-A (5 μg/ml) for 3 days. Cell proliferation was measured by the WST-1 method and the results are the average of 3 independent experiments. As shown in FIG. 12, splenocytes from mice immunized with p32 proliferated in response to in vitro stimulation with WNV antigen. This stimulation also induced secretion of high levels of IFNγ, essential for TH1 response that characterizes virus-protective immune responses (FIG. 13).

Example 11

Immunization with Conjugates of p458 and Ec27 with Viral Antigens

Conjugates of p458 and Ec27 with the novel viral antigens of the invention, having amino acid sequences as set forth in SEQ ID NOS:13-14, 23, 56-75 and 77-79 (see Table 4 below), are synthesized as described above.

| Virus | P458 conjugate (SEQ ID NO): | Ec27 conjugate (SEQ ID NO): |
|---|---|---|
| WNV | NEDQKIGIEIIKRALKILVTVNPFVSVATANS (13)<br>NEDQKIGIEIIKRALKILVTVNPFVSVATANA (14)<br>NEDQKIGIEIIKRALKIYIVVGRGEQQINHHWHK (23)<br>NEDQKIGIEIIKRALKIGRLVTVNPFVSVATANS (65)<br>NEDQKIGIEIIKRALKIGRLVTVNPFVSVATANA (66) | KKARVEDALHATRAAVEEGVGRLVTVNPFISTGGANNKVM (77)<br>KKARVEDALHATRAAVEEGVLVTVNPFVSVATANA (78)<br>KKARVEDALHATRAAVEEGVYIVVGRGEQQINHHWHK (79) |
| Yellow fever birus | NEDQKIGIEIIKRALKIGILVTVNPIASTNDDEVLIE (56) | KKARVEDALHATRAAVEEGVGILVTVNPIASTNDDEVLIE (67) |
| St. Louis encephalitis virus | NEDQKIGIEIIKRALKIGRLVTVNPFISTGGANNKVM (57) | KKARVEDALHATRAAVEEGVGRLVTVNPFISTGGANNKVM (68) |
| Murray Valley encephalitis virus | NEDQKIGIEIIKRALKIGRMVTANPYVASSTANAKLV (58) | KKARVEDALHATRAAVEEGVGRMVTANPYVASSTANAKVL (69) |
| Kunjin virus | NEDQKIGIEIIKRALKIGRLVTVNPFVSVSTANAKVL (59) | KKARVEDALHATRAAVEEGVGRLVTVNPFVSVSTANAKVL (70) |
| Japanese encephalitis virus | NEDQKIGIEIIKRALKIGRLVTVNPFVATSSANSKVL (60) | KKARVEDALHATRAAVEEGVGRLVTVNPFVATSSANSKVL (71) |
| Dengue virus type 1 | NEDQKIGIEIIKRALKIGRLITANPIVTDKEKPVNIE (61) | KKARVEDALHATRAAVEEGVGRLITANPIVTDKEKPVNIE (72) |
| Dengue virus type 2 | NEDQKIGIEIIKRALKIGRLITVNPIVTEKDSPVNIE (62) | KKARVEDALHATRAAVEEGVGRLITVNPIVTEKDSPVNIE (73) |
| Dengue virus type 3 | NEDQKIGIEIIKRALKIGRLITANPVVTKKEEPVNIE (63) | KKARVEDALHATRAAVEEGVGRLITANPVVTKKEEPVNIE (74) |
| Dengue virus type 4 | NEDQKIGIEIIKRALKIGRIISSTPLAENTNSVTNIE (64) | KKARVEDALHATRAAVEEGVGRIISSTPLAENTNSVTNIE (75) |

Mice are immunized 3 times with the different peptides or with control peptides (corresponding non-conjugated viral antigens and with the carrier peptides alone) at 7 day intervals, as described above. Seven days after the 3rd immunization mice are challenged with $10^6$ pfu of the corresponding flavivirus and survival is monitored for 21 days post challenge.

In other experiments, the immunogenicity of the conjugates is determined by the following assays: in some experiments, mice are immunized and assayed for serum titers of virus-specific and viral peptide-specific antibodies by ELISA essays, as described above. In other experiments, LNC from immunized mice are examined in the presence of the corresponding viral antigen in proliferation assays and IFN-γ secretion assays, as described above.

Example 12

Use of Ec27-Antigen Conjugates for Increasing the Immunogenicity of a Viral Antigen Mice were immunized with the following peptides as described in Example 8 using the following peptides: p15 (SEQ ID NO:11), p32 (SEQ ID NO:13), Ec27-p15 (KKARVEDALHATRAAVEEGVLVTVNPFVSVATANS, SEQ ID NO:77), and Mock-p15 (EGDEATGANIKVALE-ALVTVNPFVSVATANS, SEQ ID NO:80—the p431 peptide fused to p15).

Spleens were harvested 10 days after the immunization and splenocytes were cultured with p15 (25 μg/ml) for 3 days. Cell proliferation and IFNγ levels in the supernatants of spleen cell cultures were measured. Results are the average of 3 independent proliferation experiments. Ec27-Ep15* and Ec27-Ep15** are two identical but independent groups in the same experiment.

As shown in FIG. 16, p458 and Ec27 were both able to increase the immunogenicity of p15. Vaccination with conjugates comprising either p458 or Ec27 fused to the N-terminus of p15 resulted in enhanced proliferation and IFN-γ secretion of spleen cells in the presence of p15, compared to those of spleen cells derived from animals vaccinated with p15 conjugated to the control peptide. Spleen cells from mice immunized by IFA alone or unconjugated Ec27 did not induce significant proliferation and IFN-γ secretion when incubated with p15.

Example 13

Figure 17A:
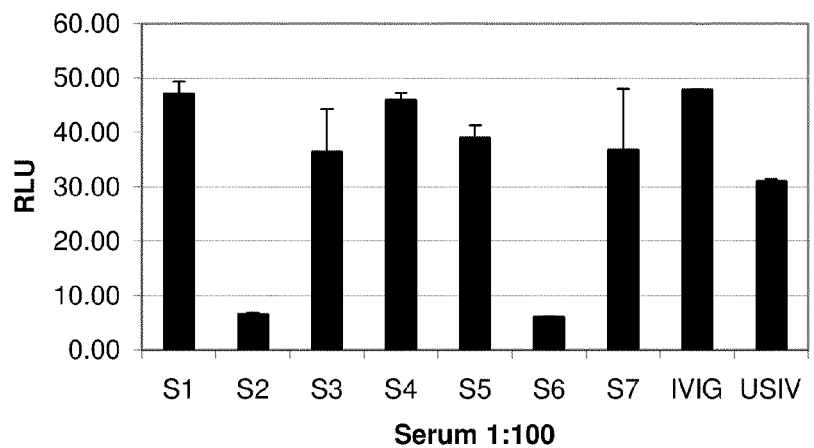
FIG. 17. Specific recognition of p15 (A, B) and p17 (B) by sera from WNV-infected human patients.
Figure 17B:
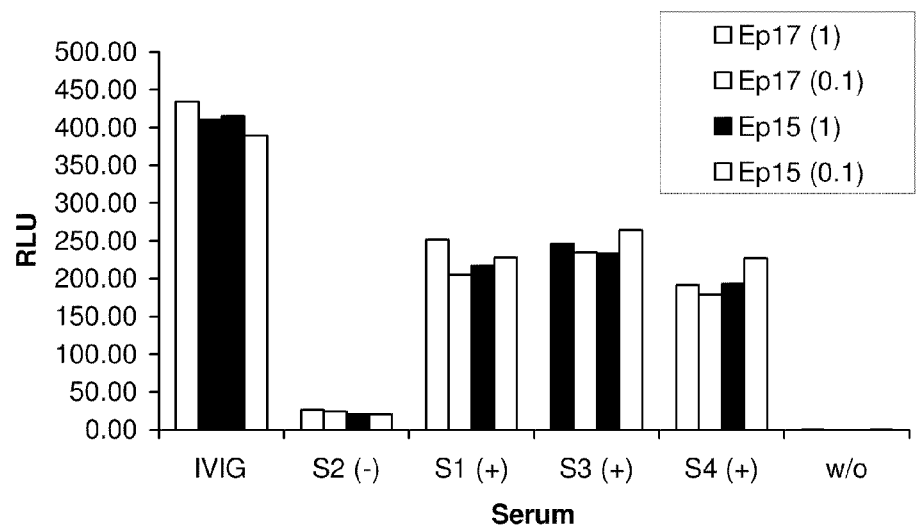

Specific Recognition of the WNV Peptides by Sera Derived from WNV-Exposed Subjects Sera from WNV-exposed and non-exposed human subjects was assayed for antibodies recognizing the novel WNV peptide antigens, p15 (SEQ ID NO:11) and p17 (SEQ ID NO:21). FIG. 17 presents the results of an ELISA test in which the p15 and p17 served as the antigen, human sera were used as the primary antibody and HRP-conjugated anti-human Abs were used as the secondary antibody. RLU are the relative luminescence units produced by HRP activity on the luminal substrate.

Sera S2 and S6 are from human that were not infected with WNV while sera S1, S3-S5 and S7 are from human that had history of WNV infection. IVIG is pool of plasmas from Israeli citizens that was shown to contain antibodies against WNV.

As can be seen, both p15 and p17 were specifically recognized by WNV-exposed sera and not by sera from unexposed subjects. Human sera from Dengue-infected humans also did not recognize the p15 (data not shown). Thus, p15 and p17 are suitable diagnostic peptides useful for determining WNV exposure or infection.

Example 14

Identification of Ec27, an Immunodominant Peptide Derived from *E. coli* GroEL

To find dominant T helper cell epitopes derived from the sequence of the *E. coli* variant of HSP60 (GroEL), BALB/c mice were inoculated with heat-inactivated *E. coli* bacteria and the proliferative responses of draining LNCs to a set of overlapping GroEL peptides (Table 5), and the whole GroEL molecule (Purchased from Sigma), were analyzed.

TABLE 5

Overlapping peptides of the *E. coli* HSP60 molecule (GroEL); amino acid designation is corresponding to accession number gi:45686198 without the first methionine residue, SEQ ID NO: 83.

| Peptide Number | Position |
| --- | --- |
| 1 | 1-20 |
| 2 | 16-35 |
| 3 | 31-50 |
| 4 | 46-65 |
| 5 | 61-80 |
| 6 | 76-95 |
| 7 | 91-110 |
| 8 | 106-125 |
| 9 | 121-140 |
| 10 | 136-155 |
| 11 | 151-170 |
| 12 | 166-185 |
| 13 | 181-200 |
| 14 | 196-215 |
| 15 | 211-230 |
| 16 | 226-245 |
| 17 | 241-260 |
| 18 | 256-275 |
| 19 | 271-290 |
| 20 | 286-305 |
| 21 | 301-320 |
| 22 | 316-335 |
| 23 | 331-350 |
| 24 | 346-365 |
| 25 | 361-380 |
| 26 | 376-395 |
| 27 (Ec27) | 391-410 |
| 28 | 406-425 |
| 29 | 421-440 |
| 30 | 436-455 |
| 31 | 451-470 |
| 32 | 466-485 |
| 33 | 481-500 |
| 34 | 496-515 |
| 35 | 511-530 |
| 36 | 526-545 |
| 37 | 526-547 |

Figure 18A:
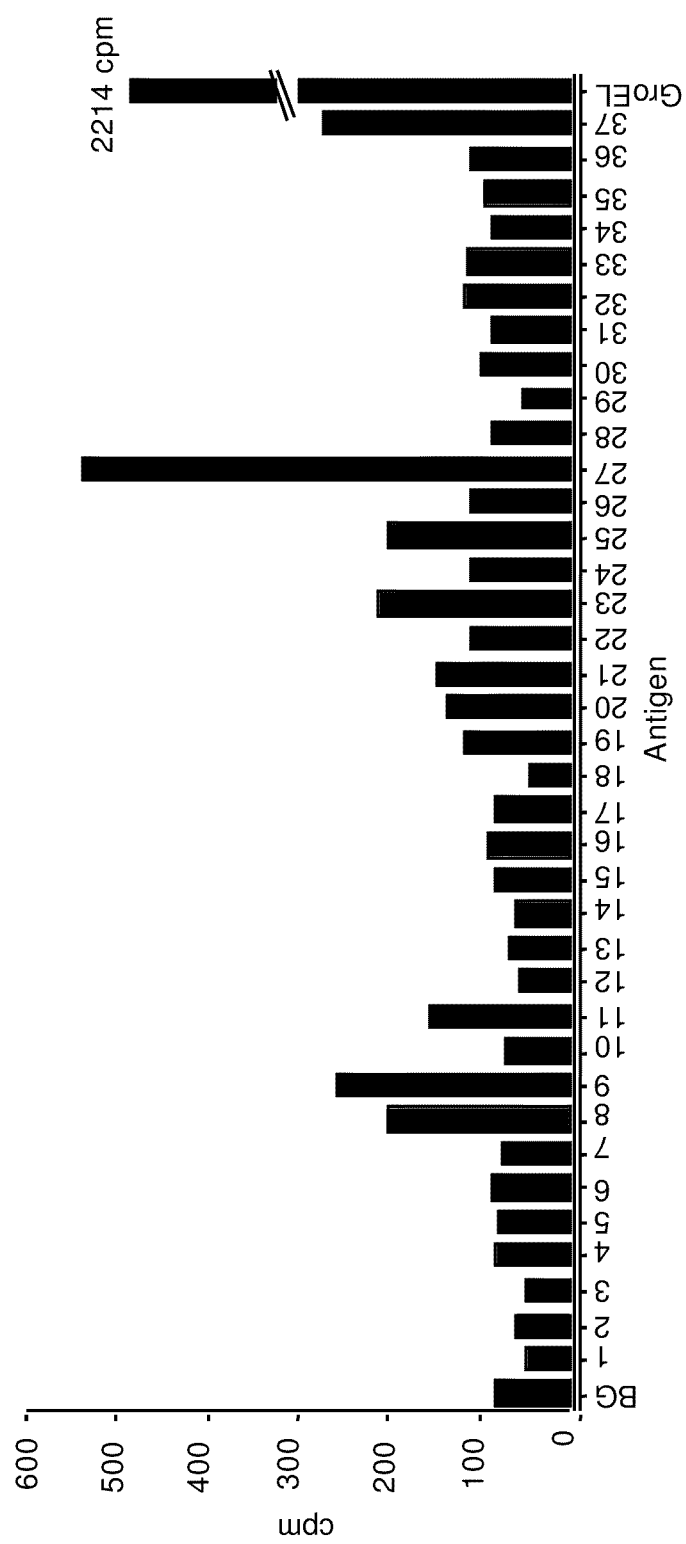
FIG. 18. Proliferative response of BALB/c lymph node cells to overlapping GroEL peptides after immunization with *E. coli* bacteria (A) or GroEL (B)
Figure 18B:
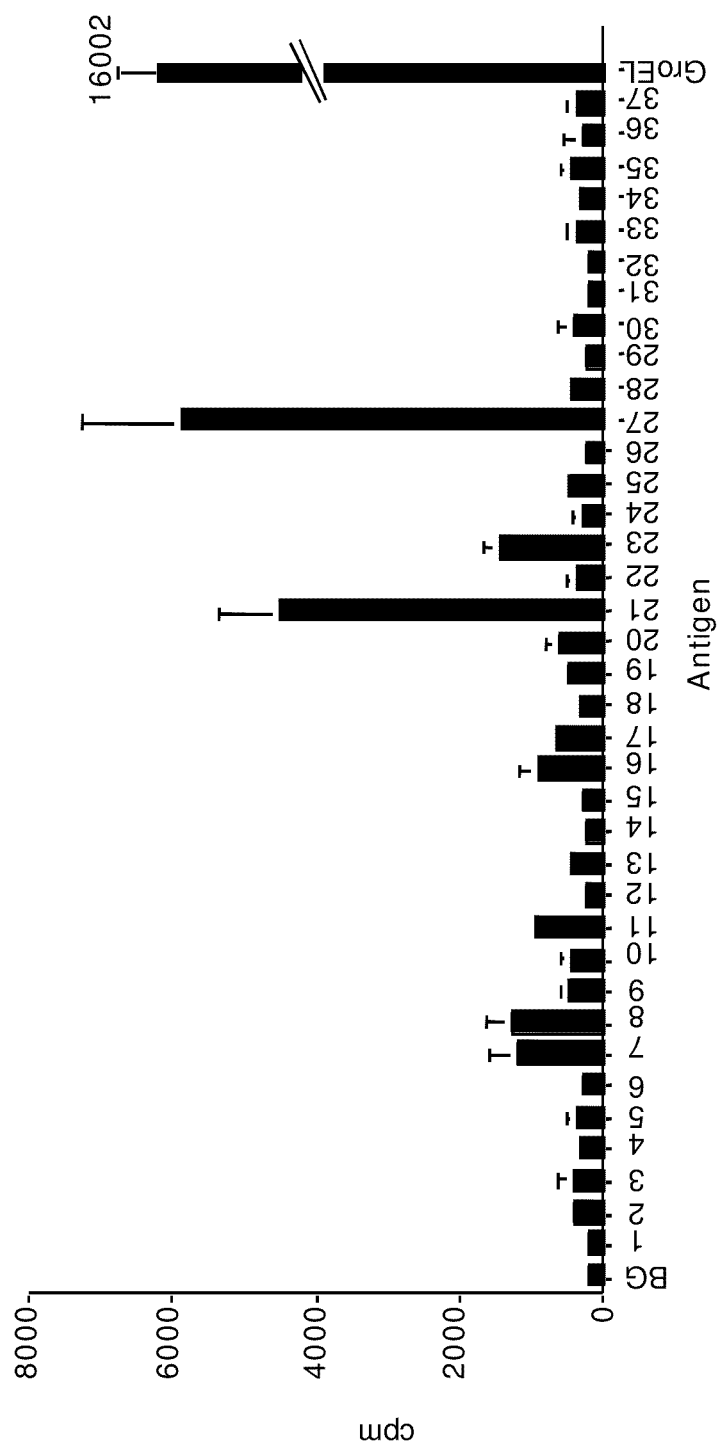

BALB/c mice were immunized s.c. with $10^7$ glutaraldehyde-attenuated *E. coli* bacteria (FIG. 18A) in PBS, or with 30 µg GroEL in PBS (FIG. 18B). Ten days later lymph node cells ($2\times10^5$ cells per well) were assessed for specific proliferation to the indicated overlapping GroEL peptides (20 µg/ml). After 96 hours of incubation, the $^3$H-thymidine incorporation was assessed as a measure of proliferation. Results are shown as mean cpm of quadruplicate wells. The standard deviations are indicated.

T-cell proliferation assays were performed as follows: Draining lymph node cells (LNC) of immunized mice were cultured ($2\times10^5$/well) in 200 µl RPMI 1640 medium supplemented with 2 mM glutamine, non-essential amino acids, 1 mM sodium pyruvate, 100 U/ml penicillin, 100 µg/ml streptomycin (BioLab, Jerusalem, Israel), $5\times10^{-5}$M β-mercaptoethanol (Fluka AG, Buchs, Switzerland), 10 mM HEPES buffer (Sigma), and 1% syngeneic normal mouse serum. After four days of incubation, [$^3$H]-thymidine (0.5 µCi of 5 Ci/mmol, Nuclear Research Center, Negev, Israel) was added for additional sixteen hours, and the thymidine incorporation was measured. Results are expressed as the mean cpm, or the stimulation index (SI), i.e. the mean cpm of test cultures (with antigen) divided by the mean cpm of control cultures (without antigen).

As can be seen in FIG. 18A, a peptide corresponding to amino acid residues 391-410 of GroEL was highly immunogenic. Immunization of BALB/c mice with the GroEL molecule instead of the whole *E. coli* bacteria led to a similar proliferative response of draining LNC (FIG. 18B) to the same GroEL peptides and the whole GroEL molecule as used for FIG. 18A: both immunogens gave rise to an immune response to the GroEL molecule and, predominantly, to the Ec27 peptide of GroEL.

It was also tested whether the Ec27 peptide itself is immunogenic by immunization of BALB/c mice with 20 µg of the Ec27 peptide in IFA.

BALB/c mice were immunized s.c. with 20 µg Ec27 peptide emulsified in IFA. Ten days later lymph node cells were taken and assessed for specific proliferation of $2\times10^5$ cells in the presence of the Ec27 peptide, the acetylcholine receptor peptide 259-271 (AcR 259-271, VIVELIPSTSSAV SEQ ID NO:84), or GroEL at the concentrations 10 µg/ml, 2 µg/ml, or without antigen (BG). Results are shown as mean cpm of quadruplicate wells. The standard deviations are indicated.

Figure 19:
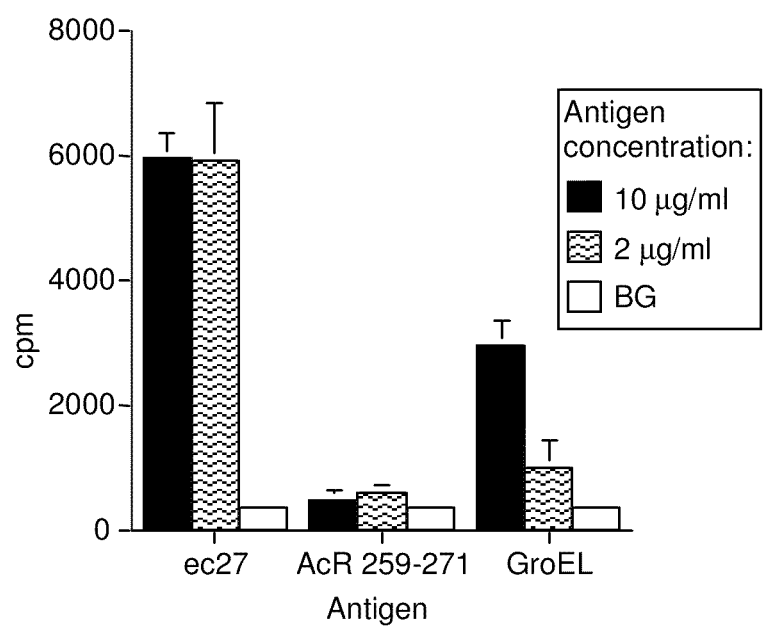
FIG. 19. Proliferative response of BALB/c lymph node cells to immunization with the Ec27 peptide FIG. 20. Proliferative response of different mouse strains to immunization with the Ec27 peptide. BALB/c (A), BALB/k (B), and BALB/b (C) and SJL (D) mice were immunized s.c. with 20 mg of the Ec27 peptide emulsified in IFA. Ten days later lymph node cells (2×10$^5$ cells per well) were assessed for specific proliferation to the Ec27 peptide (full circles), the ec35 peptide (empty circles), or the acetylcholine receptor peptide 259-271 (empty triangles). After 96 hours of incubation, the $^3$H-thymidine incorporation was assessed as a measure of proliferation. Results are shown as mean cpm of quadruplicate wells. The standard deviations are indicated.
Figure 20A:
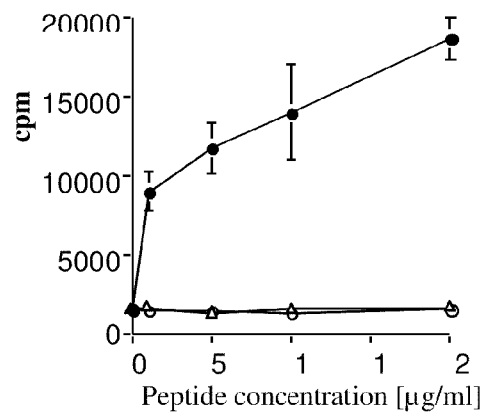
Figure 20B:
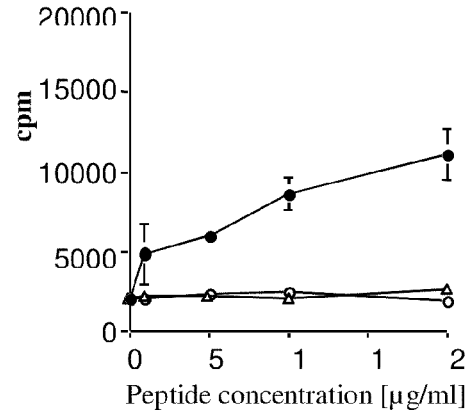
Figure 20C:
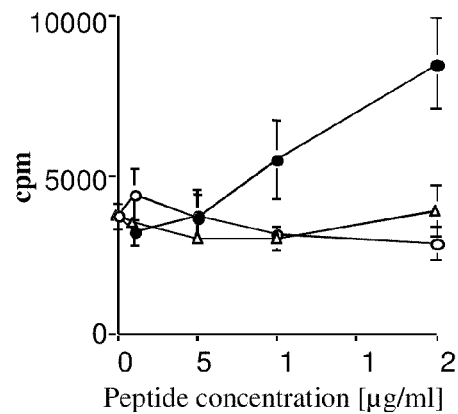
Figure 20D:
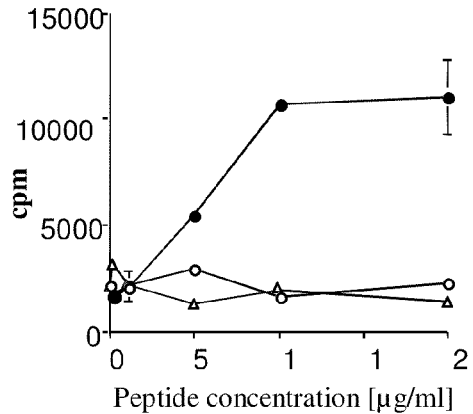

FIG. 19 shows that the lymph node cells of immunized mice responded the Ec27 peptide and to the whole GroEL molecule, but not to the control peptide AcR 259-271.

To learn whether the immunogenicity of the Ec27 peptide is restricted to a certain MHC haplotype, we compared four strains mice with different MHC haplotypes in their response to the Ec27 peptide. The immunized mice were of the BALB/c (H-2d), BALB/k (H-2k), BALB/b (H-2b), or SJL (H-$2^S$) strain. As can be seen in FIG. 20, all four different mouse strains responded specifically to the Ec27 immunogen peptide. Thus, the Ec27 peptide could replace the GroEL, or the whole bacteria in priming for a GroEL-specific immune response, due to its immuno-dominance.

Example 15

Use of the Ec27 Peptide as an Adjuvant for Antibody Responses

Figure 21A:
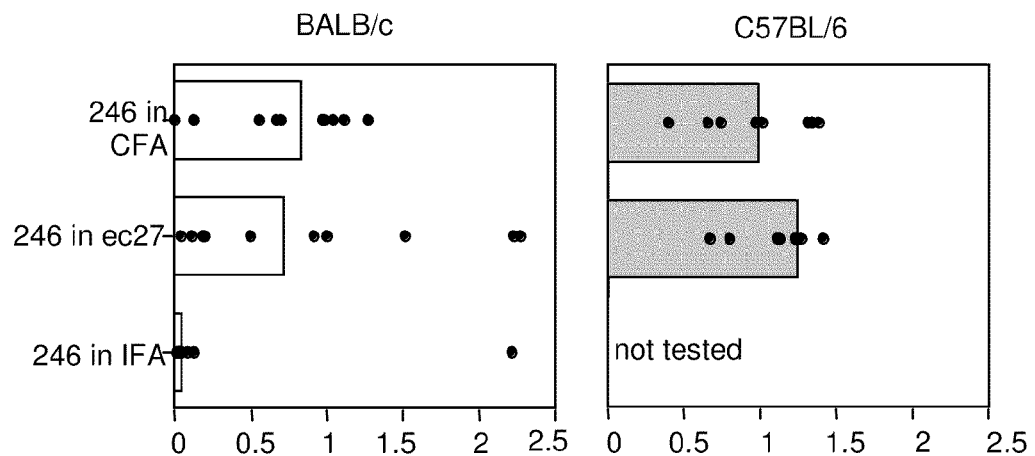
FIG. 21. Adjuvant effect of the Ec27 peptide. (A) anti-PAb-246 reactivity; (B) anti-p53 reactivity.
Figure 21B:
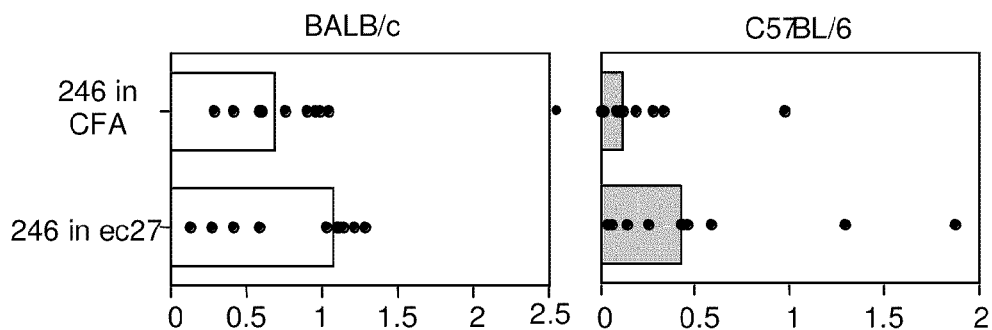

Because the Ec27 peptide was found to be an immunodominant peptide of the GroEL molecule, which is the major immunogen of bacteria, it was interesting to learn whether the Ec27 peptide can be used as an adjuvant, as can the bacteria. Therefore, BALB/c and C57BL/6 mice were immunized subcutaneously with 20 µg of the monoclonal anti-p53 antibody PAb-246 (described in Yewdell et al., 1986) in different immunogenic compositions: the antibody was either emulsified in Complete Freund's Adjuvant (246 in CFA), in Incomplete Freund's Adjuvant (246 in IFA), or together with 50 µg the Ec27 peptide (as a mixture) in IFA (246 in Ec27). Three weeks later, all mice received a boost of the PAb-246 antibody subcutaneously in IFA. Ten days after the boost, mice were bled and their antibody responses to the PAb-246 immunogen were compared by ELISA (FIG. 21A). Immunization of the PAb-246 antibody in IFA alone did not result in a significant antibody response. In contrast, immunization with the antibody in IFA mixed with the Ec27 peptide resulted in an effective antibody response in both strains. The adjuvant effect of the Ec27 peptide was comparable to the effect of CFA, which is one of the most potent adjuvant materials known. FIG. 21B shows the induction of anti-p53 antibodies in the immunized mice by ways of an idiotypic network, i.e. these anti-p53 antibodies are anti-idiotypic to the anti-PAb-246 antibodies. Again, the use of the Ec27 peptide as an adjuvant was at least as effective as the use of CFA.

Dots represent individual sera, bars indicate the median of each group.

Example 16

Use of the ec27 Peptide as an Adjuvant for p458-Polysachamide Conjugates

*S. pneumoniae* serotype 4 capsular polysaccharide (PnTy4) was obtained from the American Type Culture Collection (ATCC; Rockville, Md., USA). PnTy4 was coupled to carrier peptides by using 1-(3-dimethylaminopropyl)-3-ethylcarbodiimide hydrochloride (CDI; Aldrich, Wis., USA) using standard procedure.

The peptide carriers used in this example are: p458 (SEQ ID NO:2), p458s (SEQ ID NO:87, EGDIETGVNIVLKALTA), MOG (SEQ ID NO: 85, MEVGWYRSPFSRVVHLYRNGK).

BALB/c mice were immunized with the indicated peptide-polysaccharide conjugate in IFA or IFA mixed with 50 μg Ec27 as described above, in the WNV vaccination example. LNC were collected and assayed for nitric oxide (NO) production and proliferation.

Table 6 shows the levels of Nitric Oxide (NO) Production (nM) in lymph node cells (LNC) derived from mice immunized with peptide-sugar conjugates in IFA or in IFA+Ec27. The cells were cultured for 72 h with either Concanavalin A (Con A) or the peptide-sugar immunogen in the presence or absence of a macrophage cell line (J774). NO production was assayed using a Nitrate/Nitrile colorimetric assay according to the manufacturer's instructions.

| | LNC | | | LNC + J774 | | |
|---|---|---|---|---|---|---|
| Immunogen | BG | Con A | P458-Ty4 | BG | Con A | P458-Ty4 |
| P458-Ty4/IFA | 0.13 | 4.73 | 0.21 | 0.55 | 6.24 | 10.29 |
| P458-Ty4/ec27 | 0.18 | 3.32 | 2.36 | 0.66 | 4.33 | 34.97 |

| | LNC | | | LNC + J774 | | |
|---|---|---|---|---|---|---|
| Immunogen | BG | Con A | P458s-Ty4 | BG | Con A | P458s-Ty4 |
| $P458_S$-Ty4/IFA | 0.13 | 9.91 | 0.55 | 0.93 | 6.35 | 0.66 |
| $P458_S$-Ty4/ec27 | 0.18 | 8.53 | 2.41 | 0.45 | 5.23 | 27.73 |

The proliferation of lymph node cells in response to immunogen was performed as described above (Example 14).

Table 7 shows the proliferation of LNC derived from mice immunized with peptide-sugar conjugates in IFA or in IFA+ec27. The cells were cultured for 72 h with Concanavalin A (Con A), the peptide-sugar immunogen (Ty4), the peptide immunogen without the sugar, or the sugar conjugated to a control peptide (MOG-Ty4). The proliferative response is given as the stimulation index (SI).

TABLE 7 proliferation of LNC derived from mice immunized with peptide-sugar conjugates in IFA or in IFA + ec27.

| Immunogen | BG | Con A | P458-Ty4 | P458 | MOG-Ty4 |
|---|---|---|---|---|---|
| P458-Ty4/IFA | 1.0 | 2.3 | 4.7 | 2.9 | 2.7 |
| P458-Ty4/ec27 | 1.0 | 6.5 | 15.4 | 3.1 | 4.0 |

| Immunogen | BG | Con A | $P458_S$-Ty4 | $P458_S$ | MOG-Ty4 |
|---|---|---|---|---|---|
| $P458_S$-Ty4/IFA | 1.0 | 12.8 | 2.9 | 2.2 | 1.3 |
| $P458_S$-Ty4/ec27 | 1.0 | 15.3 | 8.7 | 2.1 | 6.5 |

In the tables, BG refers to background values; ConA refers to concanavalin A; P458-Ty4 is a conjugate between the p458 peptide and the *S. pneumoniae* serotype 4 capsular polysaccharide; P458s-Ty4 is a conjugate between the p458s peptide and the *S. pneumoniae* serotype 4 capsular polysaccharide.

REFERENCES

1. Mercer, J A, Spector, D H. J Virol 1986, 57 (2), 497-504.
2. Reddehase et al., Nature 1989, 337 (6208), 651-653.
3. Zajac et al., Curr Opin Immunol 1998, 10 (4), 444-449.
4. Matloubian et al., J Virol 1994, 68 (12), 8056-8063.
5. Konen Waisman et al., J Infect Dis 1999, 179 (2), 403-413.
6. Jindal et al., Mol Cell Biol 1989, 9 (5), 2279-2283.
7. Konen Waisman et al., 1995, 154 (11), 5977-5985.
8. Cohen, Immunol Today 1992, 13 (12), 490-494.
9. Anderton et al., Eur J Immunol 1993, 23 (1), 33-38.
10. Hermann et al., Eur J Immunol 1991, 21 (9), 2139-2143.
11. Koga et al., Science 1989, 245 (4922), 1112-1115.
12. Palmon et al., Antiviral Res 1996, 33 (1), 55-64.
13. Rager Zisman et al., Proc Soc Exp Biol Med 1973, 142 (4), 1174-1179.
14. Rapp et al., J Virol 1992, 66 (7), 4399-4406.
15. Panina-Bordignon et al., Eur J Immunol 1989, 19 (12), 2237-2242.
16. Brander et al., Clin Exp Immunol 1996, 105 (1), 18-25.
17. Keitel et al., Vaccine 1999, 18 (5-6), 531-539.
18. Palmon et al., J Virol Methods 2000, 86 (2), 107-114.
19. Amir-Kroll et al., J Immunol 2003, 170 (12), 6165-6171.
20. Lussow et al., Immunol. Letters 25:255-264 (1990)
21. Lussow, et al., Eur. J. Immunol. 21:2297-2302 (1991).
22. Barrios et al. Eur S of Immuol 22:1365 (1992)
23. Stewart, J. M. and Young, J. D. (1963), "Solid Phase Peptide Synthesis," W. H. Freeman Co. (San Francisco).
24. Meienhofer, J (1973). "Hormonal Proteins and Peptides," vol. 2, p. 46, Academic Press (New York).
25. Schroder, G. and Lupke, K. (1965). The Peptides, vol. 1, Academic Press (New York).
26. Sambrook et al., Molecular Cloning: A Laboratory Manual, Cold Spring Harbor Labs Press, 1989, 1992.
27. Peyman and Ulmann, Chemical Reviews, 90:1543-584 (1990).
28. Monath, Ann N Y Acad Sci 2001, 951, 1-12.
29. Pletnev et al., Virology 2003, 314 (1), 190-195.
30. Tesh et al., Emerg Infect Dis 2002, 8 (12), 1392-1397.
31. Hall et al., Proc Natl Acad Sci USA 2003, 100 (18), 10460-10464.

32. Casadevall, Nat Biotechnol 2002, 20 (2), 114.
33. Goldblum et al., Am J Hyg 1954, 59 (1), 89-103.
34. Ben-Nathan et al., Arch Virol 1996, 141 (3-4), 459-469.
35. Ben-Nathan et al., J Infect Dis 2003, 188 (1), 5-12.
36. Martin et al., J Clin Microbiol 2000, 38 (5), 1823-1826.
37. Yewdell et al., J Virol 59:444-452.
38. Kolaskar et al., FEBS, 276:172, 1990.
39. Ausubel et al., Current Protocols in Molecular Biology, John Wiley and Sons, Baltimore, Md. 1989.

The invention claimed is:

1. A vaccine composition comprising an antigen and a synthetic peptide adjuvant comprising a T cell epitope of HSP60 in which the synthetic peptide adjuvant has an amino acid sequence selected from the group consisting of KKARVEDALHATRAAVEEGV (Ec27; SEQ ID NO:76) and KKDRVTDALNATRAAVEEGI (Ec27h; SEQ ID NO:86) and analogs, homologs, derivatives and salts thereof having at least 80% amino acid identity to SEQ ID NO:76 and maintaining electric and hydrophobic properties of SEQ ID NOs: 76 and 86.

2. The composition of claim 1, wherein the antigen is selected from the group consisting of: a peptide, a peptide derivative, a protein, a polysaccharide, and an antibody.

3. The composition of claim 2, wherein the antigen is a viral antigen.

4. The composition of claim 3, wherein said viral antigen has an amino acid sequence as set forth in any one of SEQ ID NOS:11-12, 21 and 25-44 and analogs, homologs, derivatives and salts thereof having at least 90% amino acid identity to SEQ ID NOs: 11-12, 21 and 25-44.

5. The composition of claim 1, comprising a conjugate of the antigen and said synthetic peptide adjuvant.

6. The composition of claim 5 wherein the conjugate has an amino acid sequence as set forth in any one of SEQ ID NOS:67-75 and 77-79.

7. The composition of claim 1 comprising an admixture of the antigen and said synthetic peptide adjuvant.

8. A conjugate comprising a viral antigen covalently attached to a synthetic peptide carrier comprising a T cell epitope of HSP60 in which said synthetic peptide carrier has an amino acid sequence selected from the group consisting of KKARVEDALHATRAAVEEGV (Ec27; SEQ ID NO:76) and KKDRVTDALNATRAAVEEGI (Ec27h; SEQ ID NO:86) and analogs, derivatives and salts thereof having at least 80% amino acid identity to SEQ ID NO:76 and maintaining electric and hydrophobic properties of SEQ ID NOs: 76 and 86.

9. The conjugate of claim 8, wherein the viral antigen is derived from a virus belonging to a virus family selected from the group consisting of flaviviridae and herpesviridae.

10. The conjugate of claim 9, wherein the viral antigen is derived from West Nile Virus (WNV).

11. The conjugate of claim 9, wherein the viral antigen has an amino acid sequence as set forth in any one of SEQ ID NOS:11-12, 25-44 and 21.

12. The conjugate of claim 11 having an amino acid sequence as set forth in any one of SEQ ID NOS:67-75 and 77-79.

13. A vaccine composition comprising a conjugate according to claim 8 and a pharmaceutically acceptable carrier, adjuvant, excipient or diluent.

14. A method of immunizing a subject in need thereof against a viral infection comprising administering to the subject an effective amount of a vaccine composition according to claim 13.

15. The method of claim 14 wherein the subject is selected from a group consisting of: humans, non-human mammals and non-mammalian animals.

16. The method of claim 15 wherein the subject is human.

17. The method according to claim 14 further comprising steps prior to immunizing the subject comprising:
   isolating an antigen derived from a virus comprising at least one epitope selected from: a Cytotoxic T Lymphocyte (CTL) epitope, a B cell epitope and a Major Histocompatibility Complex type II (MHC II)-restricted epitope;
   covalently conjugating the antigen to said synthetic peptide carrier; and
   preparing a vaccine composition comprising the conjugate and a pharmaceutically acceptable carrier, adjuvant, excipient or diluent.

* * * * *